(12) United States Patent
Kosuge et al.

(10) Patent No.: US 8,580,400 B2
(45) Date of Patent: Nov. 12, 2013

(54) BICHRYSENE COMPOUND AND ORGANIC LIGHT EMITTING DEVICE HAVING THE COMPOUND

(75) Inventors: Tetsuya Kosuge, Yokohama (JP); Jun Kamatani, Tokyo (JP); Yosuke Nishide, Kawasaki (JP); Kengo Kishino, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/144,622

(22) PCT Filed: Mar. 12, 2010

(86) PCT No.: PCT/JP2010/054715
§ 371 (c)(1),
(2), (4) Date: Jul. 14, 2011

(87) PCT Pub. No.: WO2010/107097
PCT Pub. Date: Sep. 23, 2010

(65) Prior Publication Data
US 2011/0272683 A1 Nov. 10, 2011

(30) Foreign Application Priority Data
Mar. 16, 2009 (JP) ................. 2009-063011

(51) Int. Cl.
*H01L 51/54* (2006.01)
(52) U.S. Cl.
USPC ........... 428/690; 428/917; 313/504; 313/505; 313/506; 257/40; 257/E51.05; 257/E51.026; 257/E51.032; 585/26
(58) Field of Classification Search
USPC .................. 428/690, 917; 313/504, 505, 506; 257/40, E51.05, E51.026, E51.032; 585/27
See application file for complete search history.

(56) References Cited

U.S. PATENT DOCUMENTS 6,369,507 B1 * 4/2002 Arai .............................. 313/506
7,429,425 B2 9/2008 Ikeda et al.
(Continued)

FOREIGN PATENT DOCUMENTS

CN 1675149 A 9/2005
JP 2000-344691 A 12/2000
(Continued)

OTHER PUBLICATIONS

U.S. Appl. No. 13/146,315, filed Jul. 26, 2011.
(Continued)

*Primary Examiner* — Gregory Clark
(74) *Attorney, Agent, or Firm* — Fitzpatrick, Cella, Harper & Scinto

(57) ABSTRACT

Provided are a novel bichrysene compound and an organic light emitting device having high light emitting efficiency and excellent driving durability. The organic light emitting device includes an anode, a cathode, and a layer formed of an organic compound interposed between the anode and the cathode. The layer formed of an organic compound has a bichrysene compound represented by the following general formula (1).

(1)

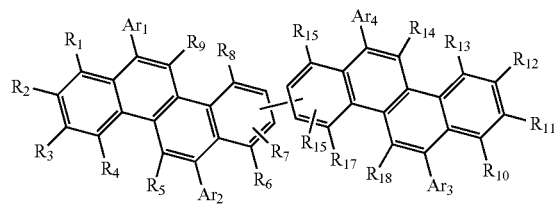

9 Claims, 2 Drawing Sheets

(56) References Cited

U.S. PATENT DOCUMENTS

| | | |
|---|---|---|
| 7,466,073 B2 | 12/2008 | Kishino et al. |
| 7,687,154 B2 | 3/2010 | Iwawaki et al. |
| 7,704,609 B2 | 4/2010 | Igawa et al. |
| 7,883,786 B2 | 2/2011 | Abe et al. |
| 7,914,907 B2 | 3/2011 | Iwawaki et al. |
| 2005/0189857 A1* | 9/2005 | Kobori ............ 313/110 |
| 2006/0134456 A1 | 6/2006 | Ikeda et al. |
| 2008/0200736 A1 | 8/2008 | Kosuge et al. |
| 2009/0009074 A1 | 1/2009 | Ikeda et al. |
| 2009/0066227 A1 | 3/2009 | Okinaka et al. |
| 2010/0194270 A1 | 8/2010 | Kawamura et al. |
| 2010/0219407 A1 | 9/2010 | Kamatani et al. |
| 2011/0108810 A1 | 5/2011 | Kishino |

FOREIGN PATENT DOCUMENTS

| | | | |
|---|---|---|---|
| JP | 2004-75567 A | 3/2004 | |
| JP | 2006-052323 * | 2/2006 | ............ C09K 11/06 |
| JP | 2006-52323 A | 2/2006 | |
| JP | 2006-52324 A | 2/2006 | |
| WO | 2009/008311 A1 | 1/2009 | |
| WO | 2009/008354 A1 | 1/2009 | |

OTHER PUBLICATIONS

Chinese Office Action issued in counterpart application No. 201080011753.2 dated May 6, 2013, along with its English-language translation—13 pages.

* cited by examiner

BICHRYSENE COMPOUND AND ORGANIC LIGHT EMITTING DEVICE HAVING THE COMPOUND

TECHNICAL FIELD

The present invention relates to a novel bichrysene compound and an organic light emitting device having the same.

BACKGROUND ART

An organic light emitting device is a device in which a thin film including a fluorescent light emitting organic compound or a phosphorescent light emitting organic compound is interposed between an anode and a cathode. Further, electrons and holes are injected from the respective electrodes to generate excitons of the fluorescent light emitting organic compound or the phosphorescent light emitting organic compound, and the organic light emitting device emits light when the excitons return to the ground state.

Recent progress of an organic light emitting device is remarkable, and the organic light emitting device is characterized by, for example, exhibiting high luminance at a low applied voltage, having various emission wavelengths, exhibiting high-speed responsiveness, and allowing a light emitting device to be thinned and lightened. This suggests that the organic light emitting device may be used for a wide variety of applications.

However, the present situation requires optical output with even higher luminance or higher conversion efficiency. In addition, many problems still remain to be solved regarding durability against the change over time due to long-term use, and deterioration caused by atmospheric gas containing oxygen, moisture, or the like, for example. Further, taking applications for a full color display and the like into consideration, it is necessary to emit blue, green, or red light with a high color purity, but such problem has not been sufficiently solved yet.

In view of the foregoing, many studies have been conducted on various fused polycyclic aromatic compounds as light emitting organic compounds for forming an emission layer or the like. However, a compound having sufficiently satisfactory emission luminance and durability has hardly been obtained.

For example, bisanthracene derivatives (Japanese Patent Application Laid-Open No. 2000-344691) and chrysene derivatives (Japanese Patent Application Laid-Open No. 2004-75567 and Japanese Patent Application Laid-Open No. 2006-52323) have been disclosed as the fused polycyclic aromatic compounds. In particular, Japanese Patent Application Laid-Open No. 2006-52323 discloses that a bichrysene compound is used in the emission layer of an organic light emitting device, and describes specific compounds for a 5,5'-bichrysene compound and a 6,6'-bichrysene compound. In addition, the document describes merely unsubstituted bichrysenes such as 2,2'-bichrysene for nineteen kinds of isomers except the foregoing.

DISCLOSURE OF THE INVENTION

An object of the present invention is to provide a novel compound having sufficiently satisfactory emission luminance and sufficiently satisfactory durability, and more specifically, to provide a novel bichrysene compound. Another object of the present invention is to provide an organic light emitting device having high light emitting efficiency and excellent driving durability.

According to the present invention, there is provided a bichrysene compound represented by the following general formula (1):

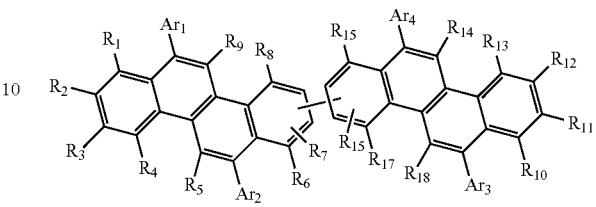

(1)

where $R_1$ to $R_{18}$ each independently represent a substituent selected from the group consisting of a hydrogen atom, a substituted or unsubstituted alkyl group, and a substituted or unsubstituted alkoxy group, and $Ar_1$ to $Ar_4$ each independently represent a substituted or unsubstituted hydrocarbon aromatic ring group.

According to the present invention, there can be provided a novel bichrysene compound having high chemical stability, a relatively deep Highest Occupied Molecular Orbital (HOMO), an energy gap of about 3.0 eV, a small dihedral angle, and good carrier transport property. In addition, there can be provided an organic light emitting device having the compound, the device having high light emitting efficiency and excellent driving durability.

Further features of the present invention will become apparent from the following description of exemplary embodiments with reference to the attached drawings.

BEST MODE FOR CARRYING OUT THE INVENTION

Figure 1:
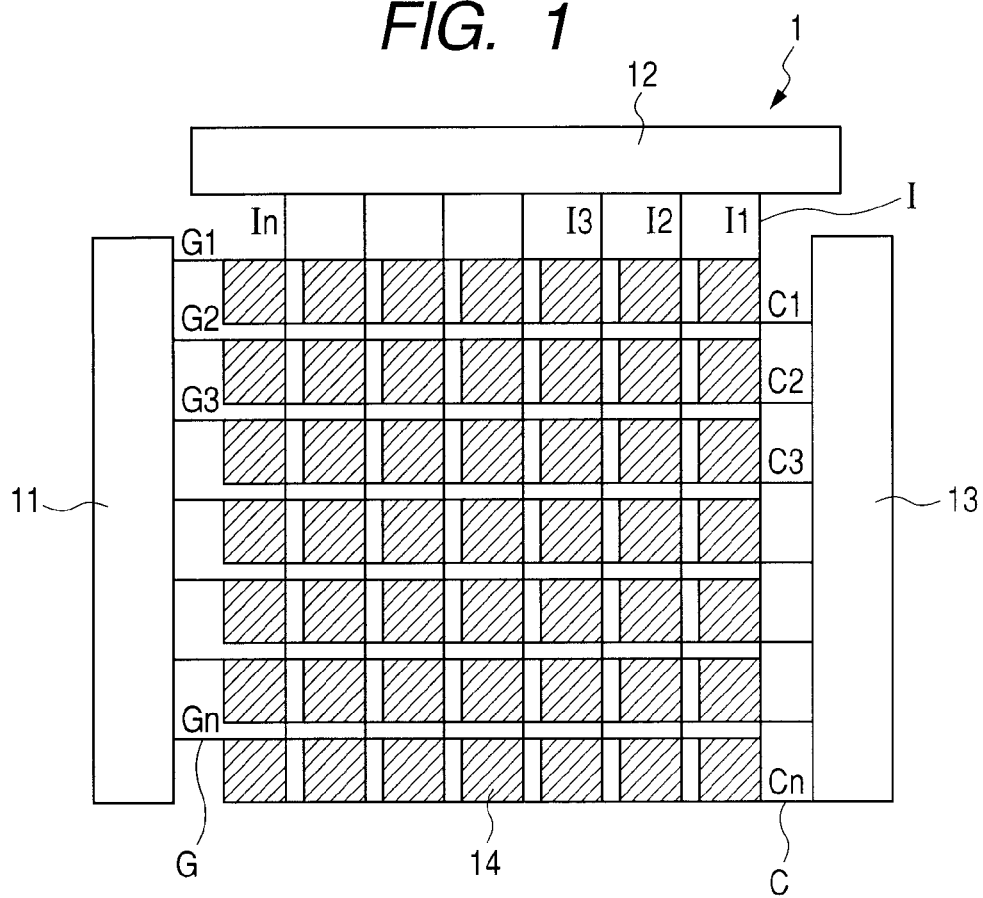
FIG. 1 is a view schematically illustrating an organic light emitting device according to an embodiment of the present invention and units for supplying electrical signals to the organic light emitting device.

A bichrysene compound of the present invention is represented by the following general formula (1).

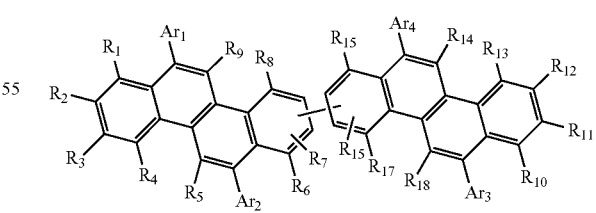

(1)

The bichrysene compound represented by the formula (1) is any one of a 2,2'-bichrysene compound in which chrysene rings are bonded to each other at their 2-positions, a 3,3'-bichrysene compound in which chrysene rings are bonded to each other at their 3-positions, and a 2,3'-bichrysene compound in which chrysene rings are bonded to each other at their 2- and 3-positions.

In the formula (1), $R_1$ to $R_{18}$ each independently represent a substituent selected from the group consisting of a hydrogen atom, a substituted or unsubstituted alkyl group, and a substituted or unsubstituted alkoxy group. Here, $R_7$ and $R_{16}$ each substitute for a carbon atom not used in the above-mentioned chrysene-chrysene bond out of the carbon atoms at the 2- and 3-positions of a chrysene ring.

Specific examples of the alkyl group represented by $R_1$ to $R_{18}$ include, but are of course not limited to, a methyl group, an ethyl group, an n-propyl group, an iso-propyl group, an n-butyl group, an iso-butyl group, a sec-butyl group, a tert-butyl group, an n-pentyl group, a neopentyl group, an n-hexyl group, an n-octyl group, an n-decyl group, an n-dodecyl group, a cyclopropyl group, a cyclobutyl group, a cyclopentyl group, a cyclohexyl group, a norbornyl group, and an adamantyl group.

Specific examples of the alkoxy group represented by $R_1$ to $R_{18}$ include, but are of course not limited to, a methoxy group, an ethoxy group, an iso-propoxy group, a tert-butoxy group, an aryloxy group, and a benzyloxy group.

Examples of the substituent which the above-mentioned alkyl group and alkoxy group may further have include, but are of course not limited to: alkyl groups such as a methyl group, an ethyl group, and a propyl group; hydrocarbon aromatic ring groups such as a phenyl group, a naphthyl group, a phenanthryl group, and a fluorenyl group; heteroaromatic ring groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; alkoxy groups such as a methoxy group and an ethoxy group; aryloxy groups such as a phenoxy group and a naphthoxy group; halogen atoms such as fluorine, chlorine, bromine, and iodine; a hydroxyl group; a cyano group; and a nitro group.

In the formula (1), $Ar_1$ to $Ar_4$ each represent a substituted or unsubstituted hydrocarbon aromatic ring group.

Specific examples of the hydrocarbon aromatic ring group represented by $Ar_1$ to $Ar_4$ include, but are of course not limited to, a phenyl group, a naphthyl group, a phenanthryl group, a fluorenyl group, an anthracenyl group, a chrysenyl group, a pyrenyl group, a perylenyl group, an indenyl group, an acenaphthylenyl group, an acenaphthenyl group, a biphenylenyl group, a fluoranthenyl group, a benzofluoranthenyl group, a triphenylenyl group, and a naphthacenyl group.

Examples of the substituent which the above-mentioned hydrocarbon aromatic ring group may further have include, but are of course not limited to: alkyl groups such as a methyl group, an ethyl group, an iso-propyl group, a tert-butyl group, an n-hexyl group, and a cyclohexyl group; hydrocarbon aromatic ring groups such as a phenyl group, a tolyl group, a tert-butylphenyl group, a xylyl group, a mesityl group, a naphthyl group, a phenanthryl group, a fluorenyl group, a 9,9-dimethylfluorenyl group, a 9,9-diethylfluorenyl group, and a 9,9-di-(n-hexyl)fluorenyl group; heteroaromatic ring groups such as a thienyl group, a pyrrolyl group, a pyridyl group, and a phenanthrolinyl group; substituted amino groups such as a dimethylamino group, a diethylamino group, a dibenzylamino group, a diphenylamino group, a ditolylamino group, and a dianisolylamino group; alkoxy groups such as a methoxy group and an ethoxy group; aryloxy groups such as a phenoxy group and a naphthoxy group; halogen atoms such as fluorine, chlorine, bromine, and iodine; a hydroxyl group; a cyano group; and a nitro group.

In addition, all or part of the hydrogen atoms present at the main skeleton or substituents in the bichrysene compound represented by the formula (1) may each be replaced with deuterium.

The bichrysene compound represented by the formula (1) is preferably a compound represented by any one of the following formulae (2) to (4).

(2)

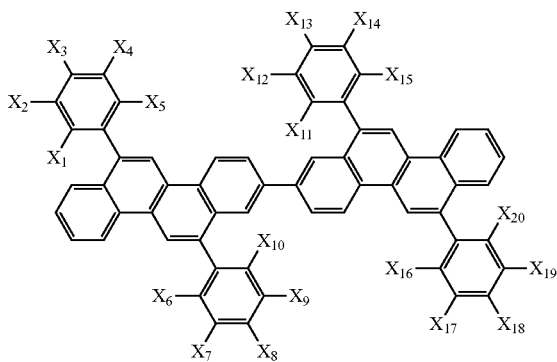

(3)

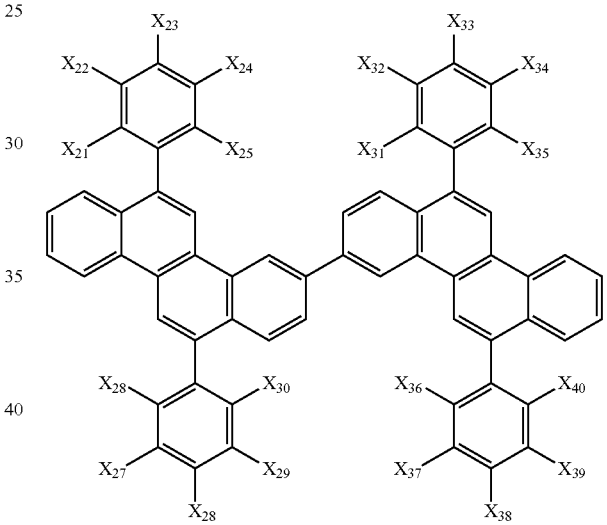

(4)

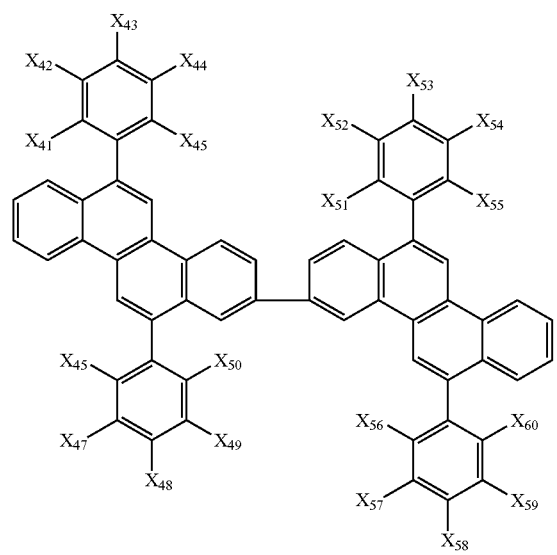

In the formulae (2) to (4), $X_1$ to $X_{60}$ each independently represent a substituent selected from the group consisting of a hydrogen atom, a substituted or unsubstituted alkyl group, a substituted or unsubstituted alkoxy group, and a substituted or unsubstituted hydrocarbon aromatic ring group.

Specific examples of the alkyl group represented by any one of $X_1$ to $X_{60}$ are identical to those of the alkyl group represented by any one of $R_1$ to $R_{18}$ in the formula (1). A substituent which the alkyl group may further have is identical to a substituent which, when any one of $R_1$ to $R_{18}$ in the formula (1) represents an alkyl group, the alkyl group may further have.

Specific examples of the alkoxy group represented by any one of $X_1$ to $X_{60}$ are identical to those of the alkoxy group represented by any one of $R_1$ to $R_{18}$ in the formula (1). A substituent which the alkoxy group may further have is identical to a substituent which, when any one of $R_1$ to $R_{18}$ in the formula (1) represents an alkoxy group, the alkoxy group may further have.

Specific examples of the hydrocarbon aromatic ring group represented by any one of $X_1$ to $X_{60}$ are identical to those of the hydrocarbon aromatic ring group represented by any one of $Ar_1$ to $Ar_4$ in the formula (1). A substituent which the hydrocarbon aromatic ring group may further have is identical to a substituent which the hydrocarbon aromatic ring group represented by any one of $Ar_1$ to $Ar_4$ in the formula (1) may further have.

Next, methods of synthesizing the 2,2'-bichrysene compound, the 3,3'-bichrysene compound, and the 2,3'-bichrysene compound each serving as the bichrysene compound of the present invention are described.

The bichrysene compound of the present invention can be synthesized by any one of the Suzuki-Miyaura coupling reactions represented by the following formulae (5) to (8), that is, the Suzuki-Miyaura coupling reactions each using a 2-Cl intermediate or 3-Cl intermediate as a halogen compound, a 2-Bpin intermediate or 3-Bpin intermediate as a boronic acid pinacol ester, and a palladium catalyst.

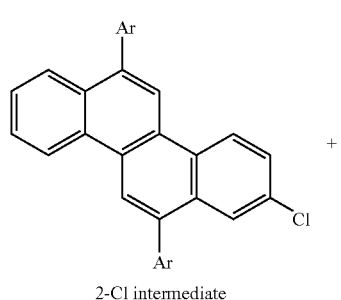

(5)

2-Cl intermediate

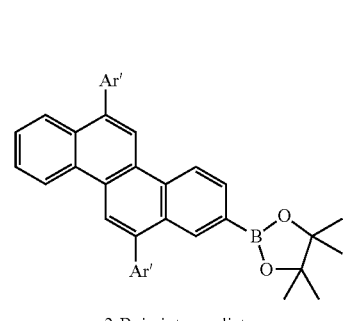

2-Bpin intermediate

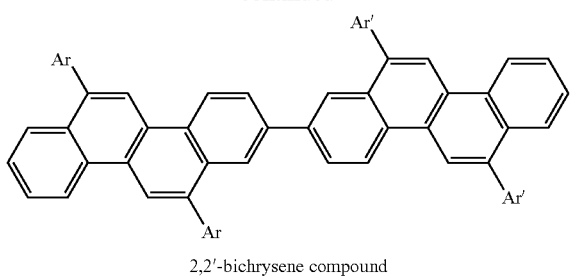

2,2'-bichrysene compound (In the formula, Ar and Ar' each represent a substituted or unsubstituted hydrocarbon aromatic ring group.)

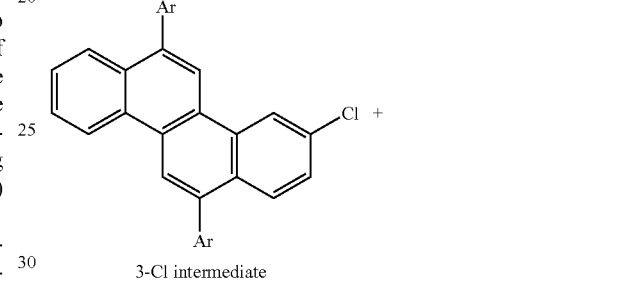

3-Cl intermediate (6)

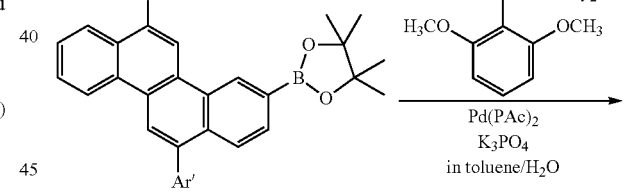

3-Bpin intermediate

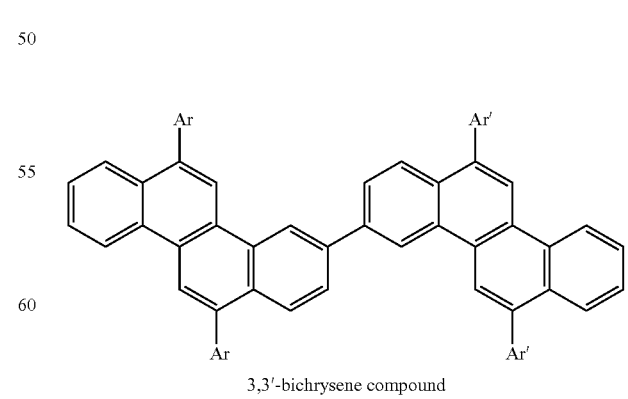

3,3'-bichrysene compound (In the formula, Ar and Ar' each represent a substituted or unsubstituted hydrocarbon aromatic ring group.)

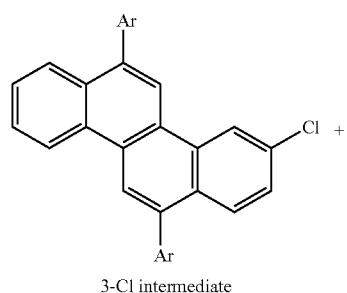

3-Cl intermediate

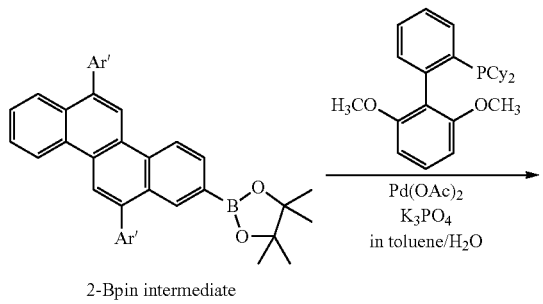

2-Bpin intermediate

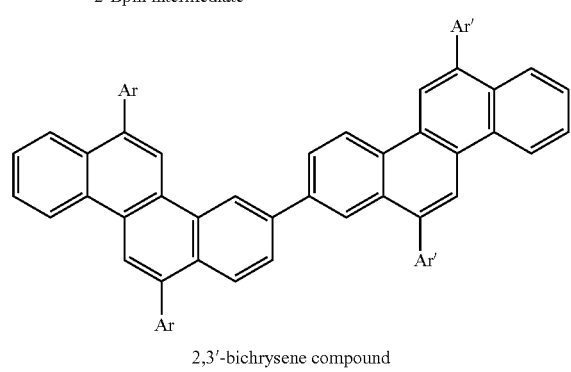

2,3′-bichrysene compound (In the formula, Ar and Ar' each represent a substituted or unsubstituted hydrocarbon aromatic ring group.)

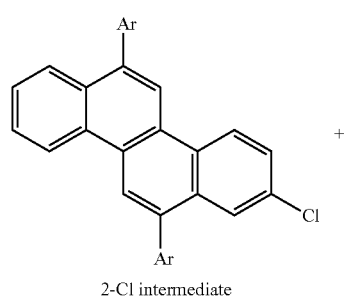

2-Cl intermediate

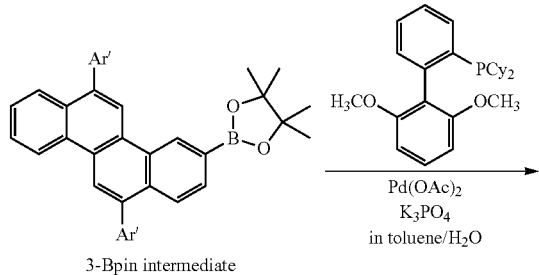

3-Bpin intermediate (7)

(8)

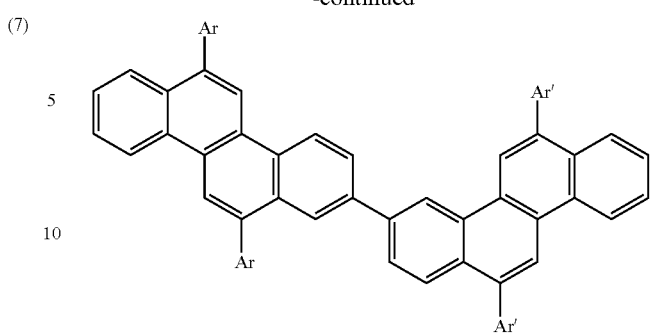

2,3′-bichrysene compound (In the formula, Ar and Ar' each represent a substituted or unsubstituted hydrocarbon aromatic ring group.)

The 2-Cl intermediate and the 2-Bpin intermediate as precursors are synthesized according to a synthesis route represented by the following formula (9) via 6,12-dibromo-2-chlorochrysene.

(9)

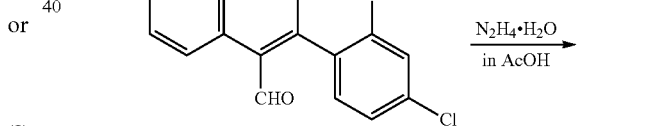

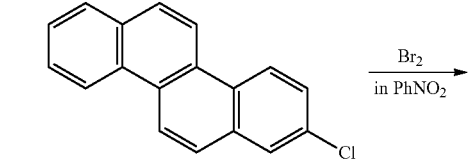

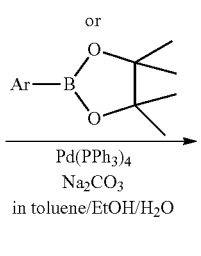

-continued

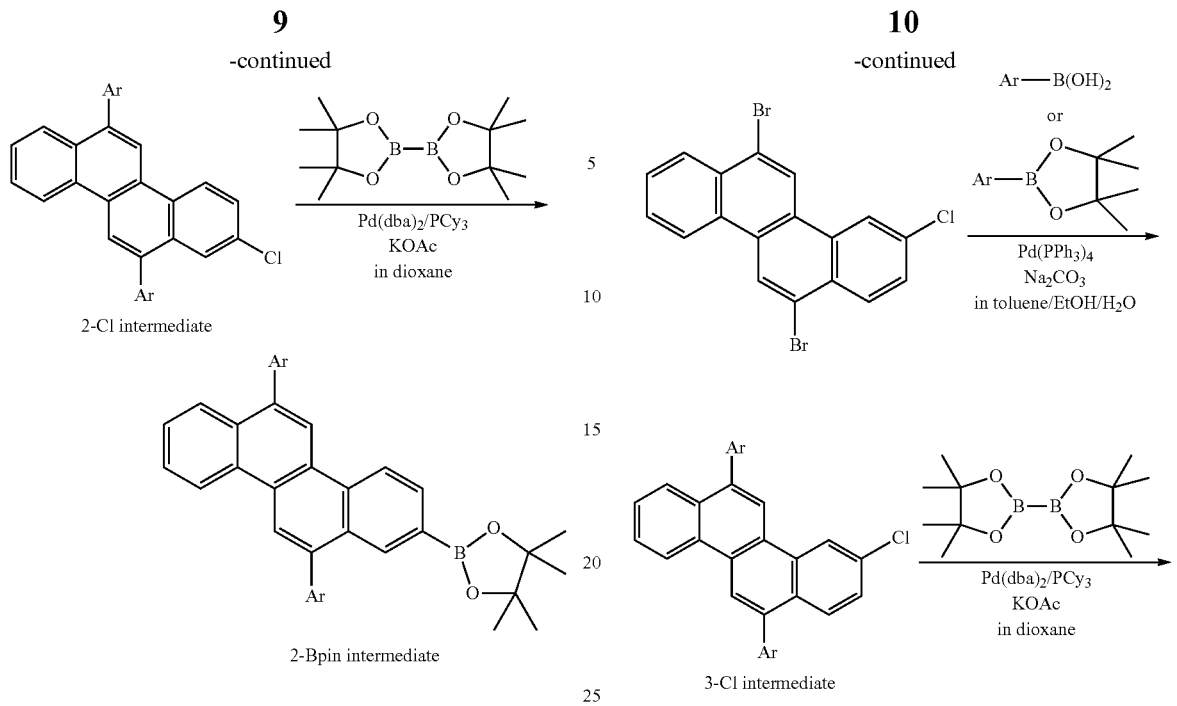

(In the formula, Ar represents a substituted or unsubstituted hydrocarbon aromatic ring group.)

Similarly, the 3-Cl intermediate and the 3-Bpin intermediate as precursors are synthesized according to a synthesis route represented by the following formula (10) via 6,12-dibromo-3-chlorochrysene.

(10)

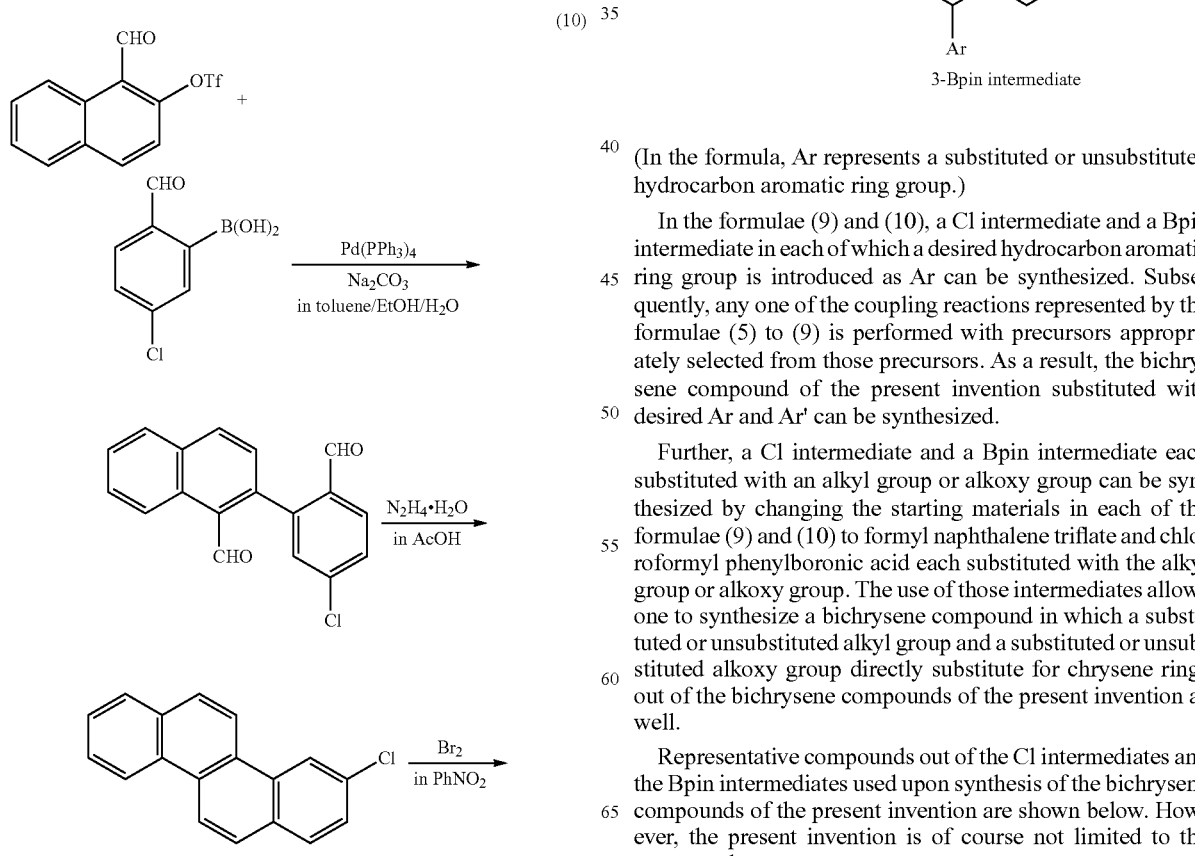

(In the formula, Ar represents a substituted or unsubstituted hydrocarbon aromatic ring group.)

In the formulae (9) and (10), a Cl intermediate and a Bpin intermediate in each of which a desired hydrocarbon aromatic ring group is introduced as Ar can be synthesized. Subsequently, any one of the coupling reactions represented by the formulae (5) to (9) is performed with precursors appropriately selected from those precursors. As a result, the bichrysene compound of the present invention substituted with desired Ar and Ar' can be synthesized.

Further, a Cl intermediate and a Bpin intermediate each substituted with an alkyl group or alkoxy group can be synthesized by changing the starting materials in each of the formulae (9) and (10) to formyl naphthalene triflate and chloroformyl phenylboronic acid each substituted with the alkyl group or alkoxy group. The use of those intermediates allows one to synthesize a bichrysene compound in which a substituted or unsubstituted alkyl group and a substituted or unsubstituted alkoxy group directly substitute for chrysene rings out of the bichrysene compounds of the present invention as well.

Representative compounds out of the Cl intermediates and the Bpin intermediates used upon synthesis of the bichrysene compounds of the present invention are shown below. However, the present invention is of course not limited to the compounds.

(2-Cl intermediates)
Cl-201
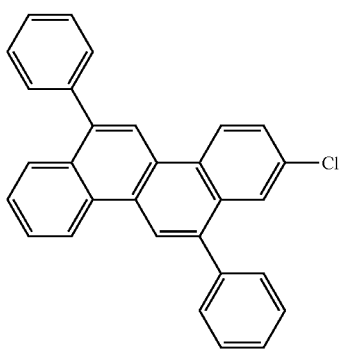
Cl-202
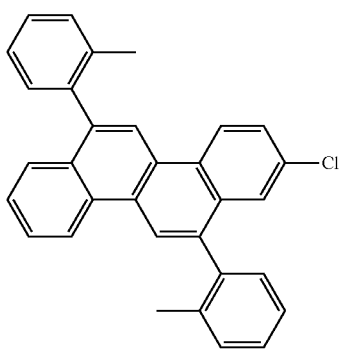
Cl-203
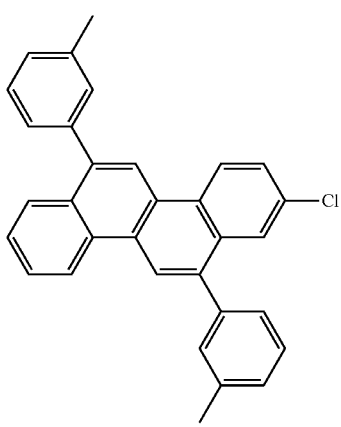
Cl-204
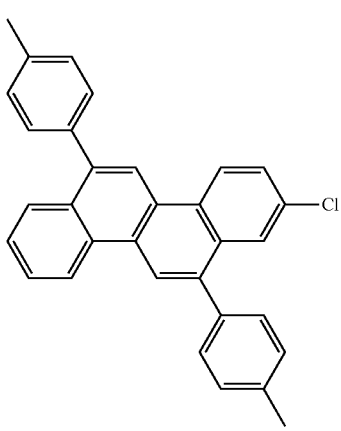
Cl-205
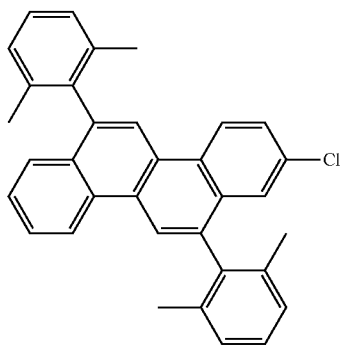
Cl-206
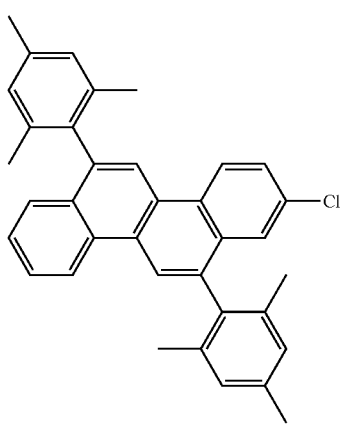
Cl-207
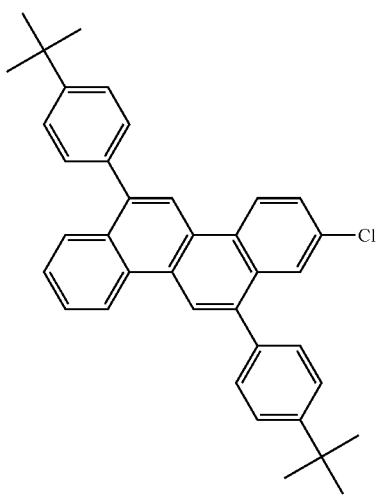

Cl-208
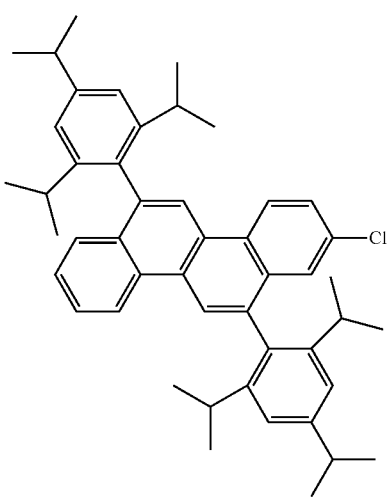
Cl-209
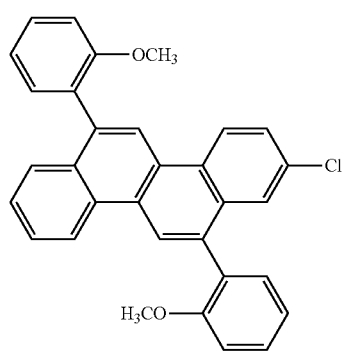
Cl-210
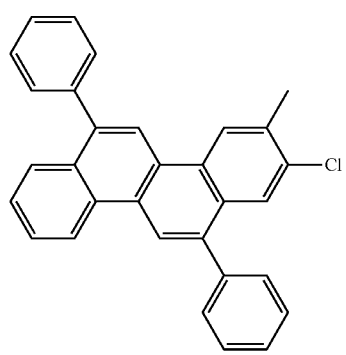
Cl-211
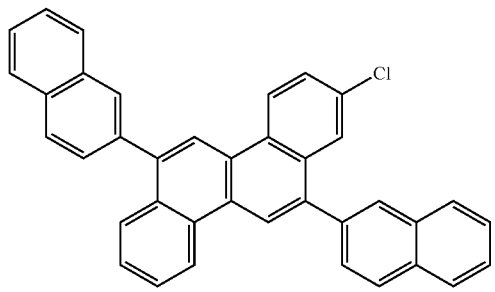
Cl-212
Cl-213
(3-Cl intermediates)
Cl-301
Cl-302
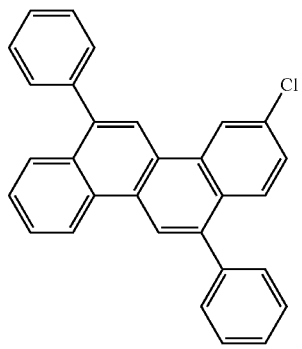
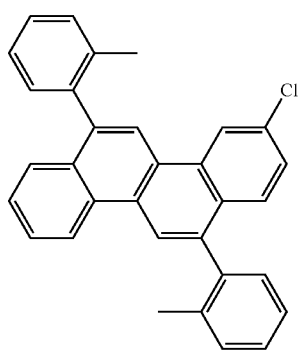

Cl-303
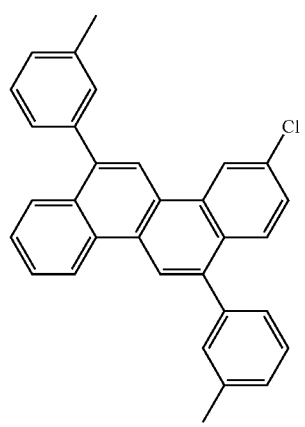
Cl-304
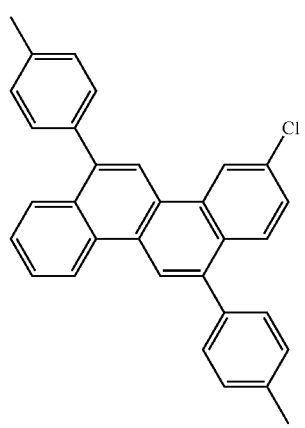
Cl-305
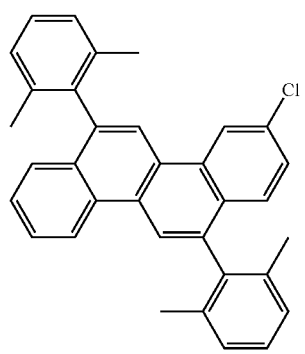
Cl-306
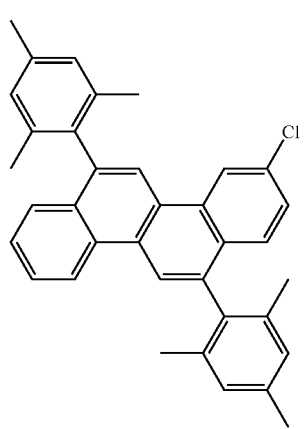
Cl-307
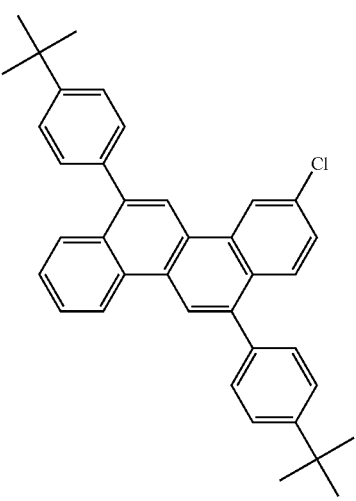
Cl-308
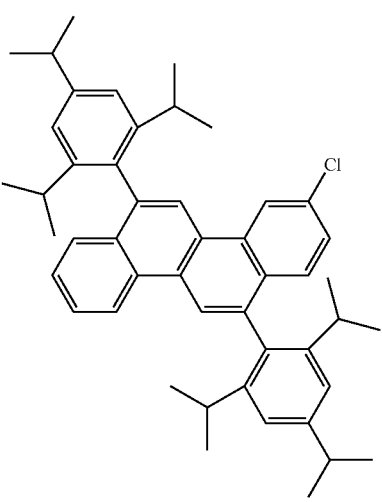
Cl-309
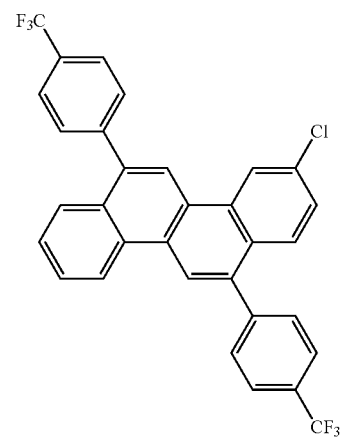

-continued
Cl-310
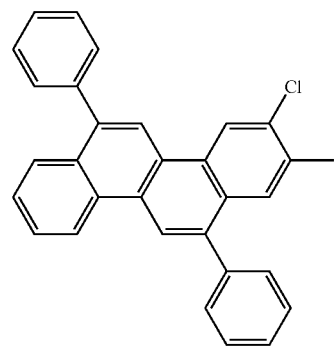
Cl-311
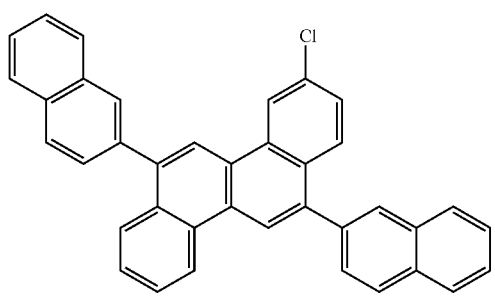
Cl-312
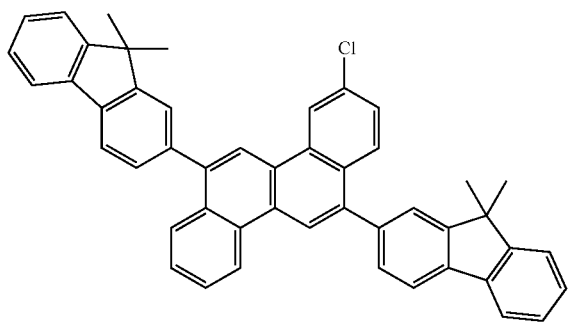
Cl-313
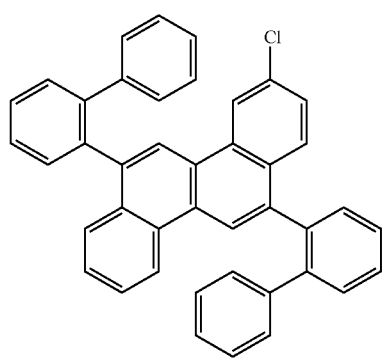
-continued
(2-Bpin intermediates)
Bpin-201
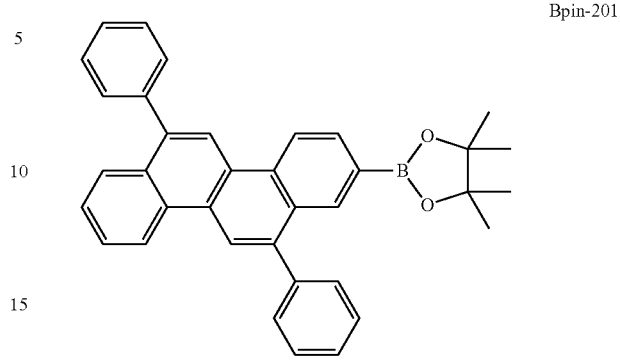
Bpin-202
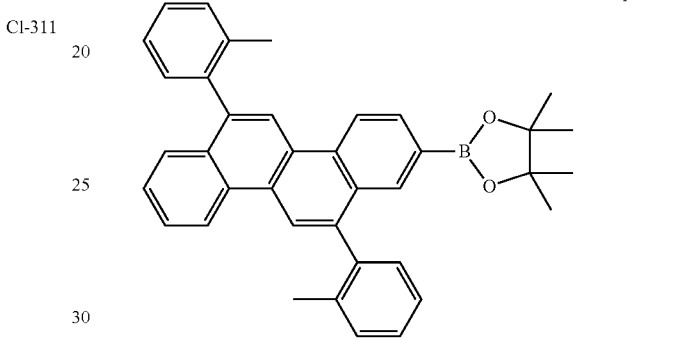
Bpin-203
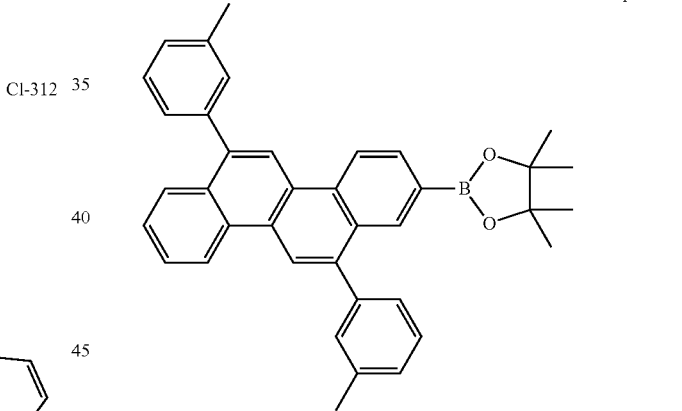
Bpin-204
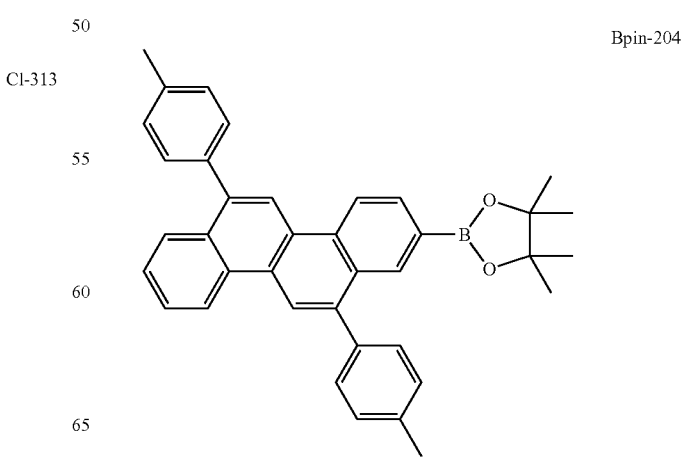

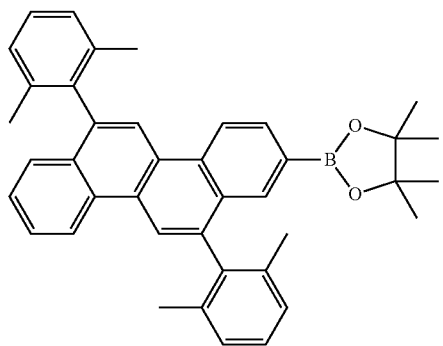
Bpin-205
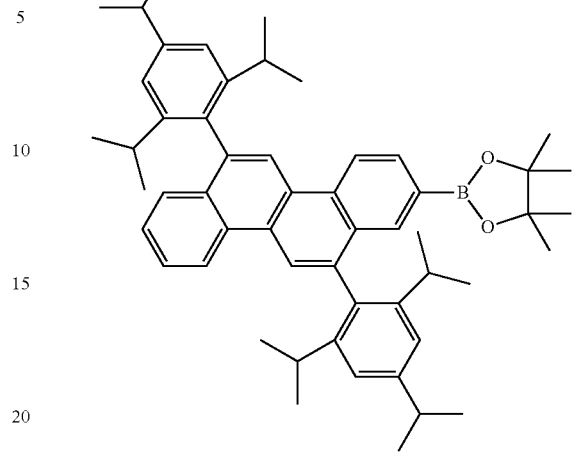
Bpin-208
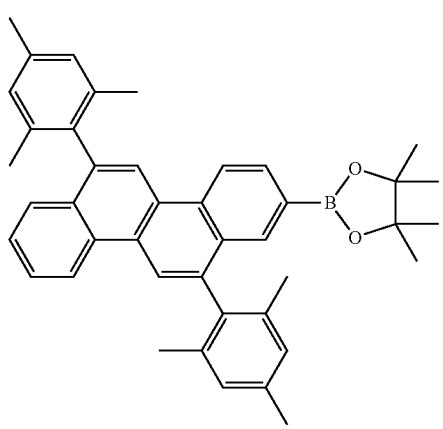
Bpin-206
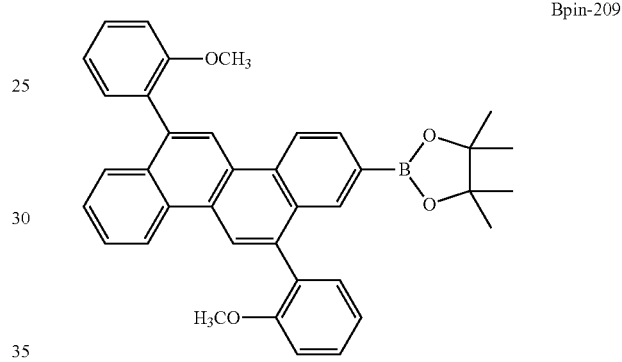
Bpin-209
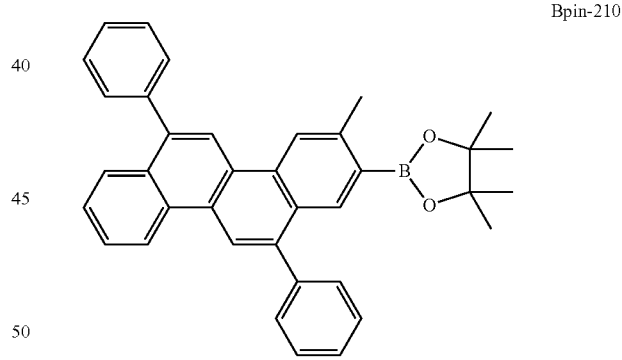
Bpin-210
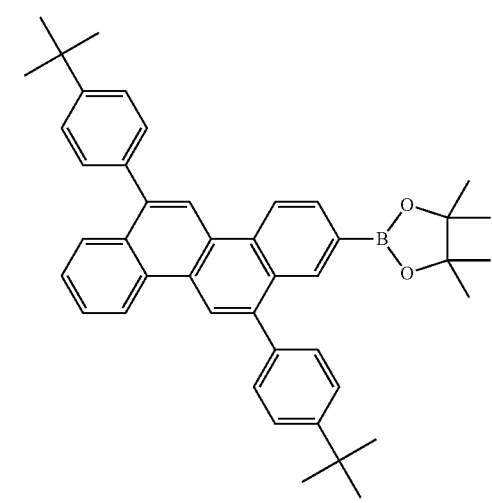
Bpin-207
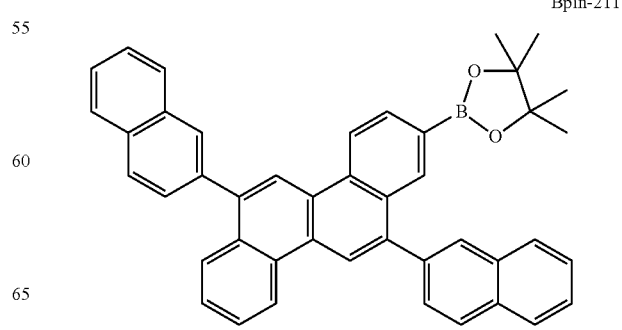
Bpin-211

Bpin-212
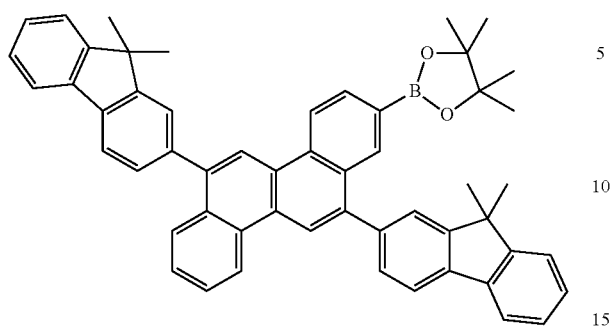
Bpin-302
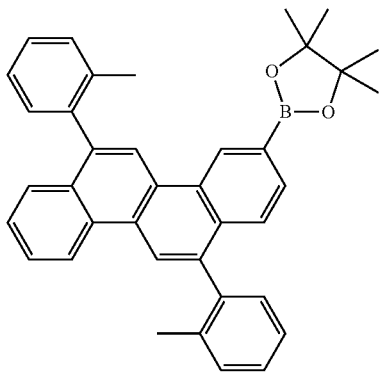
Bpin-213
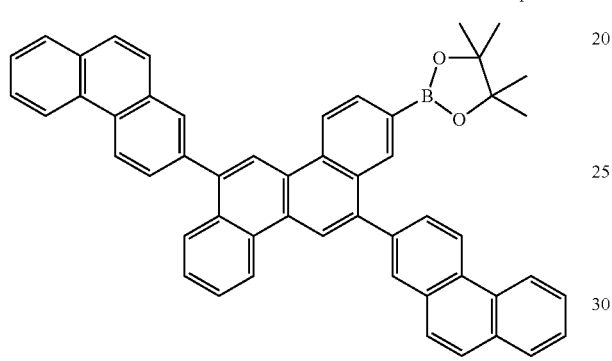
Bpin-303
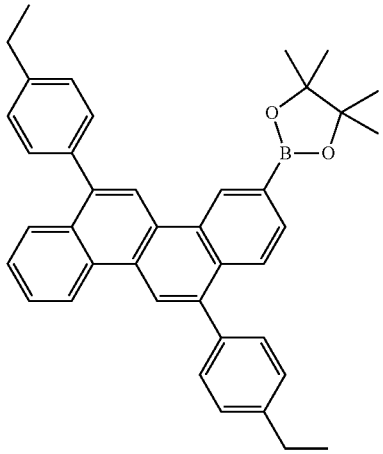
Bpin-214
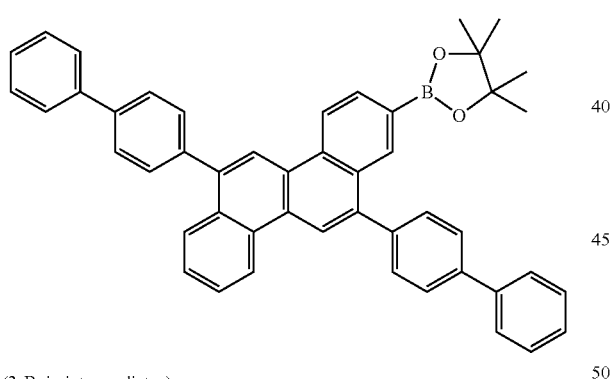
Bpin-304
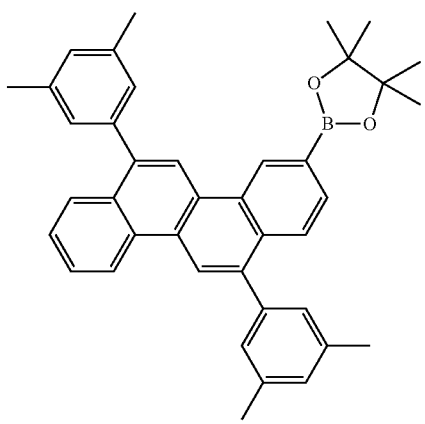
(3-Bpin intermediates)
Bpin-301
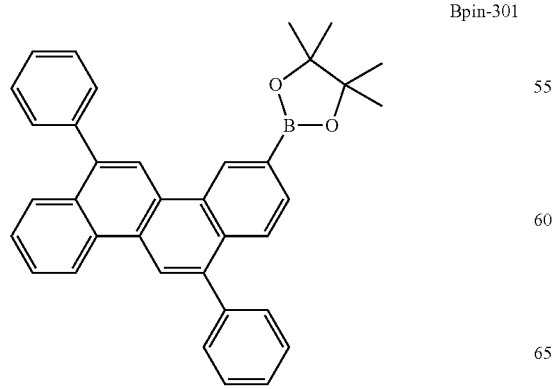
Bpin-305
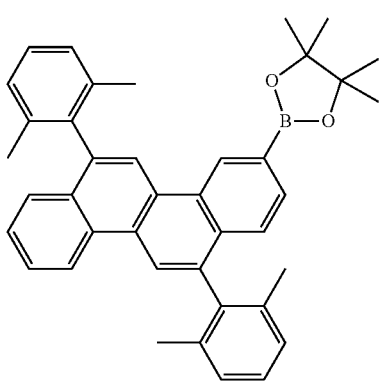

Bpin-306
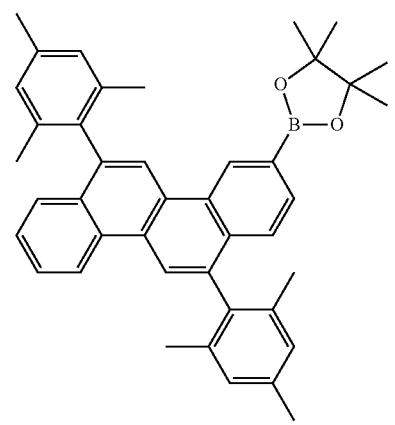
Bpin-307
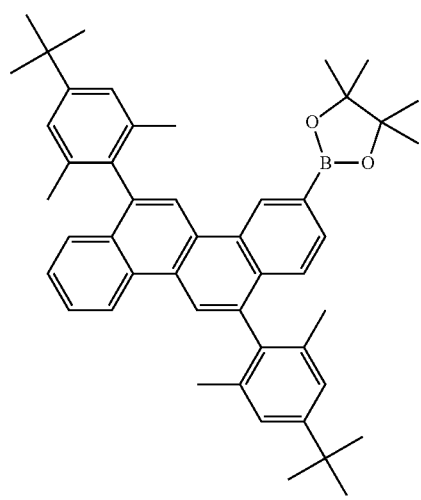
Bpin-308
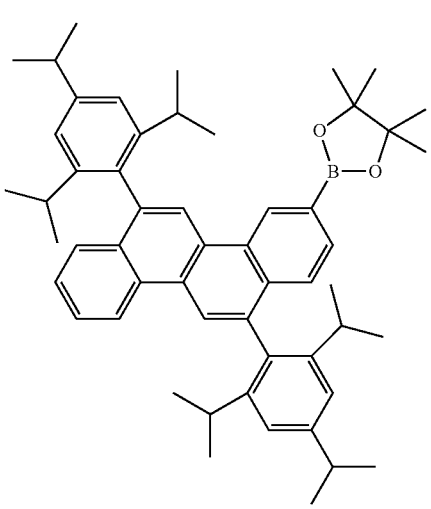
Bpin-309
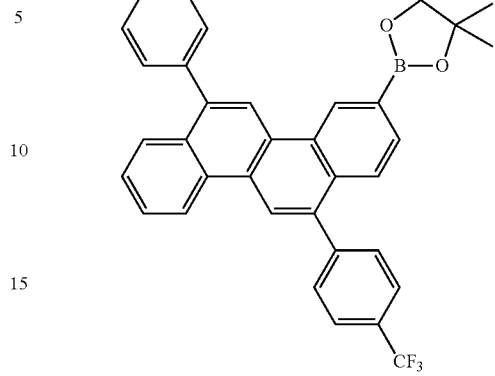
Bpin-310
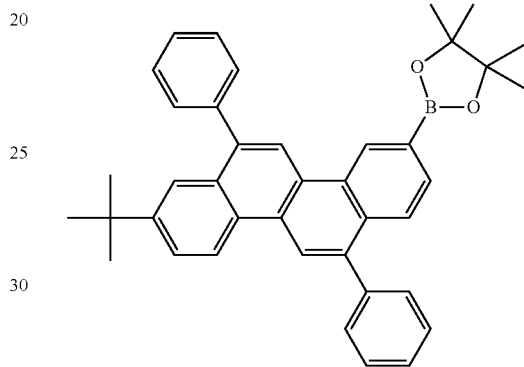
Bpin-311
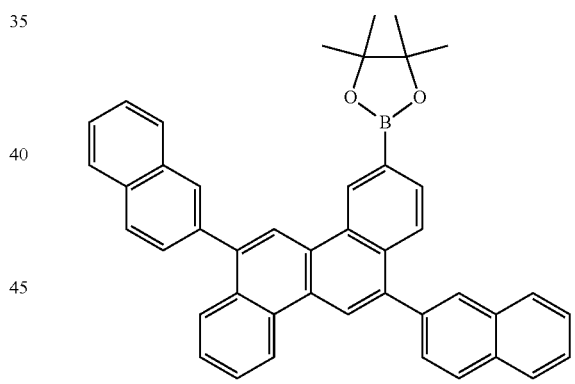
Bpin-312
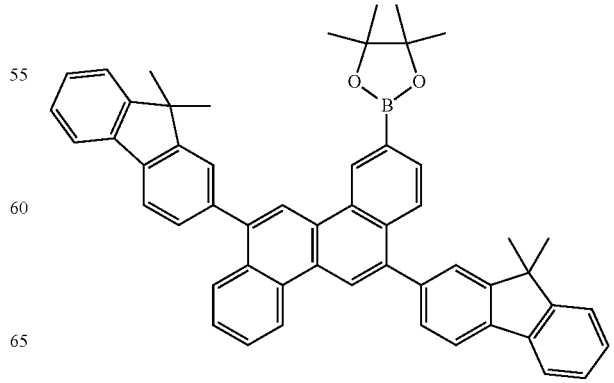

Bpin-313
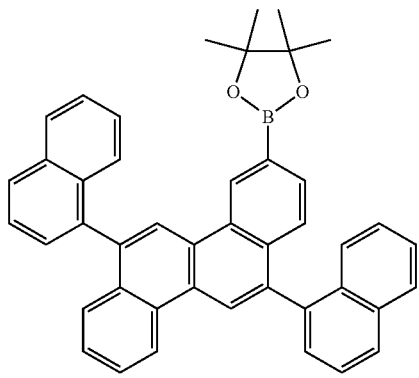
Bpin-314
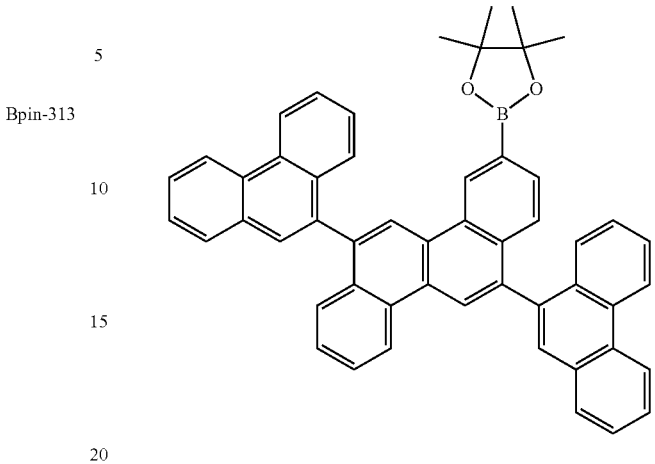
The bichrysene compounds of the present invention can be synthesized by performing the reactions represented by the formulae (5) to (8) with the intermediates shown above.
Hereinafter, specific structural formulae of the bichrysene compound of the present invention are shown. However, the present invention is of course not limited to the formulae.
C101
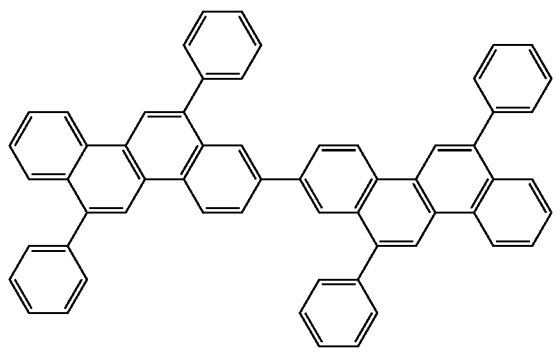
C102
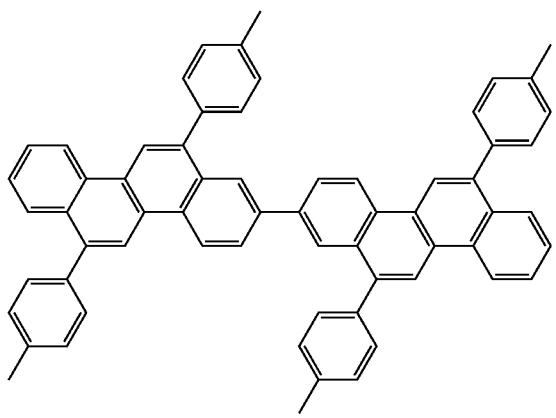
C103
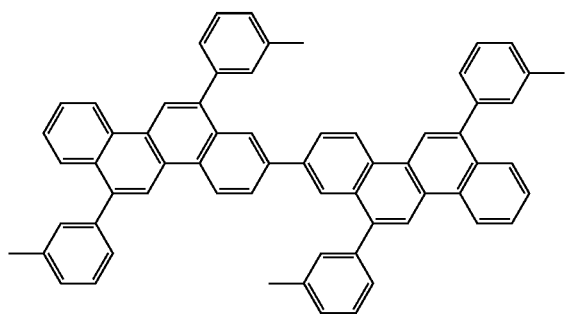
C104
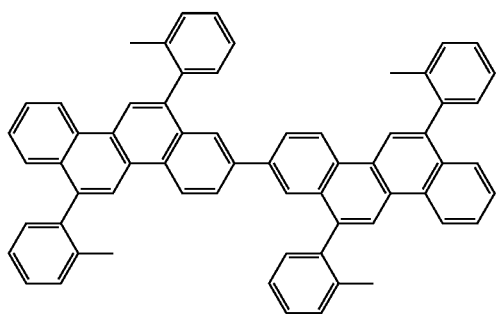

-continued
C105
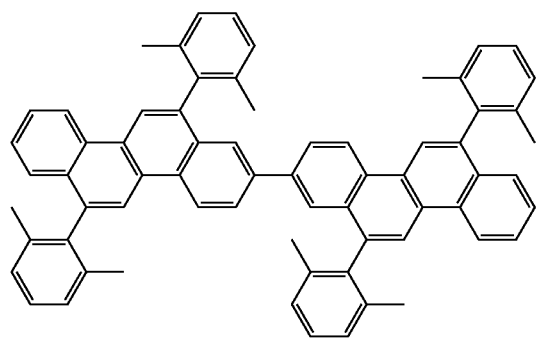
C106
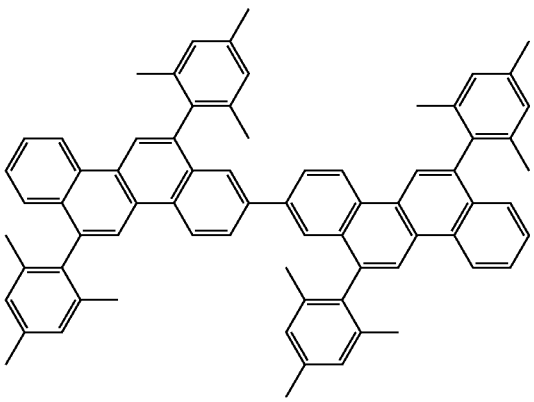
C107
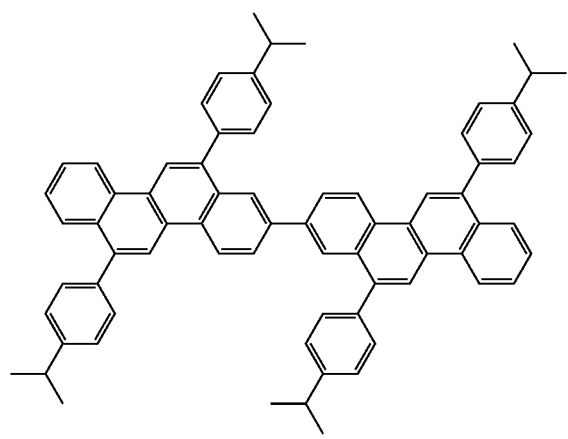
C108
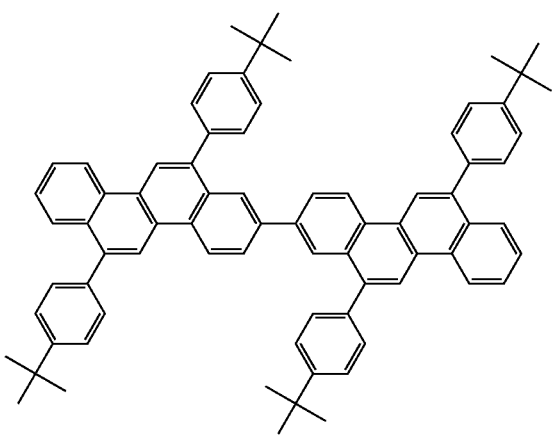
C-109
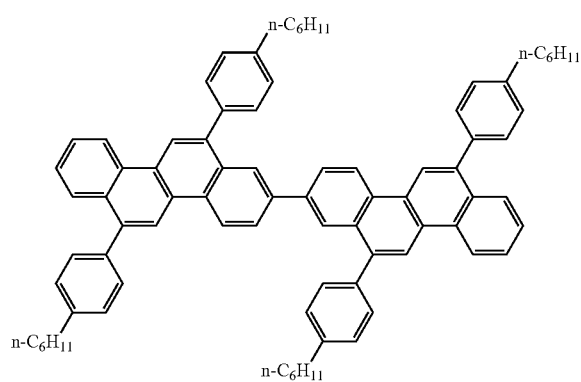
C-110
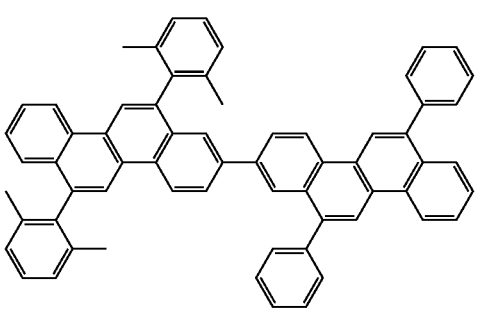

-continued
C111
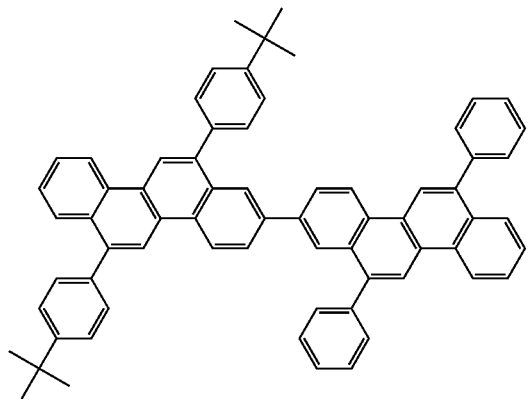
C112
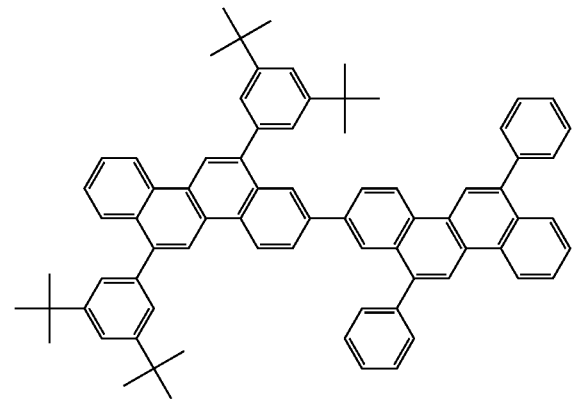
C113
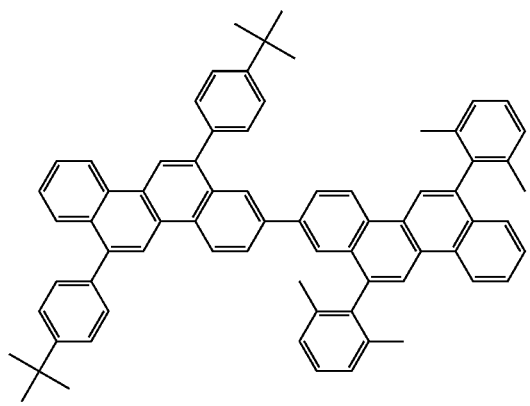
C114
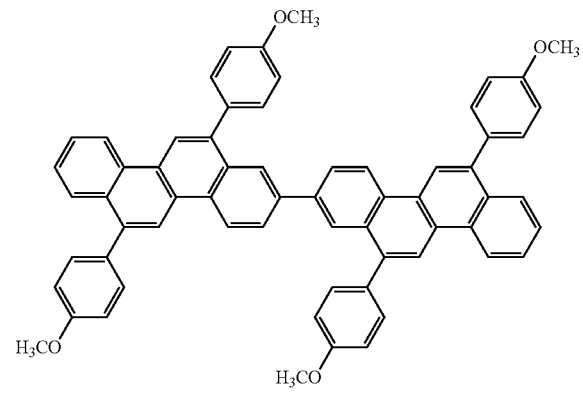
C115
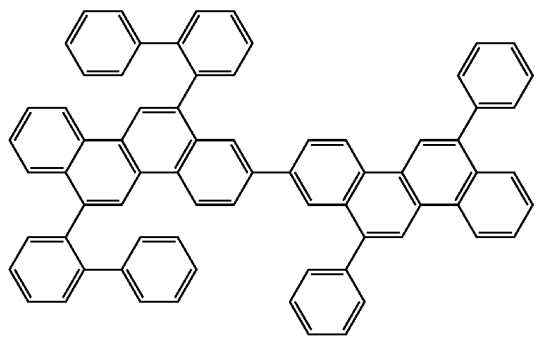
C116
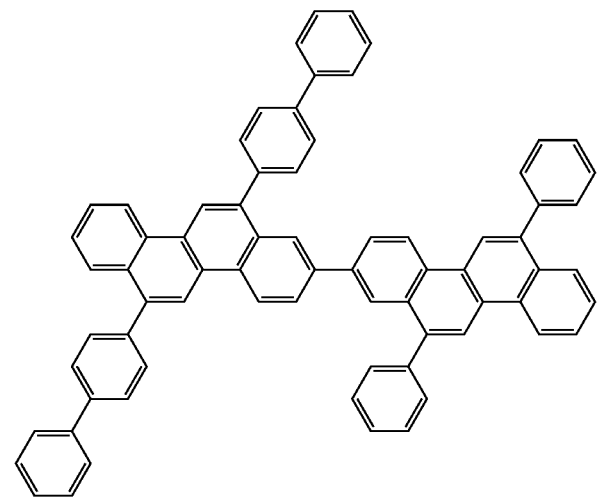

-continued
C117
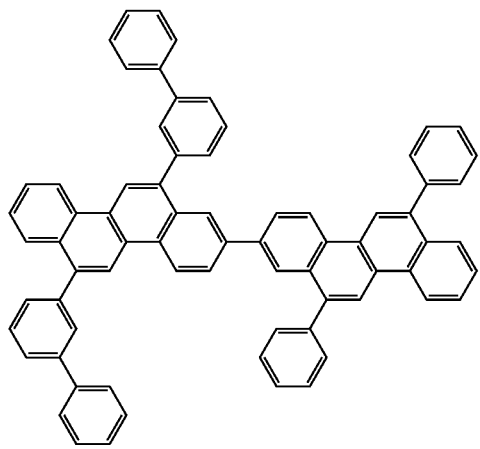
C118
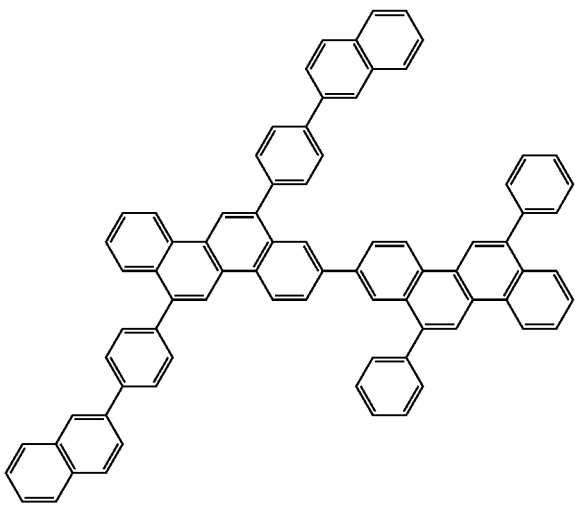
C201
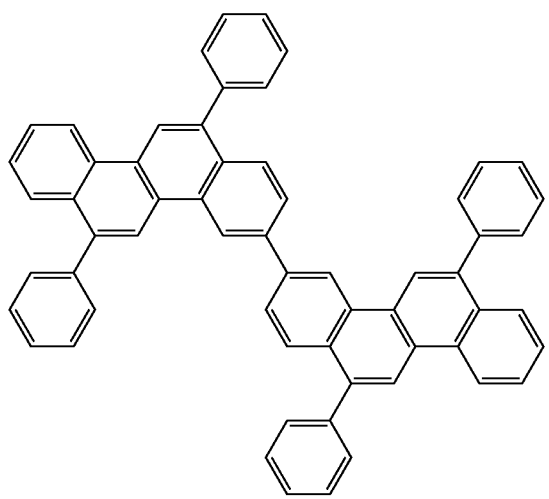
C202
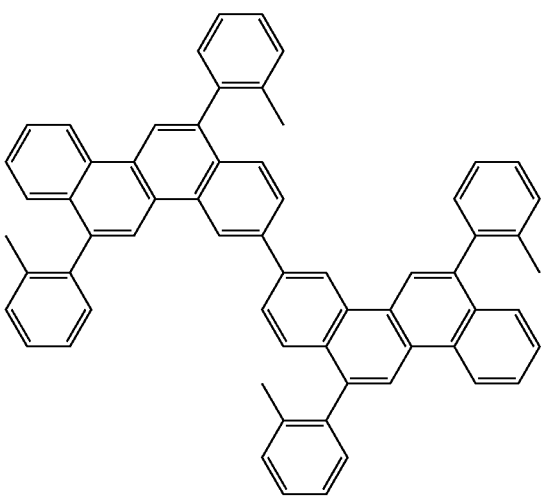
C203
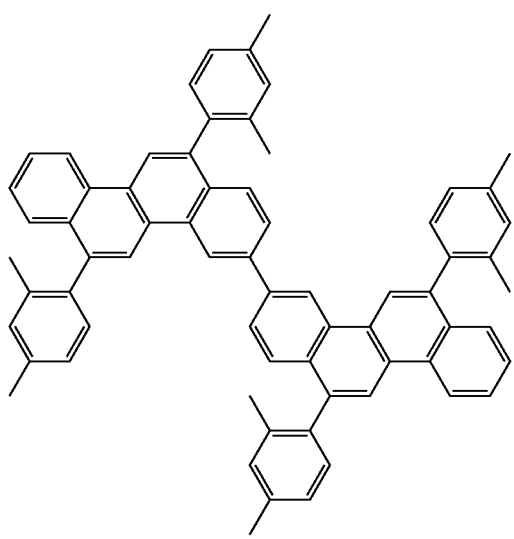
C204
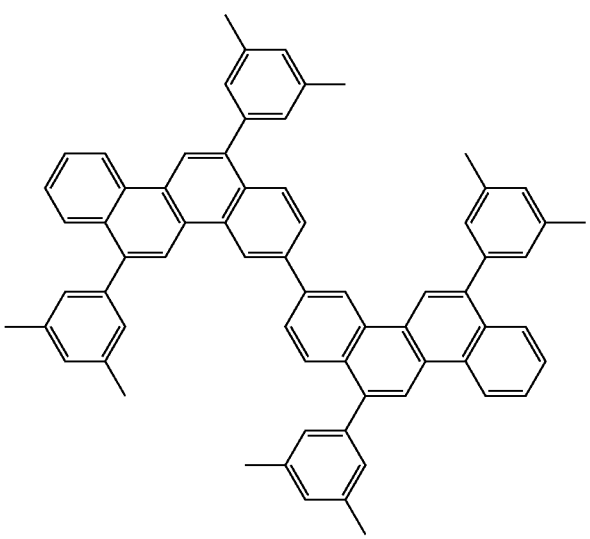

-continued
C205
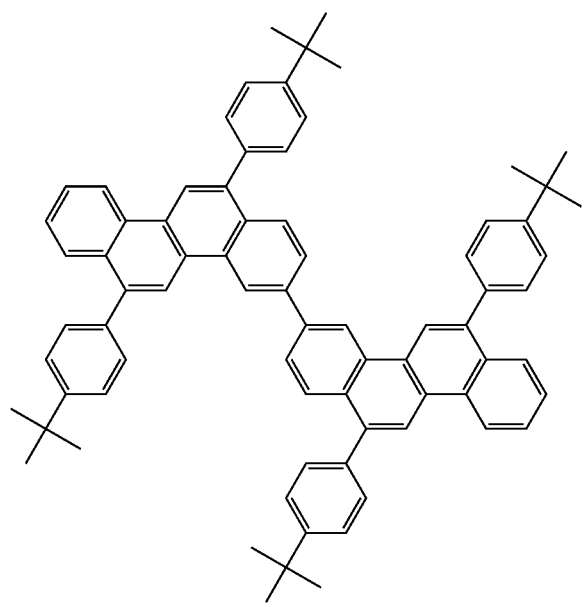
C206
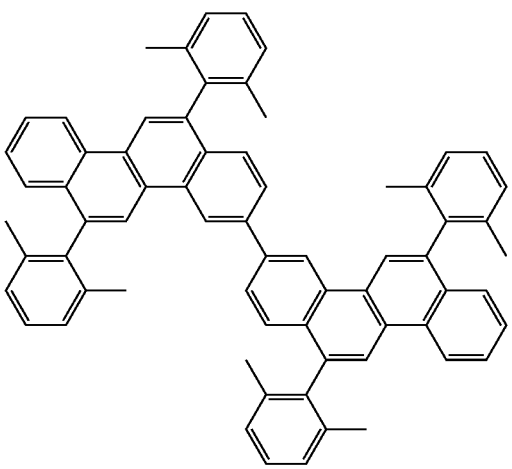
C207
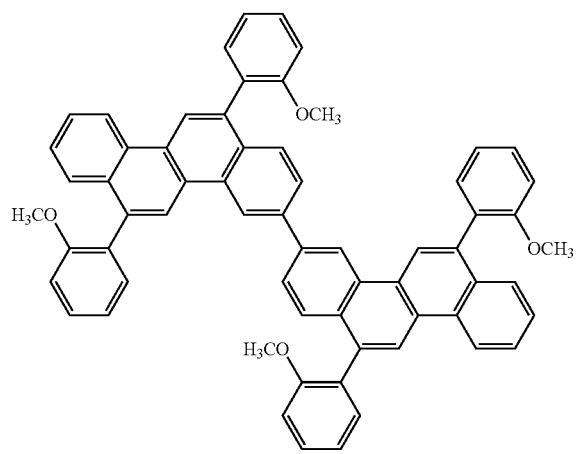
C208
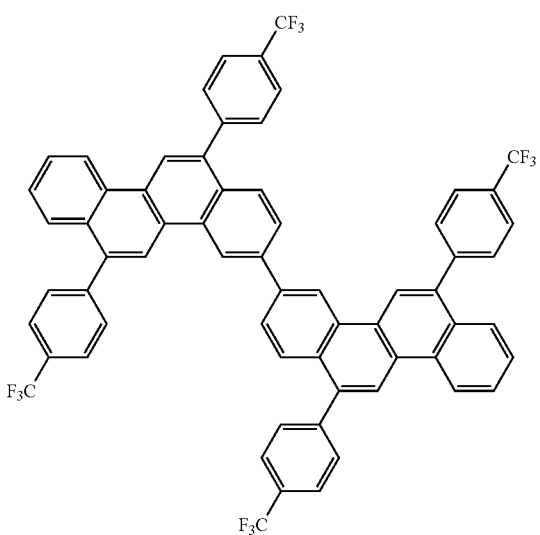

-continued
C209
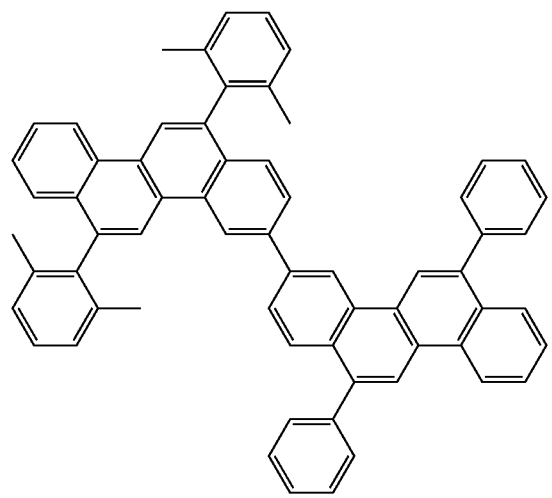
C210
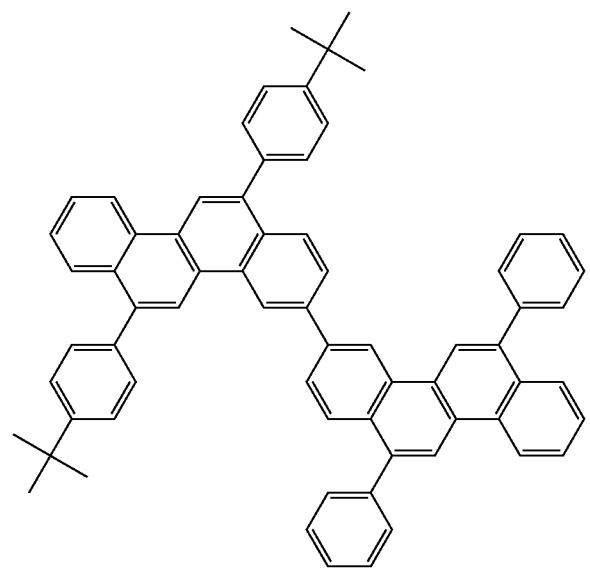
C211
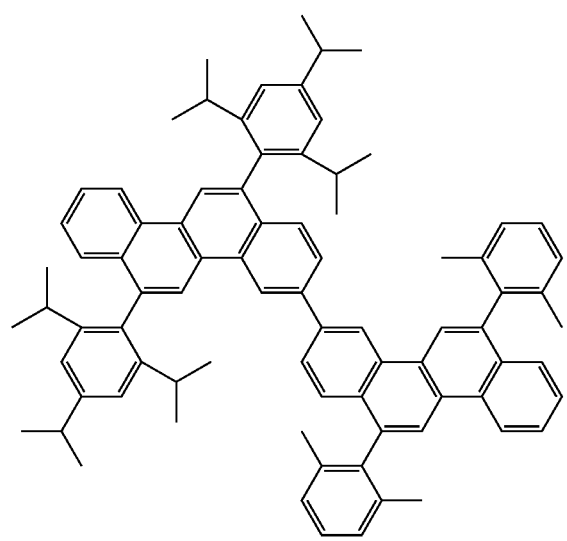
C212
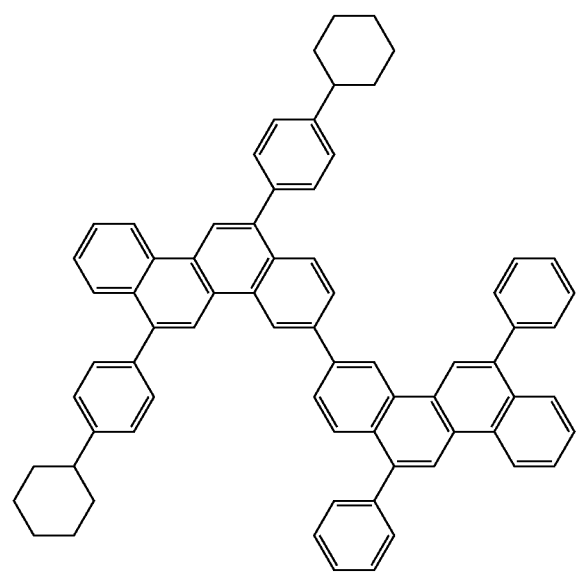

-continued
C213
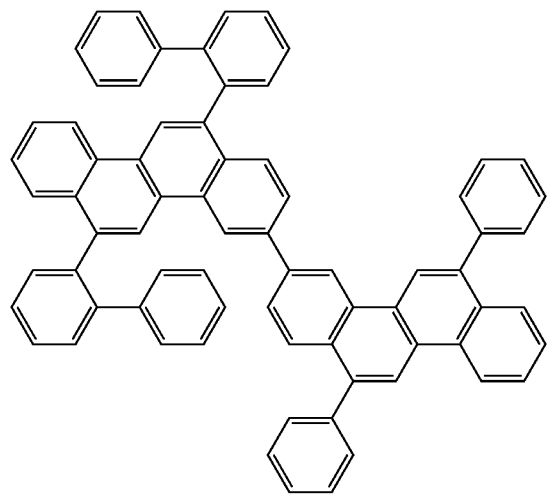
C214
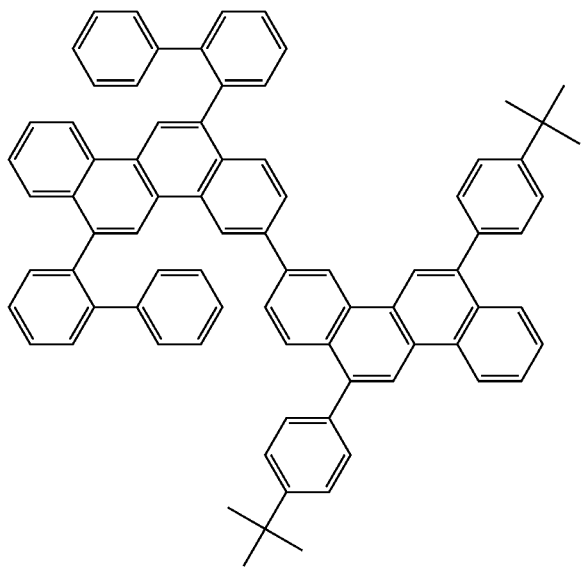
C215
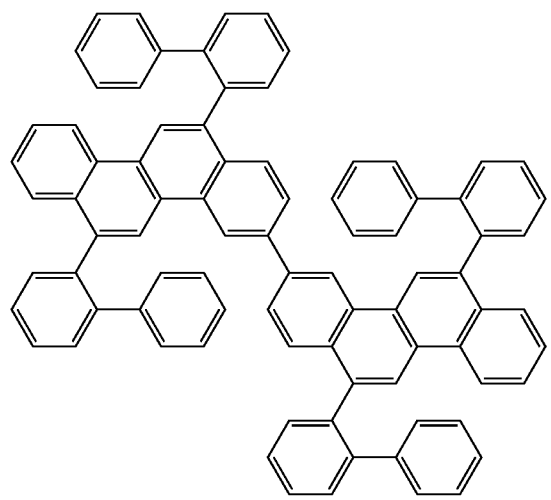
C301
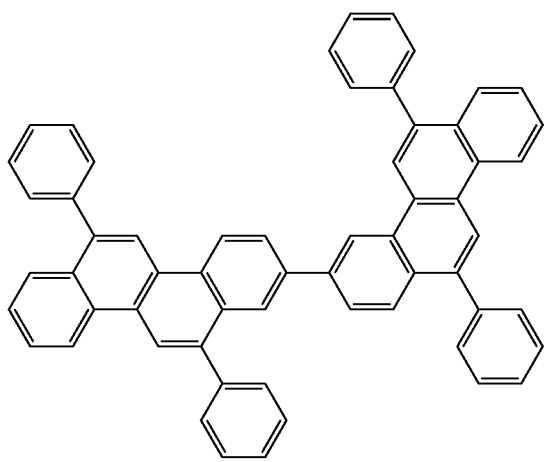
C302
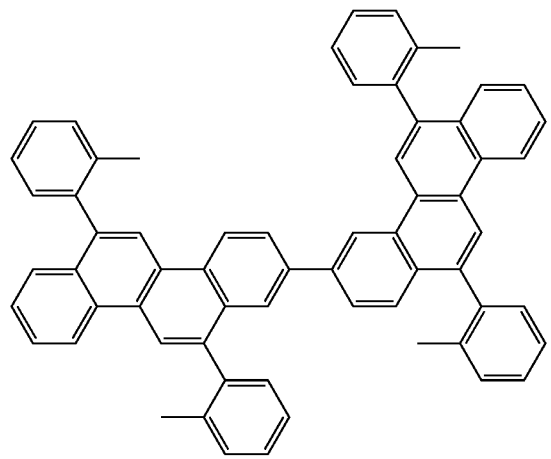
C303
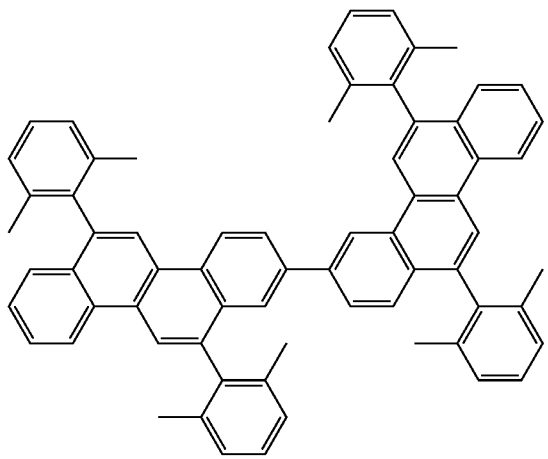

-continued
C304
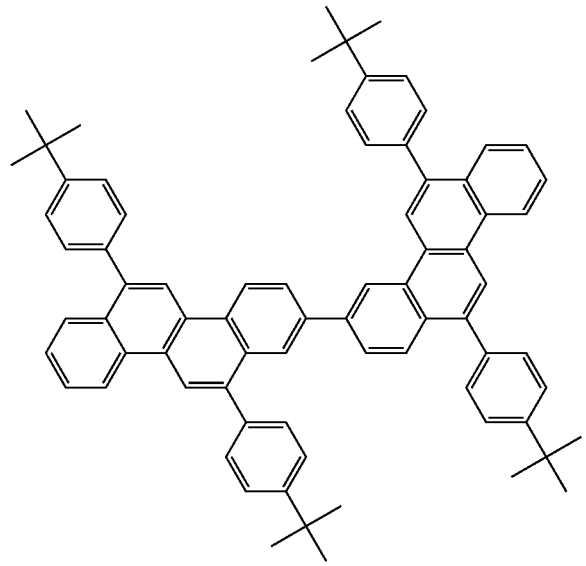
C305
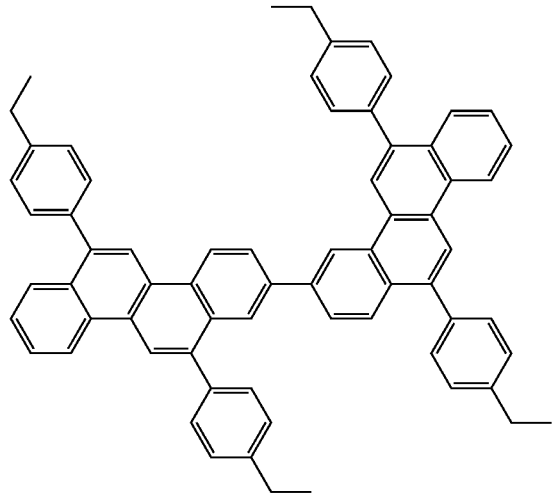
C306
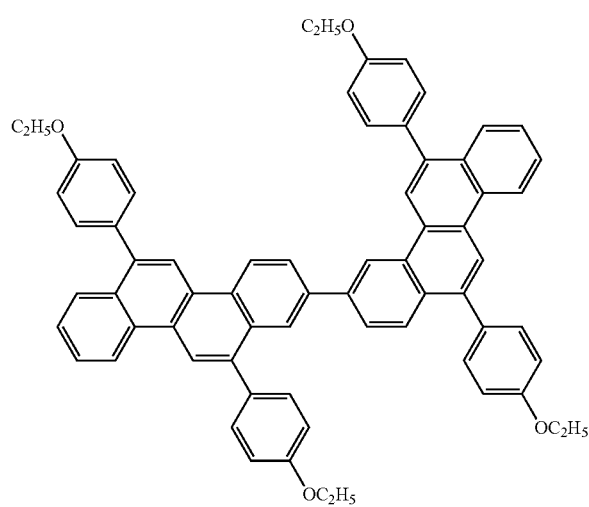
C307
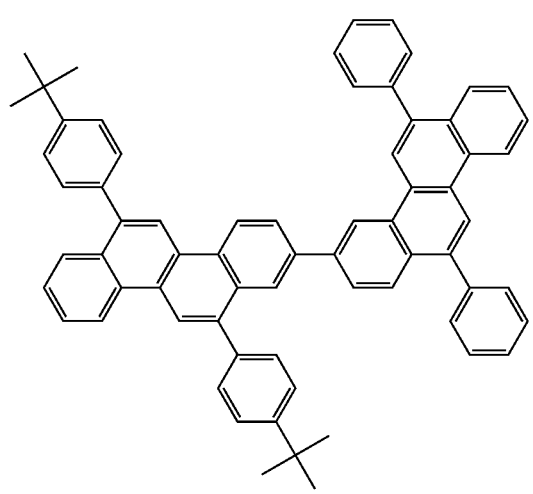
C308
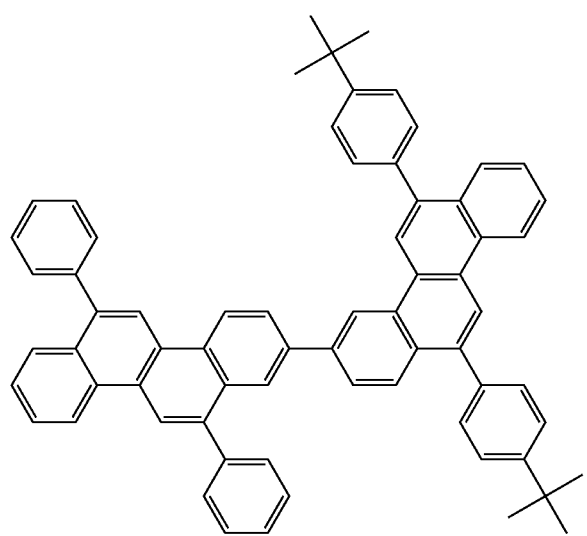
C309
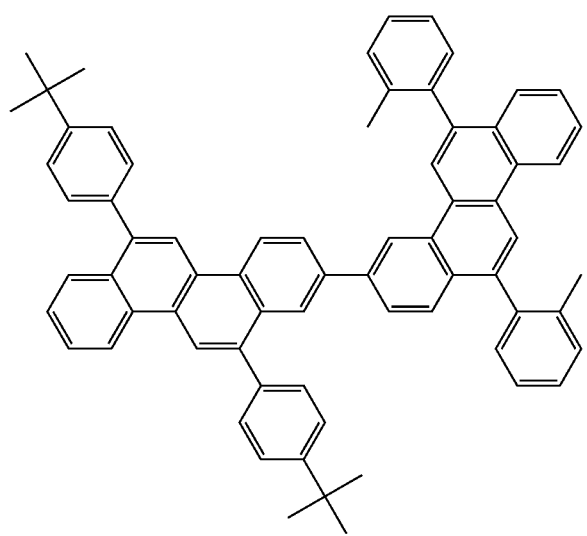

-continued
C310
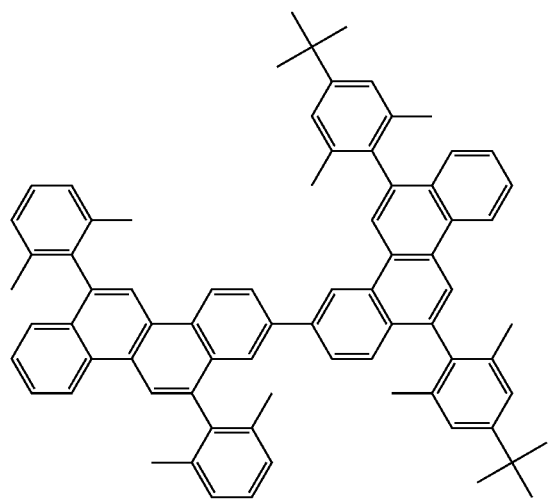
C311
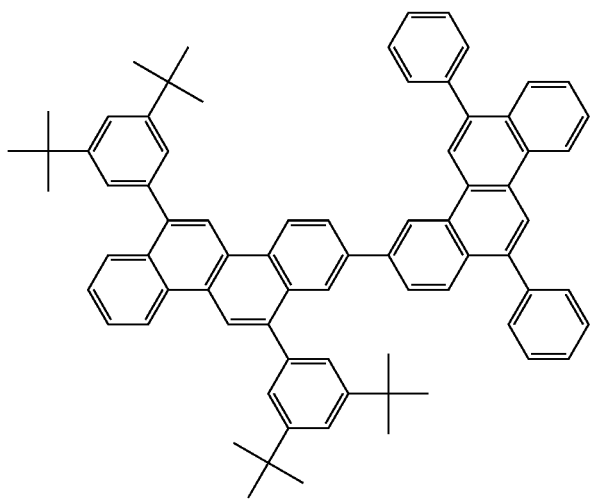
C312
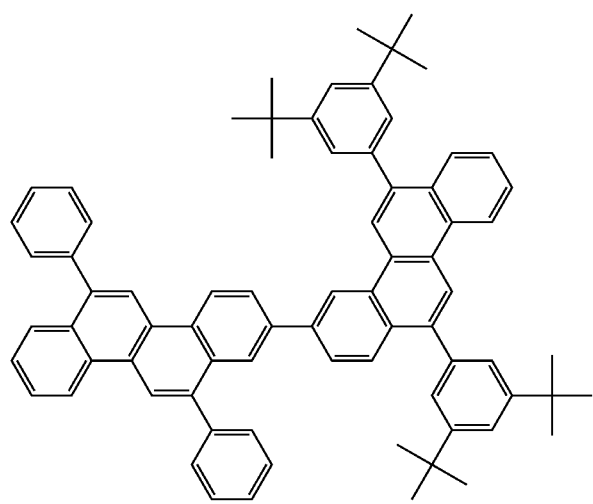
C313
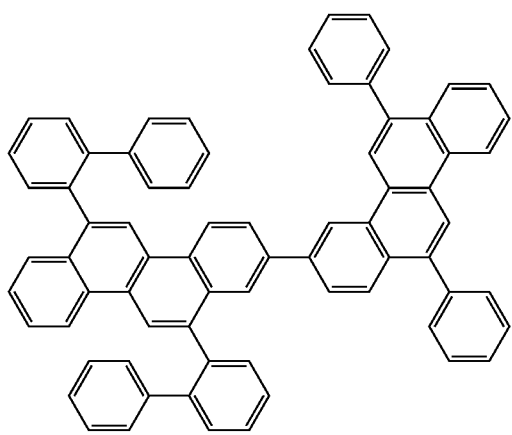
C314
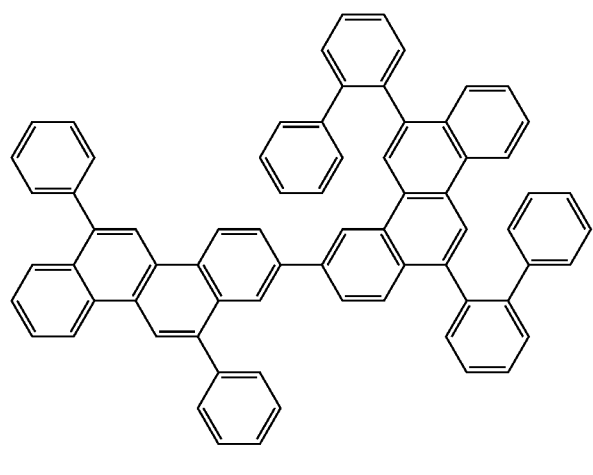
C315
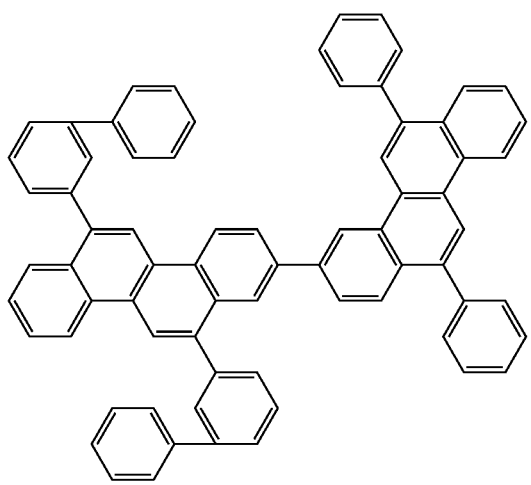

C316
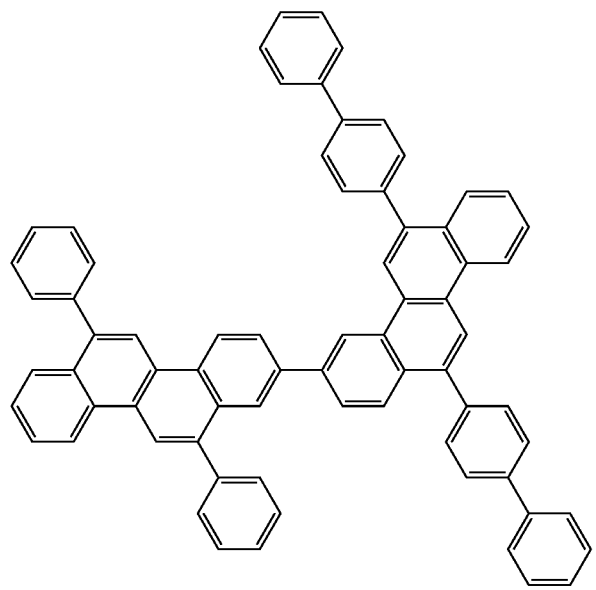
C317
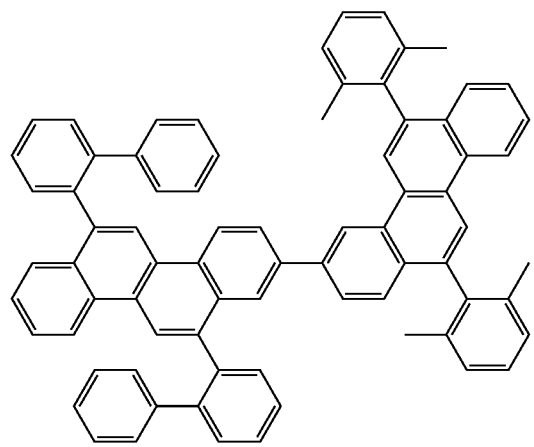
C318
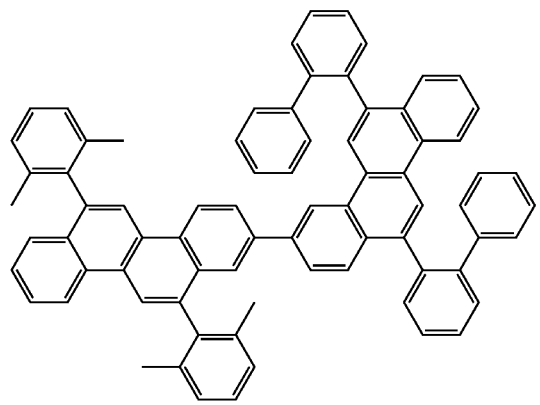
C401
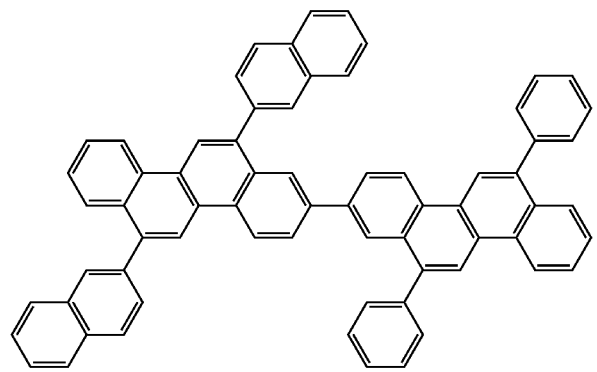
C402
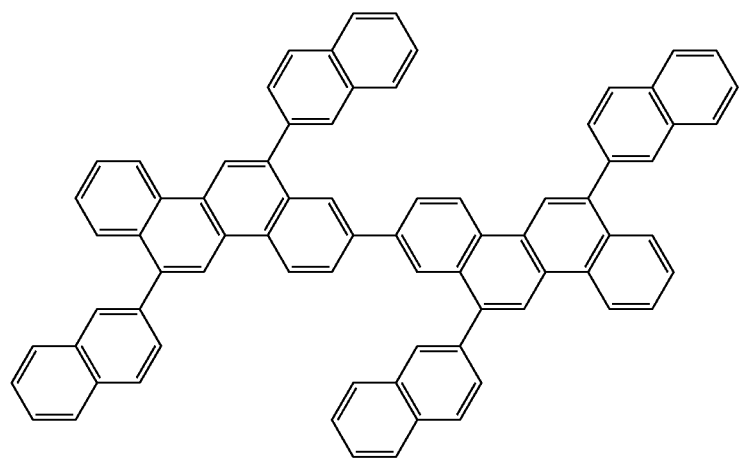

-continued
C403
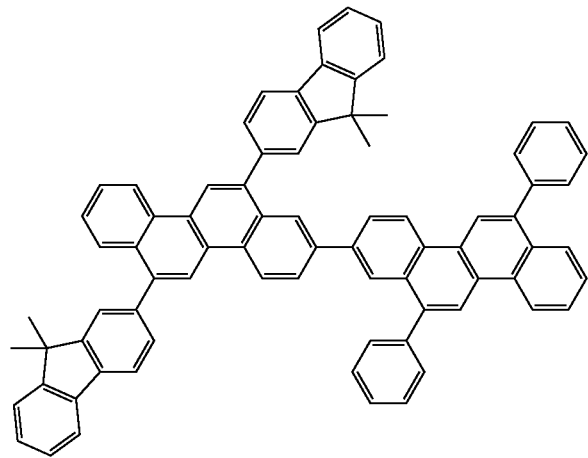
C404
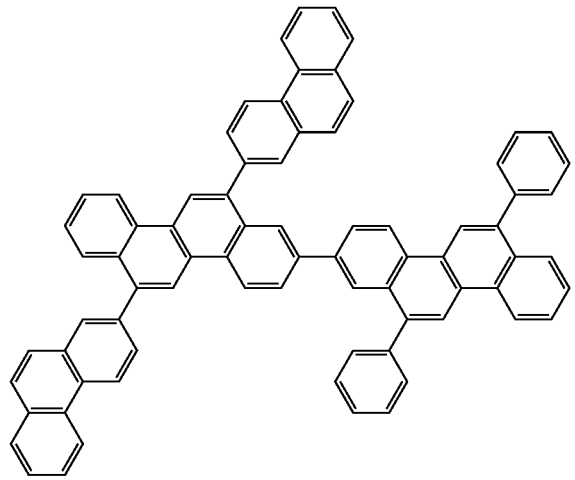
C405
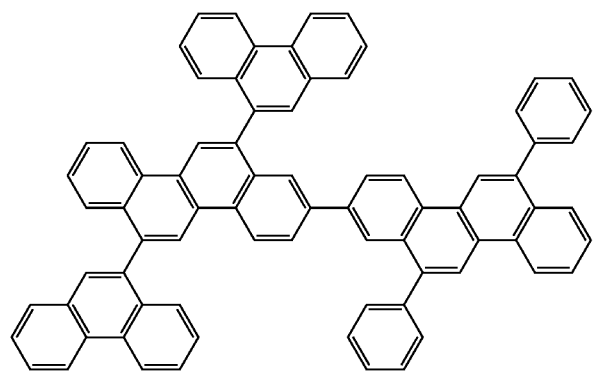
C406
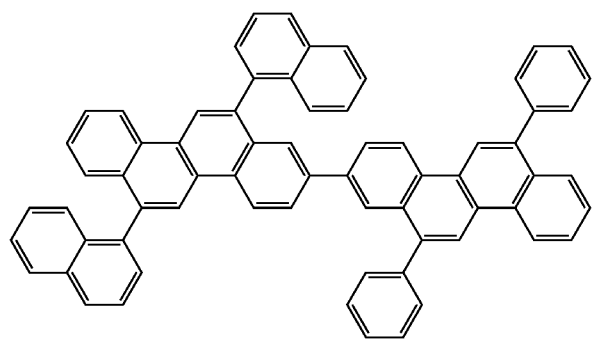
C407
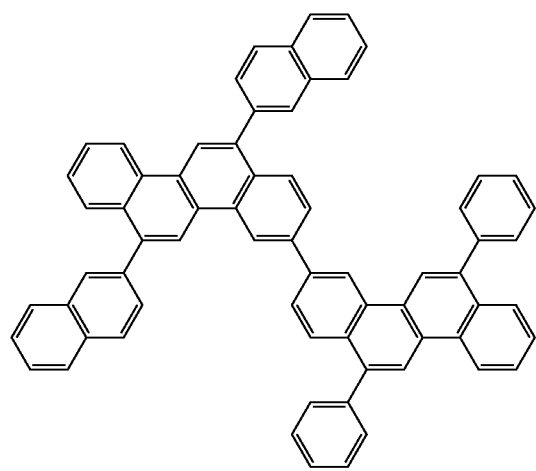
C408
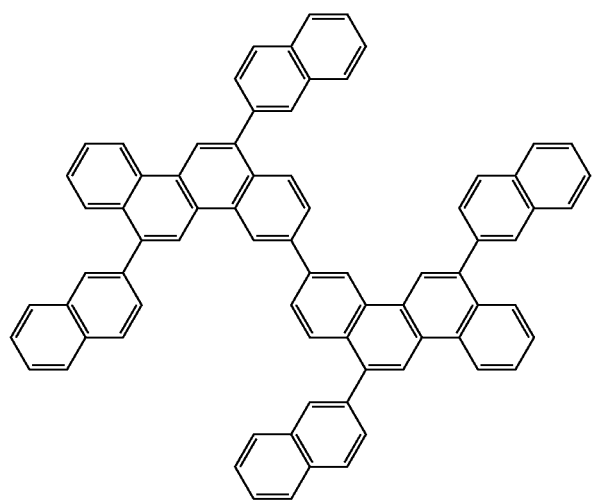

-continued
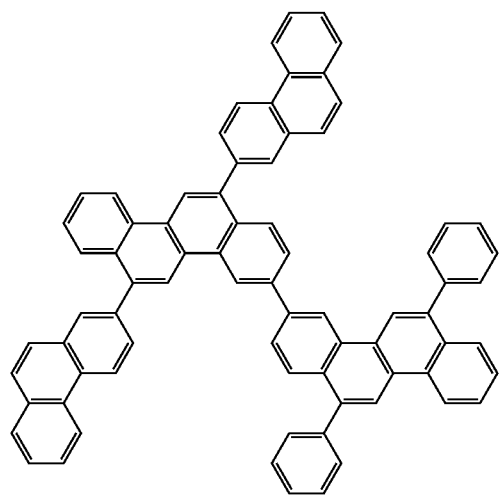

-continued
C415
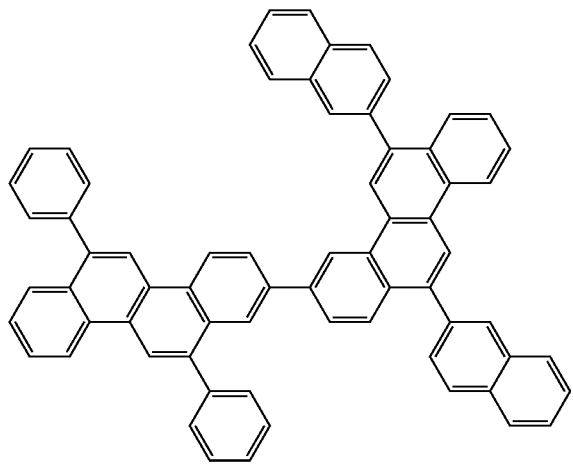
C416
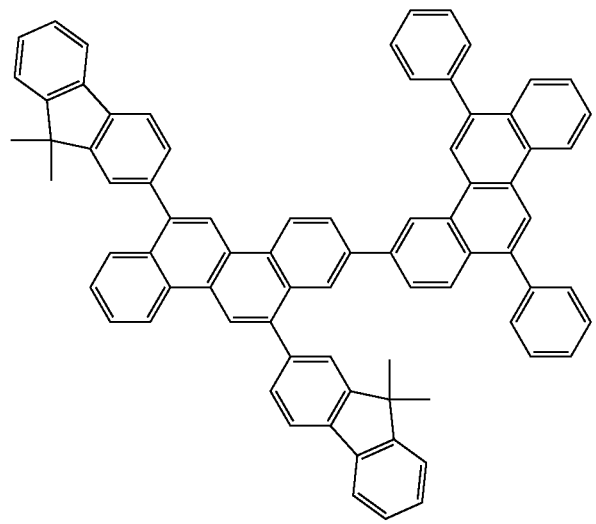
C417
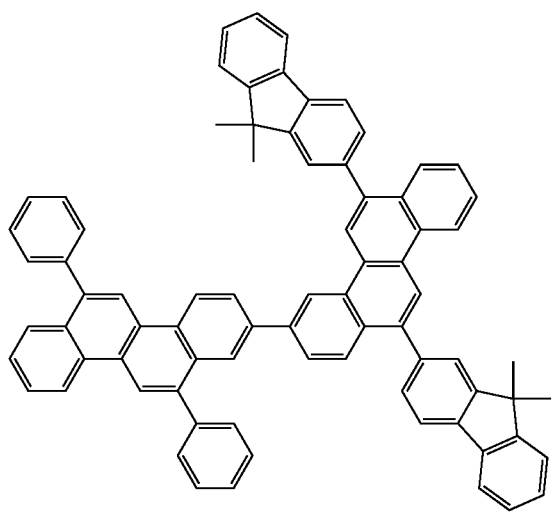
C418
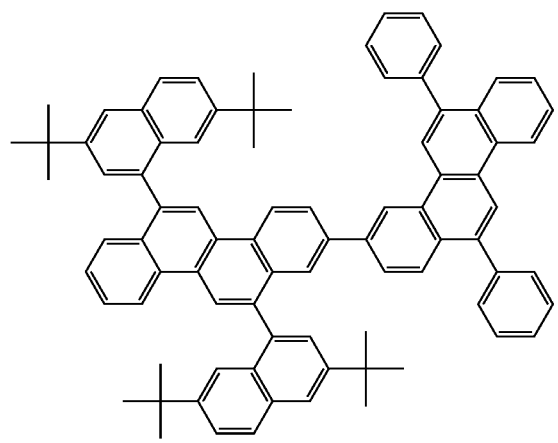
C501
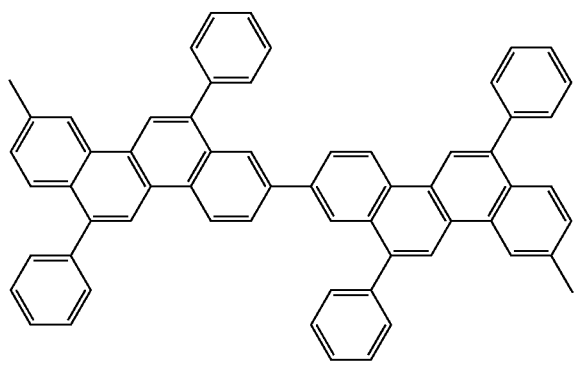

-continued
C502
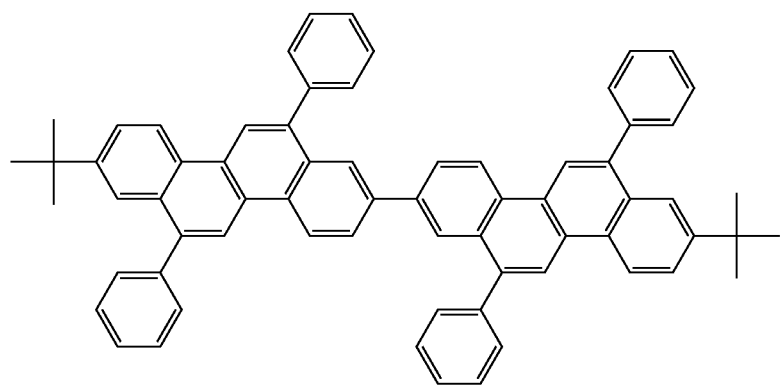
C503
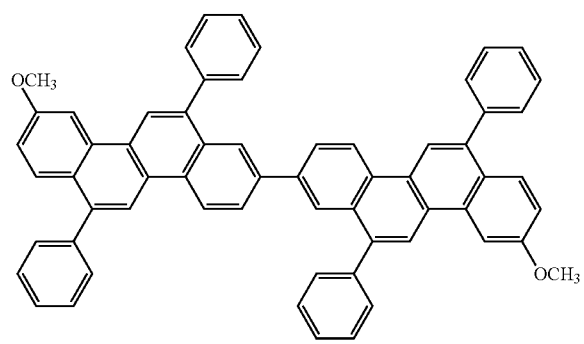
C504
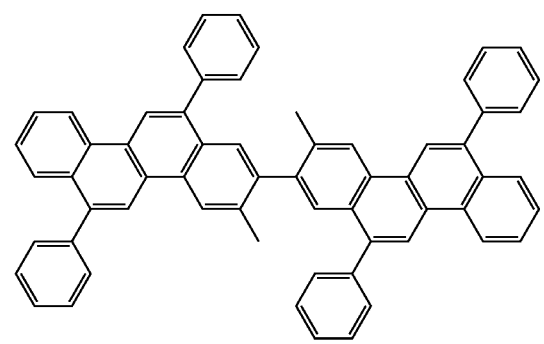
C505
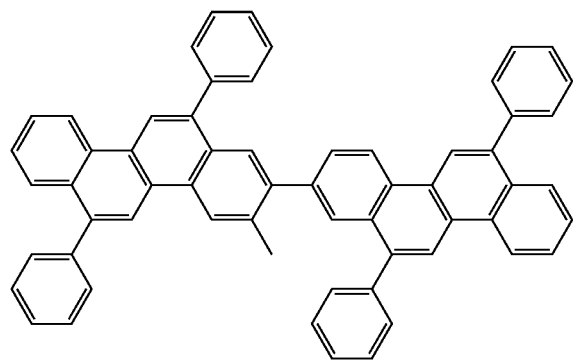
C506
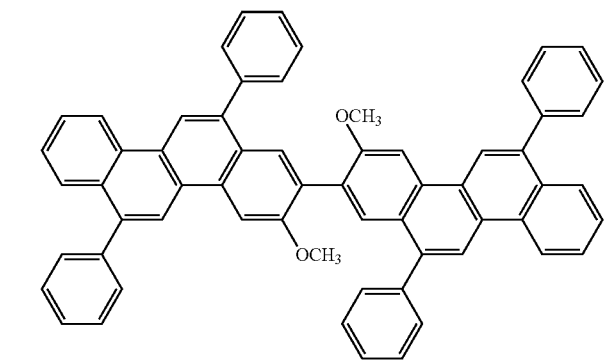
C507
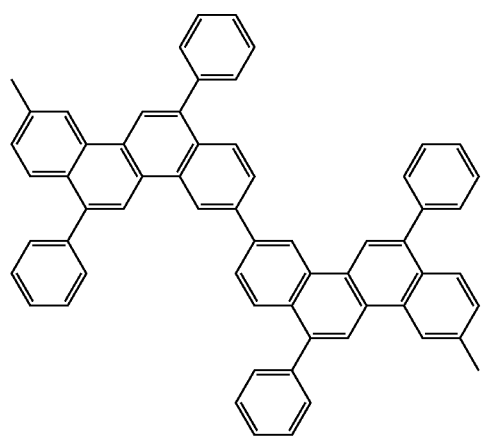
C508
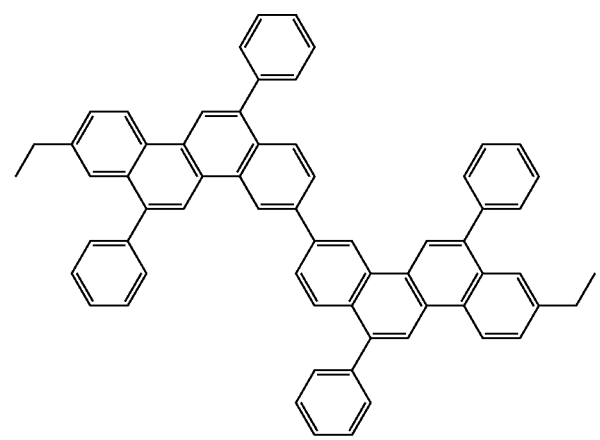

-continued
C509
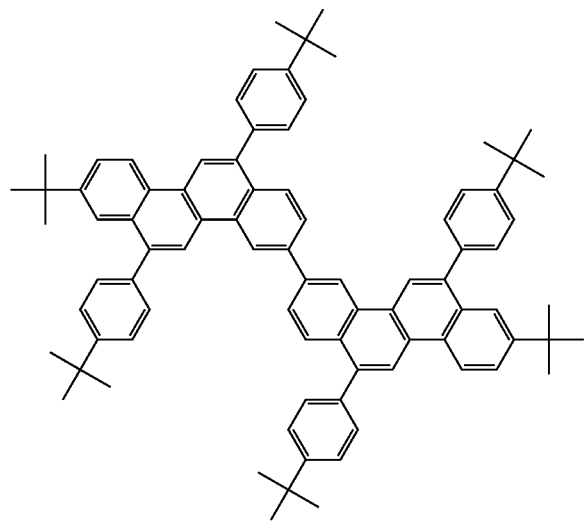
C510
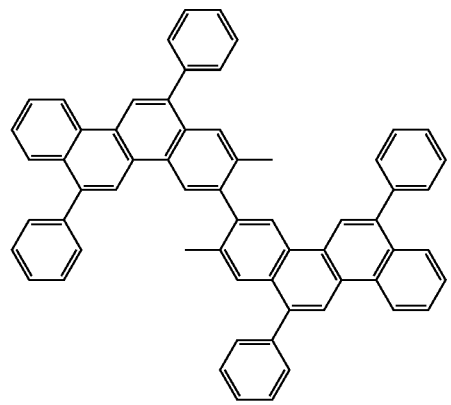
C511
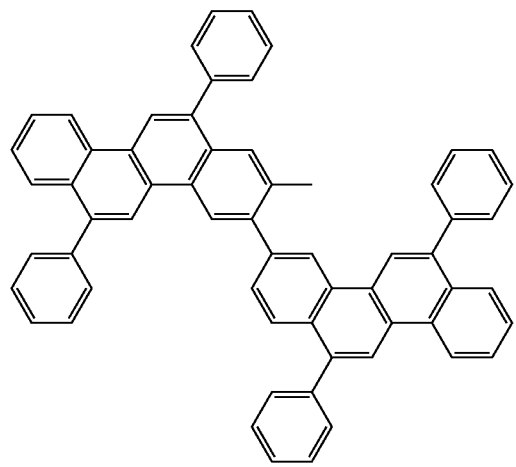
C512
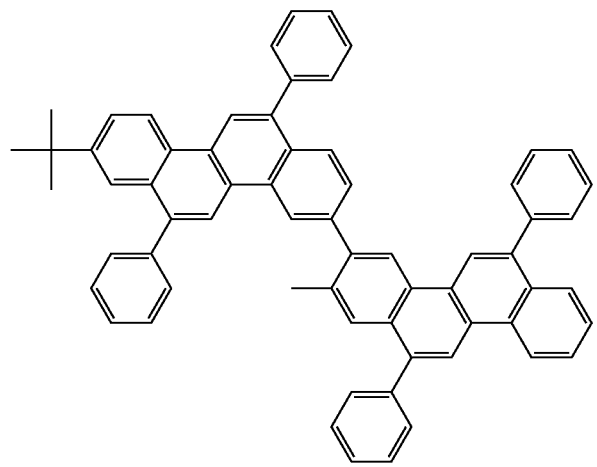
C513
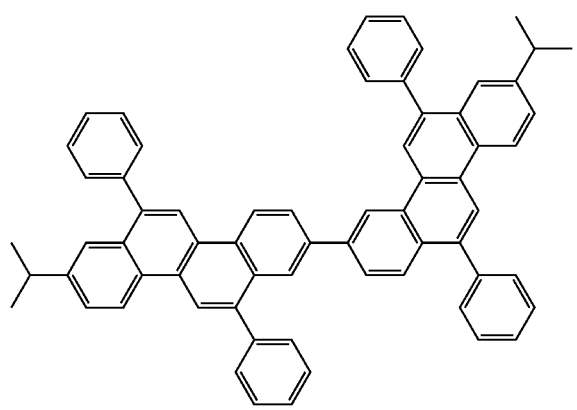
C514
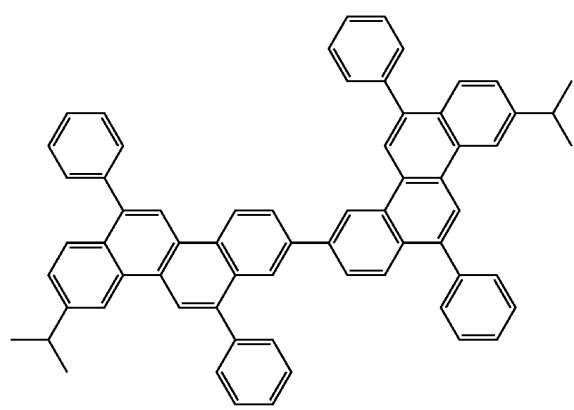

-continued
C515
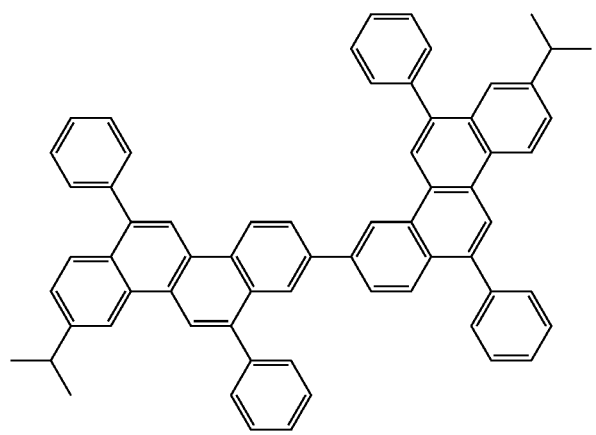
C516
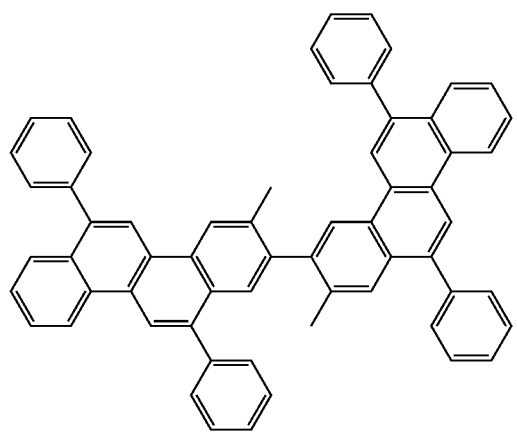
C517
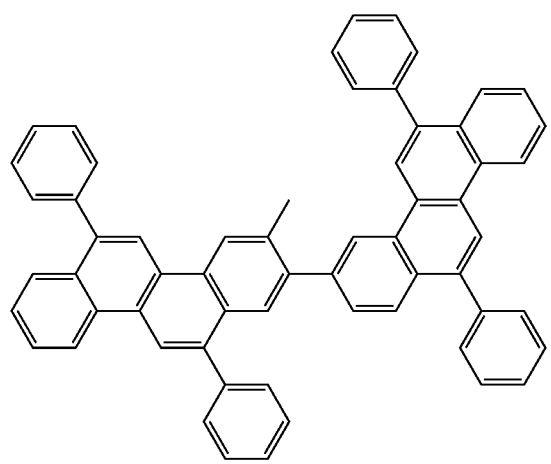
C518
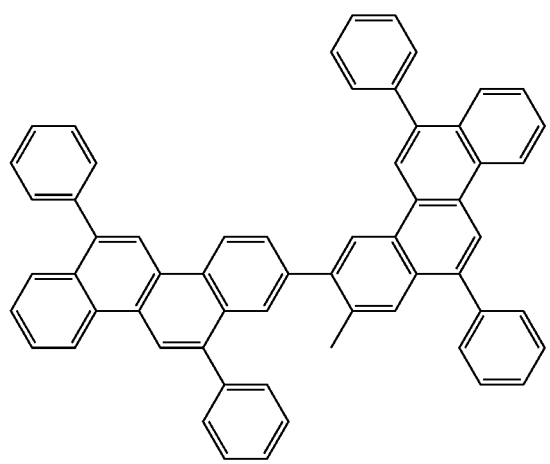
C519
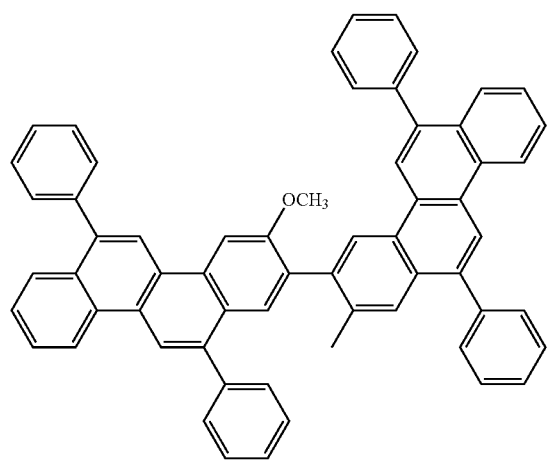
C520
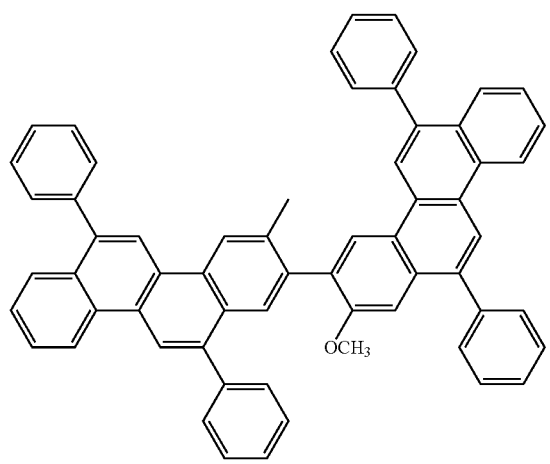

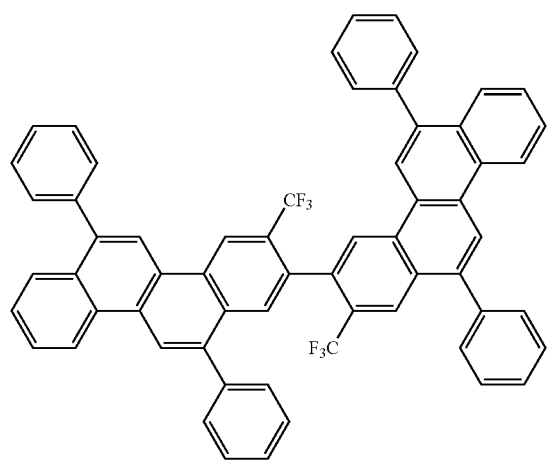

C521

The above-mentioned compounds C101 to C118 and C401 to C406 are specific examples of the general formula (2).

The above-mentioned compounds C201 to C215 and C407 to C412 are specific examples of the general formula (3).

The above-mentioned compounds C301 to C318 and C413 to C418 are specific examples of the general formula (4).

Next, the organic light emitting device according to the present invention is described in detail.

The organic light emitting device according to the present invention is an organic light emitting device including at least a pair of electrodes formed of an anode and a cathode, and a layer formed of an organic compound interposed between the pair of electrodes (organic compound layer), in which the organic compound layer contains an organic compound represented by any one of the general formulae (1) to (4).

The device may have a compound layer except the above-mentioned organic compound layer between the pair of electrodes. Alternatively, two or more compound layers including the organic compound layer may be provided between the pair of electrodes, and the device in such case is called a multilayer organic light emitting device.

Hereinafter, preferred examples of the multilayer organic light emitting device, i.e., first to fifth examples are described.

An organic light emitting device of such a constitution that the anode, an emission layer, and the cathode are sequentially provided on a substrate can be given as the first example of the multilayer organic light emitting device. The organic light emitting device used here is useful when a compound that itself has hole transport property, electron transport property, and emission property alone is used or when compounds having the respective properties are used as a mixture.

An organic light emitting device of such a constitution that the anode, a hole transport layer, an electron transport layer, and the cathode are sequentially provided on a substrate can be given as the second example of the multilayer organic light emitting device. This case is useful when a material having one or both of hole transport property and electron transport property is used as an emission substance in each layer in combination with a mere hole transport substance or electron transport substance having no emission property. In addition, in this case, the emission layer is formed of any one of the hole transport layer and the electron transport layer.

An organic light emitting device of such a constitution that the anode, the hole transport layer, the emission layer, the electron transport layer, and the cathode are sequentially provided on a substrate can be given as the third example of the multilayer organic light emitting device. The device constitution is such that a carrier transport function and an emission function are separated from each other. In addition, the constitution can be used in suitable combination with compounds having the respective properties, i.e., hole transport property, electron transport property, and emission property. In addition, the degree of freedom in material selection increases to an extreme extent, and various compounds having different emission wavelengths can be used. As a result, the diversification of emission hues can be achieved. Further, each carrier or exciton is effectively trapped in the central emission layer, and hence an improvement in light emitting efficiency can be achieved.

An organic light emitting device of such a constitution that the anode, a hole injection layer, the hole transport layer, the emission layer, the electron transport layer, and the cathode are sequentially provided on a substrate can be given as the fourth example of the multilayer organic light emitting device. The device constitution has an improving effect on adhesiveness between the anode and the hole transport layer or on hole injection property, and is effective in reducing the voltage at which the device is driven.

An organic light emitting device of such a constitution that the anode, the hole transport layer, the emission layer, a hole blocking layer or exciton blocking layer, the electron transport layer, and the cathode are sequentially provided on a substrate can be given as the fifth example of the multilayer organic light emitting device. The constitution is such that a layer for blocking the escape of a hole or exciton toward the cathode (the hole blocking layer or exciton blocking layer) is inserted between the emission layer and the electron transport layer. The use of a compound having an extremely high ionization potential in the hole blocking layer or exciton blocking layer is effective in improving the light emitting efficiency.

However, the first to fifth examples of the multilayer organic light emitting device have only a basic device constitution, and the constitution of the organic light emitting device using the bichrysene compound according to the present invention is not limited thereto. There can be given various layer constitutions, for example, a constitution in which an insulating layer is provided at an interface of an electrode and an organic layer, an adhesive layer or an interference layer is provided, an electron transport layer or a hole transport layer is formed of two layers having different ionization potentials, or an emission layer has a laminated structure formed of two layers or more.

The bichrysene compound represented by any one of the general formulae (1) to (4) used in the organic light emitting device according to the present invention can be used in any one of the first to fifth examples.

In the organic light emitting device according to the present invention, at least one kind of bichrysene compound represented by any one of the general formulae (1) to (4) of the present invention is incorporated into the layer containing the organic compound. In this case, one kind of bichrysene compound of the present invention may be incorporated into one layer, or two or more kinds of the compounds may be incorporated in combination.

In the organic light emitting device according to the present invention, the bichrysene compound of the present invention is particularly preferably used as a host material for the emission layer.

Alternatively, the bichrysene compound according to the present invention may be used as a guest material for the emission layer.

Further, the bichrysene compound according to the present invention may be used in any one of the respective layers except the emission layer, i.e., the hole injection layer, the hole transport layer, the hole blocking layer, the exciton blocking layer, the electron transport layer, and an electron injection layer.

Next, the organic light emitting device according to the present invention is described.

The organic light emitting device according to the present invention has at least an anode and a cathode serving as a pair of electrodes, and organic compound layers placed between the electrodes. The organic compound layers each have the bichrysene compound represented by any one of the above-mentioned general formulae (1) to (4). The organic light emitting device is such a device that a light emitting material as the organic compound placed between the pair of electrodes emits light.

When one of the organic compound layers is an emission layer, the emission layer may be formed only of the bichrysene compound according to the present invention, or may partly have the bichrysene compound according to the present invention. When the emission layer may partly have the bichrysene compound according to the present invention, the bichrysene compound according to the present invention may be the main component of the emission layer, or may be a sub-component of the layer.

The term "main component" as used herein refers to a compound present in a large amount in terms of, for example, weight or number of moles out of all compounds of which the emission layer is formed, and the term "sub-component" as used herein refers to a compound present in a small amount in terms of any such parameter. A material as the main component can be called a host material as well. Materials as sub-components can be called a guest (dopant) material, a light emitting assist material, and a charge injection material. Here, the guest material is a compound which plays a role of main emission inside the emission layer. On the other hand, the host material is a compound which is present as a matrix in the periphery of the guest material inside the emission layer, and mainly plays roles of transporting carriers and donating excitation energy to the guest material.

Here, the concentration of the guest material with respect to the host material is 0.01 wt % to 50 wt % and preferably 0.1 wt % to 20 wt % based on the total amount of the constituent materials of the emission layer. More preferably, in order to prevent concentration quenching, the concentration of the guest material is desirably 10 wt % or less. Further, the guest material may be uniformly included throughout the layer formed of the host material, may be included in the layer with a concentration gradient existing, or may be partially included in a certain area to form an area formed of the host material layer where no guest material is included.

When the emission layer of the organic light emitting device is formed of a carrier transporting host and guest, the main process for emission includes the following several steps where energy transfer or emission in each step occurs in competition with various deactivation steps.
(1) Transport of electron and hole in an emission layer
(2) Production of exciton of a host material
(3) Transmittance of excitation energy between host material molecules
(4) Transfer of excitation energy from a host material to a guest material
(5) Emission of a guest material (relaxation of excitation energy)

It is needless to say that the emission quantum efficiency of a light emitting center material itself must be increased in order to increase the light emitting efficiency of the organic light emitting device. On the other hand, it is also important to increase the efficiency of excitation energy transfer between a host and another host or between a host and a guest.

Known as the mechanism for the excitation energy transfer between the host and the guest is each of Förster mechanism based on a dipole-dipole interaction and Dexter mechanism based on an electron exchange interaction. In each of the mechanisms, it is important that the excitation energy of the host material be larger than that of the guest material, i.e., the energy gap of the host material be larger than that of the guest material in order that the excitation energy may transfer. The term "energy gap" as used herein refers to a difference between the HOMO level and Lowest Unoccupied Molecular Orbital (LUMO) level of a compound.

Although it is important that the energy gap of the host material be large, when the energy gap is excessively large, the transfer of the excitation energy to the guest material occurs, but there is a high possibility that the injection of a carrier from the hole transport layer or electron transport layer adjacent to the emission layer into the emission layer is inhibited. That is, with regard to the injection of a hole, a hole injection barrier that arises owing to a difference between the HOMO level of the hole transport layer and the HOMO level of the host for the emission layer enlarges, and hence the difficulty with which the hole is injected is raised. Similarly, with regard to the injection of an electron, an electron injection barrier that arises owing to a difference between the LUMO level of the electron transport layer and the LUMO level of the host for the emission layer enlarges, and hence the difficulty with which the electron is injected is raised. Therefore, the injection of both the carriers requires an additionally high bias voltage, which leads to an increase in voltage at which the organic light emitting device is driven. Further, a balance between both the carriers in the emission layer is lost to a large extent, which leads to a reduction in light emitting efficiency of the device.

In view of the foregoing, when both a highly efficient transfer of the excitation energy between the host and the guest, and good carrier injection property are taken into consideration, a preferred range exists for the magnitude of the energy gap of the host material depending on the energy gap of the guest material, i.e., an emission color. In the case of, for example, a blue fluorescent light emitting device in which the guest material emits blue light and which has a maximum emission wavelength of 430 nm to 470 nm, the energy gap of the host material is preferably about 3.0 eV, or specifically 3.0±0.2 eV, or more preferably from 3.0 eV to 3.1 eV.

Therefore, the bichrysene compound according to the present invention can be preferably used as a host material for a blue emission layer because the compound satisfies an energy gap within any such numerical range.

An anthracene compound using an anthracene ring as its core has been generally known as a host material for the emission layer of a blue fluorescent light emitting device. The energy gap of the anthracene compound is relatively small, and is 3.0 eV or less in many cases because the energy gap of the anthracene ring itself is small as compared to that of any other hydrocarbon aromatic ring having carbon atoms comparable in number to those of the anthracene ring. When such anthracene compound is used as a host for the emission layer of the blue fluorescent light emitting device, or in particular, a blue light emitting device using a blue light emitting guest having a high blue color purity, the efficiency with which excitation energy transfers between the host and the guest reduces, and hence the light emitting efficiency of the device reduces. The foregoing suggests that such anthracene compound has too small an energy gap to serve as a host for a blue emission layer.

Meanwhile, chrysene can be given as an example of the hydrocarbon aromatic ring having carbon atoms comparable in number to those of anthracene. The inventors of the present invention have noticed that the energy gap of a chrysene ring itself is larger than that of the anthracene ring, and the chrysene ring has a wide n-conjugated surface as in the case of the anthracene ring. Therefore, the energy gap of a chrysene compound using the chrysene ring as its core is larger than that of the anthracene compound. Accordingly, even when the compound is used as a host for the emission layer of a blue light emitting device, a highly efficient transfer of excitation energy between the host and a guest can be expected. In addition, good carrier conductivity can also be expected because the compound has a wide n-conjugated surface.

A bichrysene compound in which two chrysene rings are linked to each other is an example of the chrysene compound. Twenty-one kinds of isomers are available depending on a difference in linking positions. The material physical properties of those isomers such as an energy gap vary largely depending on the linking positions. In addition, the driving characteristic of the organic light emitting device also varies largely depending on which one of the isomers is used as a host material for its emission layer.

Any such variation originates from a large difference between the isomers in magnitude of steric repulsion between the two chrysene rings in a bichrysene compound, i.e., dihedral angle between the two chrysene rings. In actuality, when the structure of each bichrysene compound is optimized by molecular orbital calculation (B3LYP/6-31G*), the dihedral angle between the chrysene rings is as shown in Table 1 below. It should be noted that the numbers of the substitution positions of a chrysene ring are shown below.

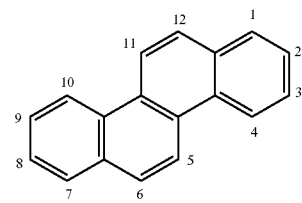

TABLE 1

| | Structural formula | Dihedral angle |
|---|---|---|
| 2,2'-bichrysene | | 35.4° |
| 3,3'-bichrysene | | 37.8° |
| 2,3'-bichrysene | | 35.6° |

TABLE 1-continued

| Structural formula | Dihedral angle |
|---|---|
| 6,6'-bichrysene 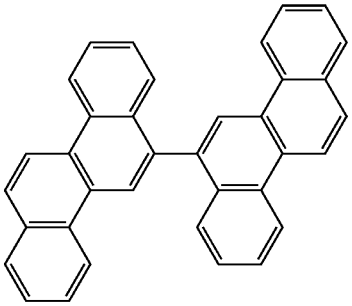 [SMILES: c1ccc2c(c1)ccc1c3ccccc3c(-c3cc4c5ccccc5ccc4c4ccccc34)cc21] | 72.3° |

In 6,6'-bichrysene, a peri-position hydrogen atom at the 7-position and a peri-position hydrogen atom at the 7'-position undergo large steric repulsion, and hence the dihedral angle between the chrysene rings is so large that the rings are substantially perpendicular to each other.

On the other hand, none of 2,2'-bichrysene, 3,3'-bichrysene, and 2,3'-bichrysene has such steric repulsion between peri-position hydrogens as described above, and hence the dihedral angle between the chrysene rings of each of the compounds is small. The difference in dihedral angle largely affects the magnitude of the energy gap of a bichrysene compound. To be specific, as the dihedral angle increases, a twist between the chrysene rings becomes large. As a result, π conjugation is cut and the energy gap increases.

In actuality, in the 6,6'-bichrysene compound, the two chrysene rings are substantially perpendicular to each other and a π-conjugation length is short. Accordingly, the energy gap of the compound is so large that the use of the compound as a host for a blue emission layer increases the voltage at which a light emitting device is driven and reduces the light emitting efficiency of the device. The foregoing suggests that the 6,6'-bichrysene compound has too large an energy gap to serve as a host material for the blue emission layer.

On the other hand, in each of the 2,2'-bichrysene compound, 3,3'-bichrysene compound, and 2,3'-bichrysene compound of the present invention, the dihedral angle between the two chrysene rings is small, and hence a twist between the chrysene rings is small and a π-conjugation length is linearly long. As a result, the energy gap of each of the compounds is smaller than that of the 6,6'-bichrysene compound. In particular, when the two chrysene rings are bonded to each other at the 3-positions of the chrysenes, the π-conjugation length elongates to a large extent, and the energy gap becomes additionally small so as to be about 3.0 eV. The use of such bichrysene compound of the present invention as a host material for a blue emission layer can provide a blue light emitting device which brings together a highly efficient transfer of excitation energy between the host and a guest, and good carrier injection property, and has high light emitting efficiency.

A small dihedral angle and a small twist between the chrysene rings improve the planarity of an entire molecule of a bichrysene compound. Accordingly, a stack due to an intermolecular interaction may be remarkable. The case where a stack between molecules, in particular, between host molecules occurs in an organic light emitting device is not preferred because an efficient transfer of excitation energy from a host to a guest is no longer performed owing to, for example, the formation of an excimer between the host molecules, and a reduction in light emitting efficiency of the light emitting device may occur.

However, in the bichrysene compound of the present invention, a substituted or unsubstituted hydrocarbon aromatic ring group is introduced into each of the 6- and 12-positions of the chrysene rings, i.e., $Ar_1$ to $Ar_4$ in the general formula (1). As a result, such intermolecular stack can be avoided because of the following reason. That is, as described above, an aromatic ring group substituting for the 6-position of a chrysene ring has a large dihedral angle relative to the chrysene ring by virtue of steric repulsion from a peri-position atom at the 7-position of the chrysene ring, and hence the aromatic ring group serves as a hindrance group for an interaction between the chrysene rings of molecules.

Such hindrance group for avoiding the stack is preferably a hydrocarbon aromatic ring group like the present invention rather than a bulky alkyl group. The reason for the foregoing is as described below. A large quantity of charge of an HOMO and an LUMO directly involved in an emission process is distributed on a chrysene ring, and hence a compound in which sp2 carbons are directly bonded to each other like an aromatic ring substituent is advantageous in terms of energy.

In addition, a cause for the deterioration of the emission of an organic light emitting device due to electrification has not been explicated yet. However, it is assumed that the deterioration is related to at least a light emitting center material itself or a change in environment surrounding the light emitting material due to a molecule around the material. In addition, the deterioration of the quality of an amorphous film due to, for example, crystallization, the deterioration of an organic layer over time due to electrification, or the like is also considered to be a cause for the deterioration of the emission of the organic light emitting device.

The deterioration of the light emitting material due to oxidation is one kind of the deterioration of the material, and the presence of an oxide in the organic light emitting device is known to impair the durable lifetime of the device remarkably. The impairment is remarkable particularly in the case of an anthracene compound because the carbon atoms at the 9- and 10-positions of the anthracene ring are oxidized with extreme ease. On the other hand, the oxidation resistance of a chrysene ring is strong, and hence the chemical stability of a chrysene compound is extremely high. Accordingly, it can be said that the use of the chrysene compound in the organic light emitting device is advantageous for lengthening the lifetime of the device.

In addition, in general, the final purification of an organic compound used in an organic light emitting device is preferably performed by sublimation purification. This is because the sublimation purification exerts a large purifying effect in an increase in purity of the organic compound. Such sublimation purification generally requires a higher temperature as the molecular weight of the organic compound increases. In this case, thermal decomposition or the like is apt to occur owing to the high temperature. Therefore, the organic compound used in the organic light emitting device has a molecular weight of preferably 1200 or less, or more preferably 1000 or less so that the sublimation purification can be performed without any excessive heating.

Accordingly, in the bichrysene compound of the present invention, a substituted or unsubstituted phenyl group preferably substitutes for each of the 6- and 12-positions of the chrysene rings, i.e., $Ar_1$ to $Ar_4$ in the general formula (1) so that the molecular weight of the entire compound may be small.

By the way, an entire molecule of the bichrysene compound of the present invention is elongated in the long axis direction of its chrysene rings and has high linearity. As a result, a π-conjugation length in the molecule is extended, and hence the compound has good lead wire-like electronic conductivity. Therefore, the bichrysene compound of the present invention is effective also when used in the electron transport layer. In particular, the bichrysene compound of the present invention has a relatively deep HOMO level (large ionization potential). Accordingly, when the compound is used in the electron transport layer, hole blocking property is exerted and a carrier can be trapped in the emission layer, and hence the light emitting efficiency of the device can be improved. Further, the bichrysene compound of the present invention has a relatively large energy gap. Accordingly, when the compound is used in the electron transport layer, exciton blocking property is also exerted and an exciton can be trapped in the emission layer, and hence the light emitting efficiency of the device can be improved.

When the bichrysene compound according to the present invention is used as a host material for the emission layer, the substituents $Ar_1$ to $Ar_4$ of the general formula (1) are each preferably a phenyl group out of the above-mentioned substituents. This is because, as described above, when the molecular weight of the bichrysene compound is smaller, the sublimation purification and vapor deposition under heat at the time of the production of the device can be performed easily without any thermal decomposition due to excessive heating.

When the bichrysene compound according to the present invention is used as a host material for the emission layer, the substituents $R_1$ to $R_{18}$ of the general formula (1) are each preferably a hydrogen atom out of the above-mentioned substituents. This is because the compound has high chemical stability when the compound is unsubstituted. In other words, a large quantity of charge of an HOMO and an LUMO directly involved in the emission process is distributed on the two chrysene rings of the bichrysene compound, and hence a state where a substituent except an aromatic ring directly substitutes for each of the rings is disadvantageous in terms of energy.

When the bichrysene compound according to the present invention is used as a host material for the emission layer, the substituents $X_1$ to $X_{20}$ of the general formula (2) are each preferably a hydrogen atom out of the above-mentioned substituents. The reasons for the foregoing are as described below. As described above, the molecular weight of the compound is small, and hence the compound is stable in a process involving heating. In addition, only sp2 carbons are present in each molecule of the compound, and hence the chemical stability of the compound is high.

Similarly, when the bichrysene compound according to the present invention is used as a host material for the emission layer, the substituents $X_{21}$ to $X_{40}$ of the general formula (3) and the substituents $X_{41}$ to $X_{60}$ of the general formula (4) are each preferably a hydrogen atom out of the above-mentioned substituents.

Therefore, when the bichrysene compound according to the present invention is used as a host material for the emission layer, out of, for example, Compounds C101 to C521 shown above, Compounds C101, C201, and C301 are preferred.

When the bichrysene compound according to the present invention is used as a material of which the electron transport layer is formed, the substituents $Ar_1$ to $Ar_4$ of the general formula (1) are each preferably a phenyl group out of the above-mentioned substituents as in the case where the compound is used as a host material for the emission layer.

When the bichrysene compound according to the present invention is used as a material of which the electron transport layer is formed, the substituents $R_1$ to $R_{18}$ of the general formula (1) are each preferably a hydrogen atom out of the above-mentioned substituents as in the case where the compound is used as a host material for the emission layer.

In addition, when the bichrysene compound according to the present invention is used as a material of which the electron transport layer is formed, the substituents $X_1$ to $X_{20}$ of the general formula (2) are each preferably a hydrogen atom out of the above-mentioned substituents. This is because, as in the case where the compound is used as a host material for the emission layer, the compound has high chemical stability in a heating process or the like, and the compound may show high electron transport property when the compound is unsubstituted.

Similarly, when the bichrysene compound according to the present invention is used as a material of which the electron transport layer is formed, the substituents $X_{21}$ to $X_{40}$ of the general formula (3) and the substituents $X_{41}$ to $X_{60}$ of the general formula (4) are each preferably a hydrogen atom out of the above-mentioned substituents.

Therefore, when the bichrysene compound according to the present invention is used as a material of which the electron transport layer is formed, out of, for example, Compounds C101 to C521 shown above, Compounds C101, C201, and C301 are preferred.

As described above, the organic light emitting device of the present invention is such that at least one kind of bichrysene compound of the present invention is incorporated into the layer formed of an organic compound. In addition, the bichrysene compound of the present invention is preferably used as a host material for the emission layer of a blue light emitting device or a material for the electron transport layer of the device, but its applications are not limited to the foregoing. To be specific, the compound may be used as, for example, a host material in the emission layer of a green light emitting device.

In the organic light emitting device according to the present invention, the bichrysene compound of the present invention is preferably used as a host material for the emission layer. The compound is particularly preferably used as a host material for the emission layer of a blue light emitting device. Specific compounds each of which is used as a guest material for the blue light emitting device in this case are shown below. However, the present invention is of course not limited to the compounds.

(Blue light emitting guest materials)
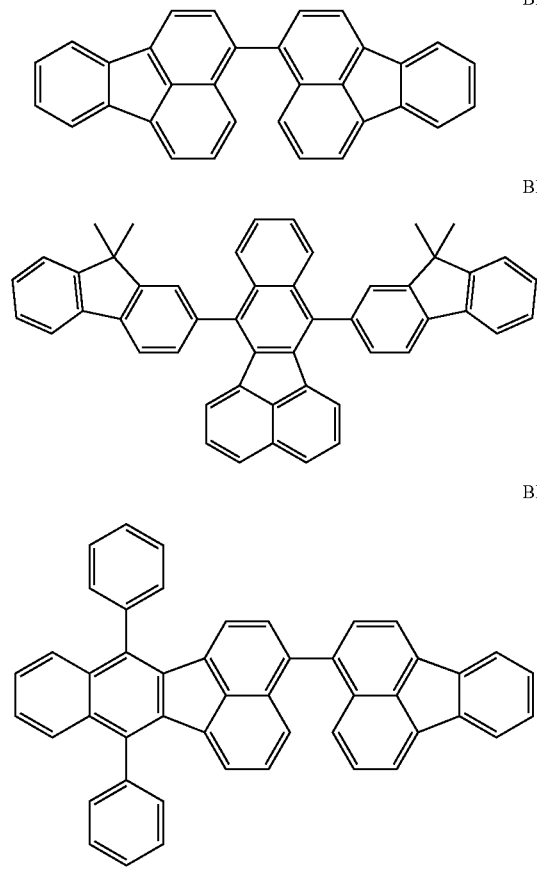
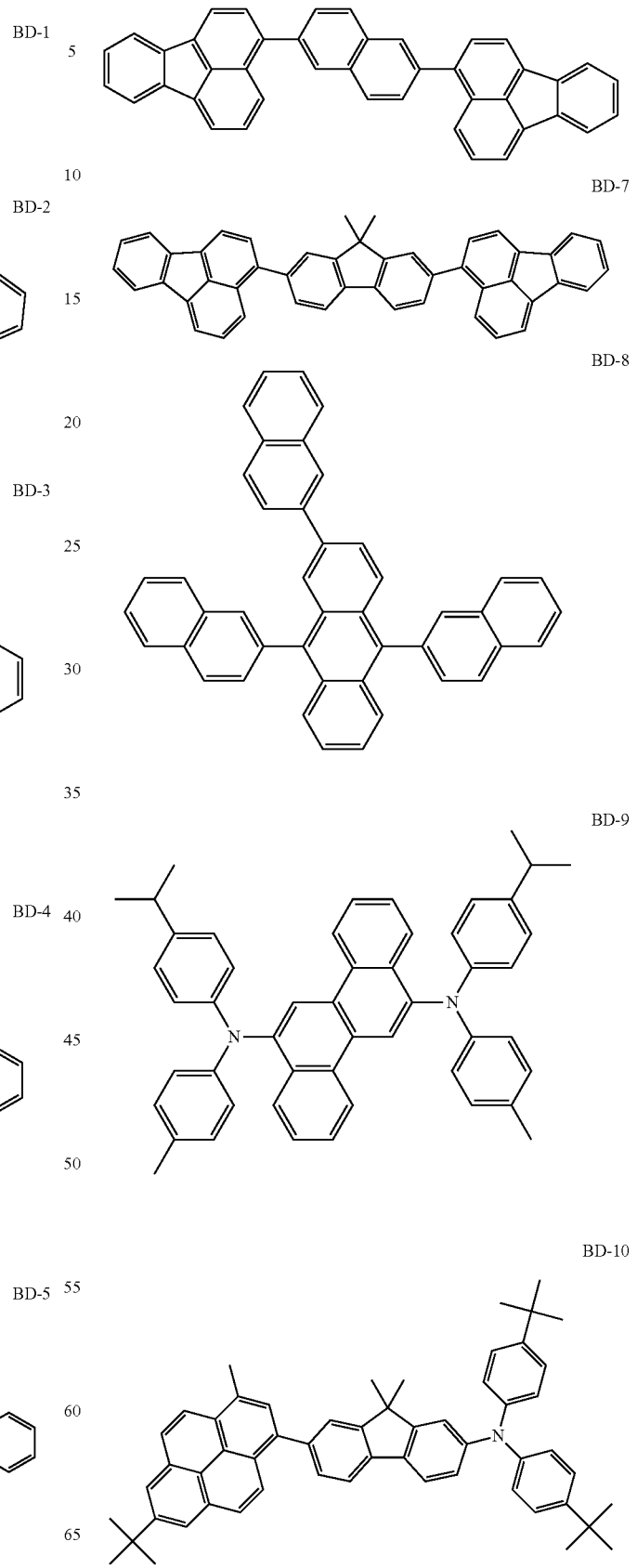

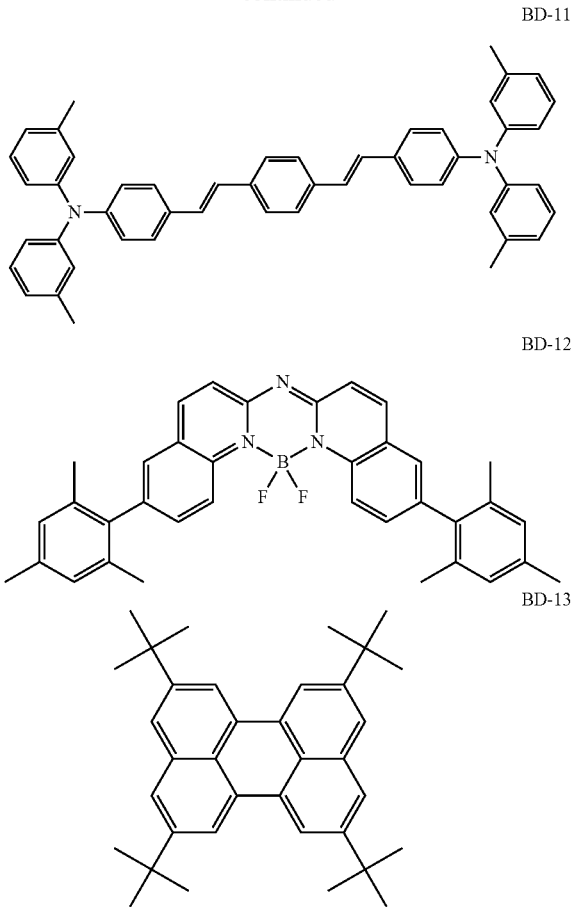

Alternatively, the bichrysene compound according to the present invention may be used as a guest material for the emission layer.

Further, the bichrysene compound according to the present invention may be used in any one of the respective layers except the emission layer, i.e., the hole injection layer, the hole transport layer, the hole blocking layer, the exciton blocking layer, the electron transport layer, and the electron injection layer.

Here, in the organic light emitting device of the present invention, there can be used together the following conventionally known compound as required, in addition to the bichrysene compound of the present invention: a low-molecular or high-molecular hole transport compound, a light emitting compound, an electron transport compound, or the like.

Those compounds are exemplified below.

A hole injection/transport material is preferably a material having a high hole mobility to facilitate the injection of a hole from an anode and to transport the injected hole to an emission layer. As low-molecular and high-molecular materials having hole injection/transport properties, there are exemplified a triarylamine derivative, a phenylene diamine derivative, a stilbene derivative, a phthalocyanine derivative, a porphyrin derivative, poly(vinylcarbazole), poly(thiophene), and other conductive polymers, but the material is of course not limited thereto.

As a light emitting material mainly involved in the emission function, in addition to the above-mentioned blue light emitting guest material and derivatives thereof, there are exemplified: fused ring compounds (such as fluorene derivatives, naphthalene derivatives, pyrene derivatives, perylene derivatives, tetracene derivatives, anthracene derivatives, and rubrene); quinacridone derivatives; coumarin derivatives; stilbene derivatives; organic aluminum complexes such as tris(8-quinolinolato)aluminum; organic beryllium complexes; and polymer derivatives such as poly(phenylene vinylene) derivatives, poly(fluorene) derivatives, and poly(phenylene) derivatives, but the material is of course not limited thereto.

The electron injection/transport material may be arbitrarily selected from compounds each of which facilitates the injection of an electron from a cathode and is capable of transporting the injected electron to the emission layer. In addition, the material is selected in consideration of, for example, a balance with the hole mobility of the hole injection/transport material. As materials having electron injection/transport properties, there are exemplified an oxadiazole derivative, an oxazole derivative, a pyrazine derivative, a triazole derivative, a triazine derivative, a quinoline derivative, a quinoxaline derivative, a phenanthroline derivative, and organic aluminum complexes, but the material is of course not limited thereto.

As an anode material, a material having as large a work function as possible is preferred. Examples of the material which may be used include: metal elements such as gold, platinum, silver, copper, nickel, palladium, cobalt, selenium, vanadium, and tungsten, and alloys including a combination of those metal elements; and metal oxides such as tin oxide, zinc oxide, indium oxide, indium tin oxide (ITO), and indium zinc oxide. Further, conductive polymers such as polyaniline, polypyrrole, and polythiophene may also be used. Each of those electrode substances may be used alone, or two or more kinds thereof may be used in combination. Further, the anode may be formed of a single layer, or may be formed of multiple layers.

On the other hand, as a cathode material, a material having a small work function is preferred. Examples of the material include: alkali metals such as lithium; alkali earth metals such as calcium; and metal elements such as aluminum, titanium, manganese, silver, lead, and chromium. Alternatively, alloys including a combination of those metal elements may also be used. For example, magnesium-silver, aluminum-lithium, and aluminum-magnesium can be used. Metal oxides such as indium tin oxide (ITO) may also be used. One kind of those electrode substances may be used alone or two or more kinds thereof may be used in combination. Further, the cathode may be formed of a single layer, or may be formed of multiple layers.

At least one of the anode and the cathode is transparent or semi-transparent.

Examples of the substrate to be used in the organic light emitting device of the present invention include, but are not particularly limited to: opaque substrates such as metallic substrates and ceramic substrates; and transparent substrates such as glass, quartz, and plastic sheet substrates. In addition, a color filter film, a fluorescent color conversion filter film, a dielectric reflection film, or the like may be used in the substrate to control emission color.

It should be noted that a protective layer or a sealing layer may be formed on the prepared device to prevent the device from contacting oxygen, moisture, or the like. Examples of the protective layer include a diamond thin film, a film made of an inorganic material such as a metal oxide or a metal nitride, a polymer film made of a fluorine resin, polyethylene, a silicone resin, a polystyrene resin, or the like, and a photo-curing resin. Further, the device itself can be covered with glass, a gas-impermeable film, a metal, or the like and packaged with an appropriate sealing resin.

Moreover, with respect to a direction of extracting light from the device, both a bottom emission structure (structure in which light is extracted from the substrate side) and a top emission structure (structure in which light is extracted from a side opposite to the substrate) may be adopted.

In the organic light emitting device of the present invention, a layer containing the bichrysene compound of the present invention and a layer formed of another organic compound are formed by a method described below. In general, a thin film is formed by a vacuum deposition method, an ionization-assisted deposition method, a sputtering method, or a plasma method, or the thin film may be formed by dissolving the compound in a suitable solvent and subjecting the resultant to a known coating method (e.g., a spin coating method, a dipping method, a casting method, an LB method, or an ink jet method). Here, when the layer is formed by the vacuum deposition method, a solution coating method, the layer hardly undergoes crystallization, and is excellent in stability over time. In addition, in film formation by the coating method, the film may be formed by using a compound in combination with an appropriate binder resin.

Examples of the above-mentioned binder resin include, but are not limited to, a polyvinylcarbazole resin, a polycarbonate resin, a polyester resin, an ABS resin, an acrylic resin, a polyimide resin, a phenol resin, an epoxy resin, a silicone resin, and a urea resin. In addition, as a homopolymer or a copolymer, one kind of binder resin may be used alone or a mixture of two or more kinds may be used.

Further, a known additive such as a plasticizer, an antioxidant, or a UV absorber, as required, may be used in combination.

The organic light emitting device of the present invention can be applied to products which require energy saving and high luminance. Examples of the application include a display apparatus, a light source of a printer, a lighting system, and a backlight of a liquid crystal display apparatus.

As the display apparatus, there can be exemplified an energy-saving light-weight flat panel display having high visibility.

In addition, when the organic light emitting device of the present invention is used as a pixel in a display portion, an imaging system such as a digital camera having the display portion and an imaging portion for imaging can be preferably provided.

Further, as the light source of a printer, for example, a laser light source portion of a laser-beam printer, which is widely used at present, can be replaced with the organic light emitting device of the present invention. As a method of replacing the laser light source portion, there can be exemplified a method involving arranging organic light emitting devices in an array. In this case, each of the organic light emitting devices can be addressed independently. When the laser light source portion is replaced with the organic light emitting device of the present invention, no change is observed as compared with the conventional laser-beam printer in regard to forming an image by performing desired exposure on a photosensitive drum. Here, by using the organic light emitting device of the present invention, the volume of the system can be reduced to a large extent.

As for the lighting system and the backlight, an energy-saving effect can be expected by using the organic light emitting device of the present invention.

In addition, an emission color can be controlled by providing the substrate supporting the organic light emitting device according to the present invention with a color filter film, fluorescent color conversion filter film, dielectric reflection film, or the like. In addition, whether or not the organic light emitting device emits light can be controlled by providing the substrate with a thin-film transistor (TFT), and connecting the device to the TFT. In addition, multiple organic light emitting devices are arranged in a matrix fashion, i.e., in an in-plane direction, and the resultant can be used as a lighting system.

Next, a display apparatus using the organic light emitting device of the present invention is described. The display apparatus includes the organic light emitting device of the present invention and units for supplying electrical signals to the organic light emitting device according to the present invention. Hereinafter, the display apparatus of the present invention is described in detail with reference to the drawings by taking an active matrix type as an example.

First, the symbols in FIGS. 1 to 4 are outlined. A display apparatus is represented by 1, pixel circuits are represented by 2 and 15, a scanning signal driver is represented by 11, an information signal driver is represented by 12, a current supply source is represented by 13, a pixel is represented by 14, and a first thin-film transistor (TFT1) is represented by 21. In addition, a capacitor (Cadd) is represented by 22, a second thin-film transistor (TFT2) is represented by 23, a substrate is represented by 31, a moisture-proof film is represented by 32, and a gate electrode is represented by 33. In addition, a gate insulating film is represented by 34, a semiconductor film is represented by 35, a drain electrode is represented by 36, a source electrode is represented by 37, a TFT device is represented by 38, and an insulating film is represented by 39. In addition, a contact hole (through hole) is represented by 310, an anode is represented by 311, an organic layer is represented by 312, a cathode is represented by 313, a first protective layer is represented by 314, and a second protective layer is represented by 315.

FIG. 1 illustrates one form of the display apparatus. The figure schematically illustrates an example of the constitution of the display apparatus including the organic light emitting device of the present invention and the units for supplying electrical signals to the organic light emitting device according to the present invention.

Figure 2:
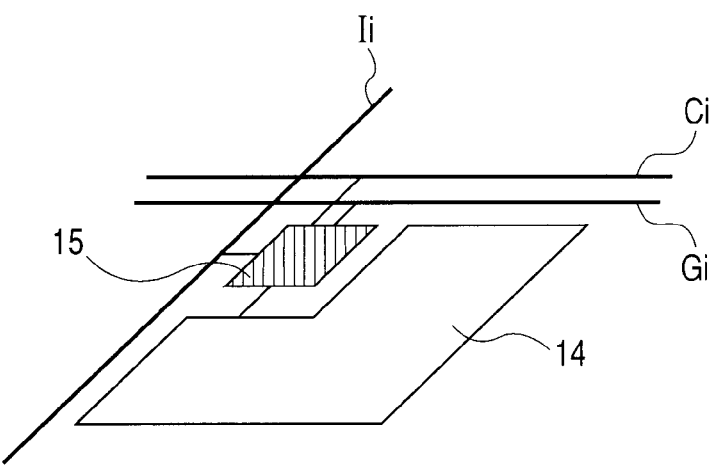
FIG. 2 is a view schematically illustrating a pixel circuit connected to a pixel, and a signal line and a current supply line connected to the pixel circuit.

FIG. 2 is a view schematically, illustrating a pixel circuit connected to a pixel, and a signal line and a current supply line connected to the pixel circuit.

The units for supplying electrical signals to the organic light emitting device according to the present invention refer to the scanning signal driver 11, the information signal driver 12, and the current supply source 13 in FIG. 1, and the pixel circuit 15 in FIG. 2.

In the display apparatus 1 of FIG. 1, the scanning signal driver 11, the information signal driver 12, and the current supply source 13 are placed, and are connected to gate selection lines G, information signal lines I, and current supply lines C, respectively. The pixel circuits 15 are placed at points of intersection of the gate selection lines G and the information signal lines I (FIG. 2). The pixels 14 each formed of the organic light emitting device according to the present invention are provided in correspondence with the pixel circuits 15. The pixels 14 are each an organic light emitting device. Therefore, each organic light emitting device is illustrated as an emission point in the figure. In the figure, the upper electrode of one organic light emitting device may be common to the upper electrode of another organic light emitting device. Of course, an upper electrode may be individually provided for each light emitting device.

The scanning signal driver 11 sequentially selects the gate selection lines G1, G2, G3, . . . , Gn, and in synchronization with the selection, an image signal is applied from the information signal driver 12 to each of the pixel circuits 15 through any one of the information signal lines I1, I2, I3, . . . , In.

Figure 3:
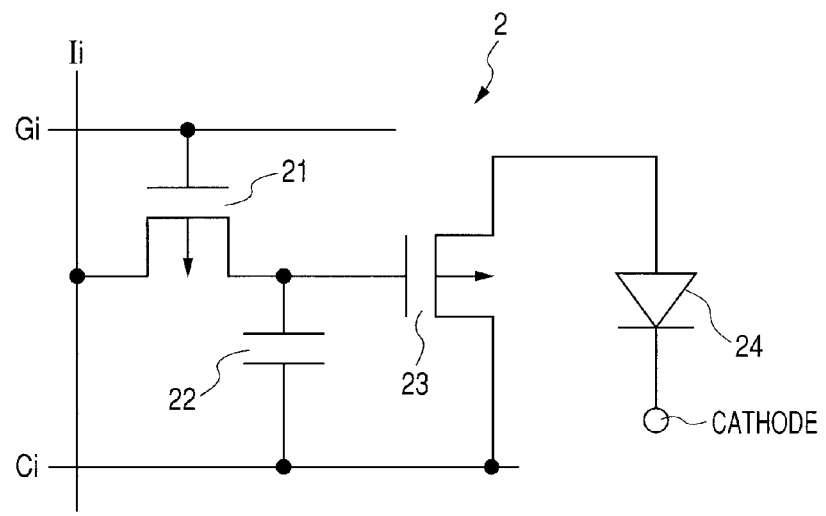
FIG. 3 is a view illustrating the pixel circuit.

Next, the operation of each pixel is described. FIG. 3 is a circuit diagram illustrating a circuit of which one pixel placed in the display apparatus of FIG. 1 is formed. In FIG. 3, the second thin-film transistor (TFT2) 23 controls a current for causing an organic light emitting device 24 to emit light. In the pixel circuit 2 of FIG. 3, when a selection signal is applied to the gate selection line Gi, the first thin-film transistor (TFT1) 21 is turned on, and an image signal Ii is supplied to the capacitor (Cadd) 22 so that the gate voltage of the second thin-film transistor (TFT2) 23 may be determined. A current is supplied from the current supply line Ci to the organic light emitting device 24 in accordance with the gate voltage of the second thin-film transistor (TFT2) (23). Here, the gate potential of the second thin-film transistor (TFT2) 23 is held in the capacitor (Cadd) 22 until the first thin-film transistor (TFT1) 21 is selected for next scan. Accordingly, a current continues to flow in the organic light emitting device 24 until the next scan is performed. As a result, the organic light emitting device 24 can be caused to emit light at all times during a one-frame period.

It should be noted that the organic light emitting device according to the present invention can be used also in a voltage writable display apparatus in which a thin-film transistor controls a voltage between the electrodes of the organic light emitting device 24, though illustration is omitted.

Figure 4:
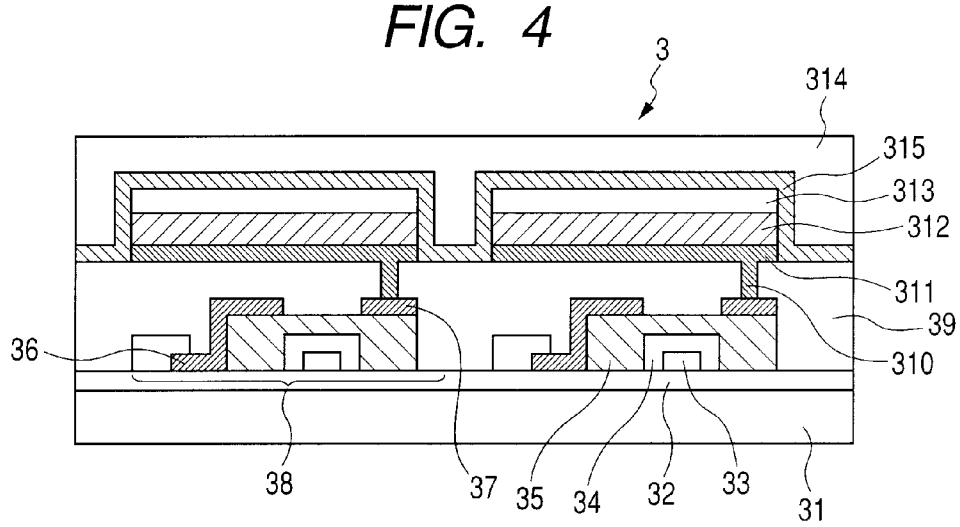
FIG. 4 is a schematic sectional view illustrating an organic light emitting device and a TFT below the device.

FIG. 4 is a schematic view illustrating an example of the sectional structure of a TFT substrate used in the display apparatus of FIG. 1. Details about the structure are described below while an example of a production process for the TFT substrate is shown.

Upon production of a display apparatus 3 of FIG. 4, first, the upper portion of the substrate 31 such as glass is coated with the moisture-proof film 32 for protecting a member to be formed on the substrate (a TFT or an organic layer). Silicon oxide, a composite of silicon oxide and silicon nitride, or the like is used as a material of which the moisture-proof film 32 is formed. Next, a metal such as Cr is formed into a film by sputtering, and the film is patterned into a predetermined circuit shape. Thus, the gate electrode 33 is formed.

Subsequently, silicon oxide or the like is formed into a film by, for example, a plasma CVD method or a catalytic chemical vapor deposition method (cat-CVD method), and the film is patterned. Thus, the gate insulating film 34 is formed. Next, a silicon film is formed by a plasma CVD method or the like (annealing is performed at a temperature of 290° C. or higher in some cases), and the film is patterned in accordance with the circuit shape. Thus, the semiconductor film 35 is formed.

Further, the semiconductor film 35 is provided with the drain electrode 36 and the source electrode 37 so that the TFT device 38 may be produced. Thus, such circuit as illustrated in FIG. 3 is formed. Next, the insulating film 39 is formed on the upper portion of the TFT device 38. Next, the contact hole (through-hole) 310 is formed such that the source electrode 37 and the anode 311 for an organic light emitting device formed of a metal may be connected to each other.

The one or multiple organic layers 312 and the cathode 313 are sequentially laminated on the anode 311. As a result, the display apparatus 3 can be obtained. In this case, the first protective layer 314 and the second protective layer 315 may be provided for preventing the deterioration of an organic light emitting device. When the display apparatus using the organic light emitting device of the present invention is driven, the display apparatus can achieve display which has good image quality and which is stable over a long time period.

It should be noted that the above-mentioned display apparatus is not particularly limited to a switching device, and a single-crystal silicon substrate, MIM device, a-Si type device, or the like can be easily applied to the system.

One or multiple organic emission layers and a cathode layer are sequentially laminated on the above-mentioned ITO electrode. As a result, an organic light emitting display panel can be obtained. When the display panel using the organic compound of the present invention is driven, the display panel can achieve display which has good image quality and which is stable over a long time period.

Hereinafter, the present invention is described specifically by way of examples. However, the present invention is not limited to the examples.

EXAMPLE 1

Synthesis of Exemplified Compound C101

(1) Synthesis of 2-chlorochrysene

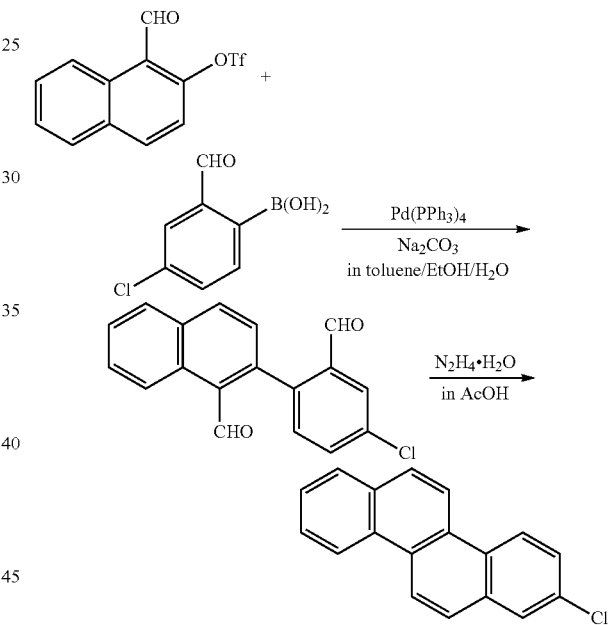

First, 1-formylnaphthalen-2-yl-trifluoromethanesulfonic acid was synthesized from 2-hydroxy-1-naphthaldehyde. In addition, 4-chloro-2-formylphenylboronic acid was synthesized from 2-bromo-5-chlorobenzaldehyde.

The following reagents and solvents were loaded into a 300-mL three-necked flask.
1-formylnaphthalen-2-yl-trifluoromethanesulfonic acid:
  9.97 g (32.8 mmol)
4-chloro-2-formylphenylboronic acid:
  5.75 g (31.2 mmol)
Tetrakis(triphenylphosphine)palladium(0):
  1.0 g (0.86 mmol)
Toluene: 100 mL
Ethanol: 50 mL
10-wt % aqueous solution of sodium carbonate:
  50 mL The reaction solution was heat-refluxed for 3 hours under nitrogen while being stirred. After the completion of the reaction, the reaction solution was washed with water and dried over sodium sulfate. Then, the dried product was concentrated. Thus, a crude product was obtained. Next, the crude product was purified by silica gel column chromatography (eluent: toluene/heptane=2/1). Thus, 6.55 g of 2-(4-chloro-2-formylphenyl)-1-naphthaldehyde were obtained (in 71% yield).

Subsequently, the following reagent and solvent were loaded into a 500-mL three-necked flask provided with a dropping funnel.
2-(4-chloro-2-formylphenyl)-1-naphthaldehyde:
  6.55 g (22.2 mmol)
Acetic acid: 350 mL The reaction solution was heat-refluxed under nitrogen while being stirred. A solution prepared by mixing 30 mL of acetic acid with 1.45 g (28.9 mmol) of hydrazine monohydrate was slowly dropped from the dropping funnel to the reaction solution over 50 minutes. After the completion of the dropping, the mixture was continuously heat-refluxed for an additional 3.5 hours. After the completion of the reaction, 100 mL of water were added to the reaction solution, and the mixture was stirred. The precipitated product was separated by filtration, and was then purified by dispersion washing under heat with a mixed solvent of methanol and acetone. Thus, 4.44 g of 2-chlorochrysene were obtained (in 76% yield).

In addition, the resultant compound was identified by ¹H-NMR analysis.
(¹H-NMR (400 MHz, CDCl₃)) δ 8.75 (d, 1H), 8.73 (d, 1H), 8.68 (d, 1H), 8.62 (d, 1H), 8.01 (d, 1H), 7.99 (dd, 1H), 7.95 (d, 1H), 7.90 (d, 1H), 7.74 (td, 1H), 7.64 (m, 2H).

(2) Synthesis of 6,12-dibromo-2-chlorochrysene

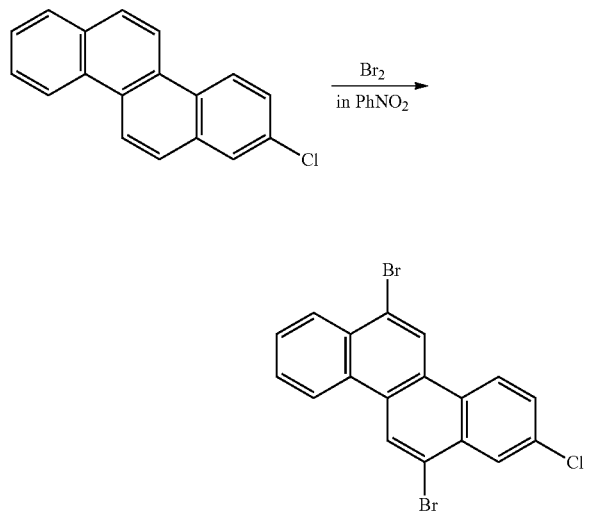

The following reagent and solvent were loaded into a 300-mL three-necked flask provided with a dropping funnel.
2-chlorochrysene: 4.10 g (15.6 mmol)
Nitrobenzene: 170 mL The reaction solution was heated to 105° C. under nitrogen while being stirred. A solution prepared by mixing 30 mL of nitrobenzene with 1.8 mL (34.9 mmol) of bromine was slowly dropped from the dropping funnel to the reaction solution over 10 minutes. After the completion of the dropping, the mixture was continuously heated for an additional 3.5 hours. After the completion of the reaction, 50 mL of methanol were added to the reaction solution, and the mixture was stirred. The precipitated crystal was separated by filtration, and was then washed with methanol, ethanol, and hexane. The resultant crystal was purified by recrystallization from toluene. Thus, 5.94 g of 6,12-dibromo-2-chlorochrysene were obtained (in 84% yield).

In addition, the resultant compound was identified by ¹H-NMR analysis.
(¹H-NMR (400 MHz, CDCl₃)) δ 9.01 (s, 1H), 8.91 (s, 1H), 8.67 (d, 1H), 8.61 (d, 1H), 8.50-8.35 (m, 2H), 8.77-8.73 (m, 3H).

(3) Synthesis of Intermediate Cl-201

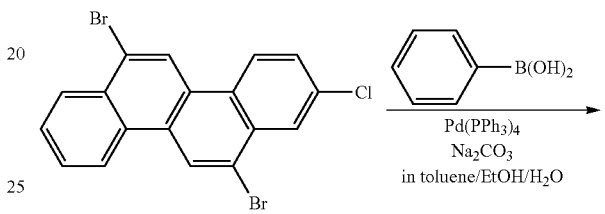

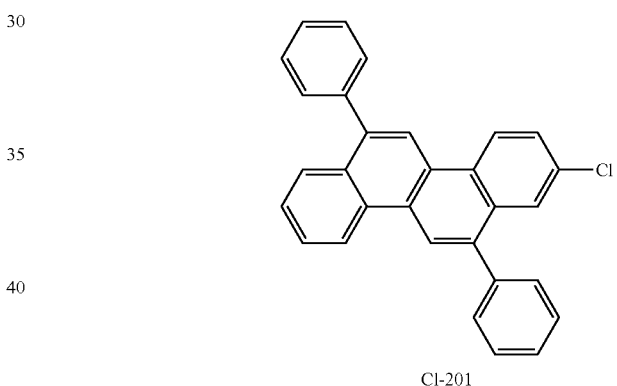

Cl-201

The following reagents and solvents were loaded into a 300-mL recovery flask.
6,12-dibromo-2-chlorochrysene: 2.50 g (5.94 mmol)
Phenylboronic acid: 1.59 g (13.1 mmol)
Tetrakis(triphenylphosphine)palladium(0):
  0.34 g (0.30 mmol)
Toluene: 80 mL
Ethanol: 40 mL
10-wt % aqueous solution of sodium carbonate:
  40 mL The reaction solution was heat-refluxed for 4 hours under nitrogen while being stirred. After the completion of the reaction, the reaction solution was washed with water and dried over sodium sulfate. Then, the dried product was concentrated. Thus, a crude product was obtained. Next, the crude product was purified by silica gel column chromatography (eluent: heptane/toluene=4/1). Thus, 2.30 g of Intermediate Cl-201 were obtained (in 93% yield).

(4) Synthesis of Intermediate Bpin-201

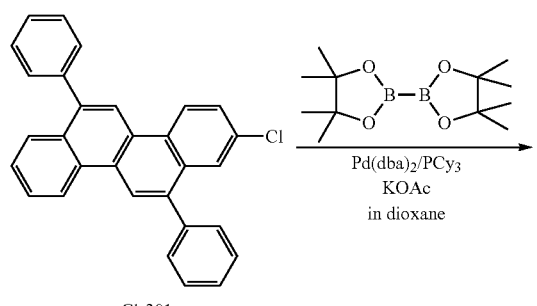

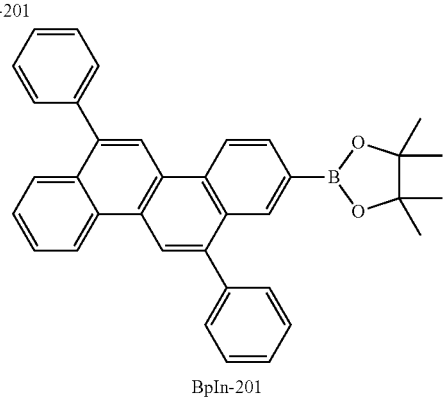

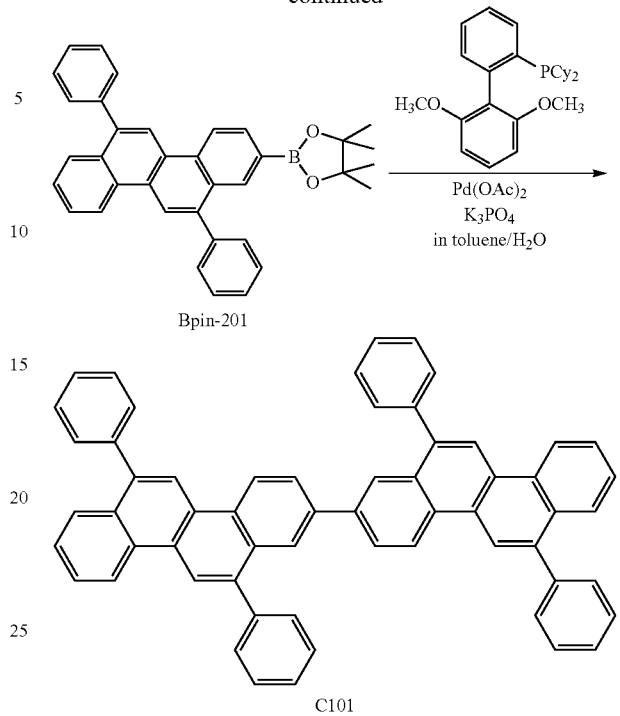

The following reagents and solvent were loaded into a 50-mL recovery flask.
Intermediate Cl-201: 400 mg (0.96 mmol)
Bis(pinacolato)diboron: 270 mg (1.06 mmol)
Bis(dibenzylideneacetone)palladium(0): 33 mg (58 μmol)
Tricyclohexylphosphine: 39 mg (0.14 mmol)
Potassium acetate: 142 mg (1.45 mmol)
1,4-dioxane: 10 mL The reaction solution was stirred at 90° C. for 12 hours under nitrogen. After the completion of the reaction, the reaction solution was washed with water and dried over sodium sulfate. Then, the dried product was concentrated. Thus, a crude product was obtained. Next, the crude product was purified by silica gel column chromatography (eluent: heptane/toluene=1/1). Thus, 208 mg of Intermediate Bpin-201 were obtained (in 43% yield).

(5) Synthesis of Exemplified Compound C101

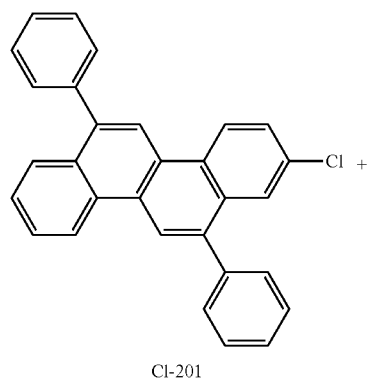

The following reagents and solvents were loaded into a 50-mL recovery flask.
Intermediate Cl-201: 170 mg (0.41 mmol)
Intermediate Bpin-201: 207 mg (0.41 mmol)
Palladium(II)acetate: 3.4 mg (15 μmol)
Dicyclohexyl(2',6'-dimethoxybiphenyl-2-yl)phosphine: 12 mg (29 μmol)
Potassium phosphate: 174 mg (0.82 mmol)
Toluene: 10 mL
Water: 1 mL The reaction solution was stirred at 100° C. for 10 hours under nitrogen. After the completion of the reaction, the precipitated crystal was separated by filtration, and was then washed with water, ethanol, and acetone. Thus, a crude product was obtained. Next, the crude product was dissolved in chlorobenzene under heat, was subjected to hot filtration, and was then recrystallized from chlorobenzene and octane twice. The resultant crystal was vacuum-dried at 150° C., and was then subjected to sublimation purification under conditions of $10^{-4}$ Pa and 390° C. Thus, 182 mg of Exemplified Compound C101 having a high purity were obtained (in 59% yield).

The resultant compound was identified by mass spectrometry.
(Matrix-Assisted Laser Desorption/Ionization Time-of-Flight Mass Spectrometry (MALDI-TOF-MS))
Observed value: m/z=758.27
Calculated value: $C_{60}H_{38}$=758.30

In addition, the energy gap of Exemplified Compound C101 was measured by the following method. Exemplified Compound C101 was deposited from the vapor onto a glass substrate under heat. Thus, a deposited thin film having a thickness of 20 nm was obtained. The light absorption spectrum of the deposited thin film was measured with an ultraviolet and visible spectrophotometer (V-560 manufactured by JASCO Corporation). The absorption edge of the resultant light absorption spectrum was determined to be 390 nm, and Exemplified Compound C101 had an energy gap of 3.18 eV.

EXAMPLE 2

Synthesis of Exemplified Compound C201

(1) Synthesis of 3-chlorochrysene

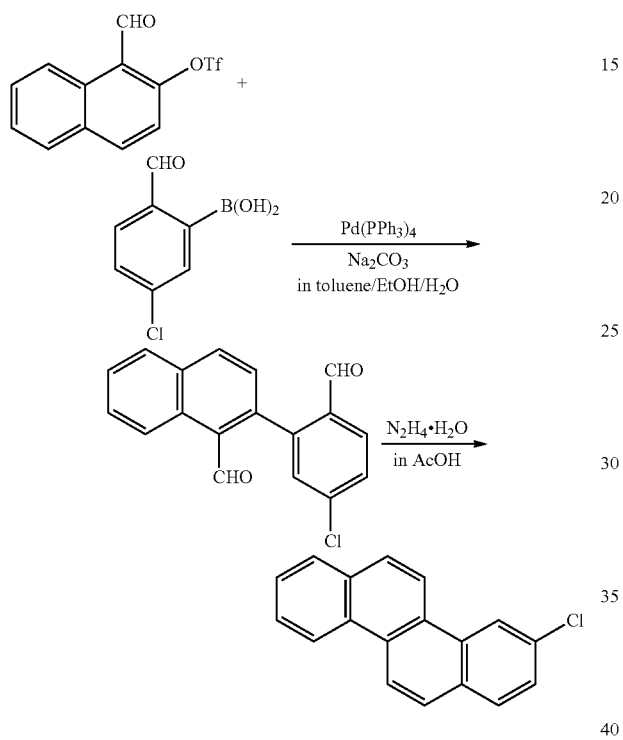

5-chloro-2-formylphenylboronic acid was synthesized from 2-bromo-4-chlorobenzaldehyde.

The following reagents and solvents were loaded into a 200-mL recovery flask.
1-formylnaphthalen-2-yl-trifluoromethanesulfonic acid:
  5.37 g (17.7 mmol)
5-chloro-2-formylphenylboronic acid:
  2.96 g (16.1 mmol)
Tetrakis(triphenylphosphine)palladium(0):
  0.60 g (0.52 mmol)
Toluene: 60 mL
Ethanol: 30 mL
10-wt % aqueous solution of sodium carbonate:
  30 mL The reaction solution was heat-refluxed for 7 hours under nitrogen while being stirred. After the completion of the reaction, the reaction solution was washed with water and dried over sodium sulfate. Then, the dried product was concentrated. Thus, a crude product was obtained. Next, the crude product was purified by silica gel column chromatography (eluent: toluene/heptane=5/1). Thus, 2.24 g of 2-(5-chloro-2-formylphenyl)-1-naphthaldehyde were obtained (in 47% yield).

Subsequently, the following reagent and solvent were loaded into a 300-mL three-necked flask provided with a dropping funnel.
2-(5-chloro-2-formylphenyl)-1-naphthaldehyde:
  2.05 g (6.96 mmol)
Acetic acid: 160 mL The reaction solution was heat-refluxed under nitrogen while being stirred. A solution prepared by mixing 25 mL of acetic acid with 0.46 g (9.04 mmol) of hydrazine monohydrate was slowly dropped from the dropping funnel to the reaction solution over 20 minutes. After the completion of the dropping, the mixture was continuously heat-refluxed for an additional 5 hours. After the completion of the reaction, 50 mL of water were added to the reaction solution, and the mixture was stirred. The precipitated crystal was separated by filtration, and was then purified by dispersion washing under heat with a mixed solvent of methanol and acetone. Thus, 1.50 g of 3-chlorochrysene were obtained (in 82% yield).

In addition, the resultant compound was identified by $^1$H-NMR analysis.
($^1$H-NMR (400 MHz, CDCl$_3$)) δ 8.78 (d, 1H), 8.75 (d, 1H), 8.72 (d, 1H), 8.61 (d, 1H), 8.05-7.90 (m, 4H), 7.73 (td, 1H), 7.66 (t, 1H), 7.59 (dd, 1H).

(2) Synthesis of 6,12-dibromo-3-chlorochrysene

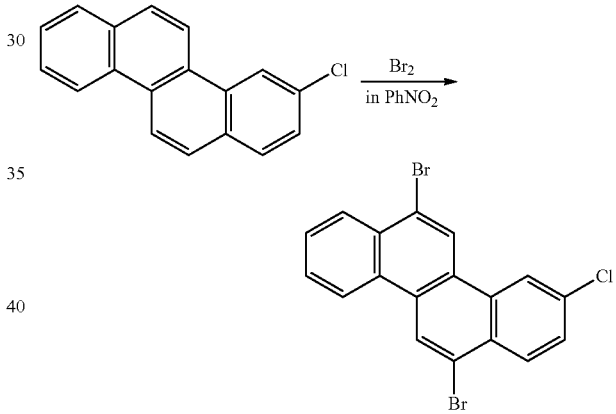

The following reagent and solvent were loaded into a 200-mL three-necked flask provided with a dropping funnel.
3-chlorochrysene: 1.49 g (5.67 mmol)
Nitrobenzene: 65 mL The reaction solution was heated to 105° C. under nitrogen while being stirred. A solution prepared by mixing 10 mL of nitrobenzene with 0.62 mL (12.0 mmol) of bromine was slowly dropped from the dropping funnel to the reaction solution over 10 minutes. After the completion of the dropping, the mixture was continuously heated for an additional 3.5 hours. After the completion of the reaction, 30 mL of methanol were added to the reaction solution, and the mixture was stirred. The precipitated crystal was separated by filtration, and was then washed with methanol, ethanol, and hexane. The resultant crystal was purified by recrystallization from toluene. Thus, 1.99 g of 6,12-dibromo-3-chlorochrysene were obtained (in 84% yield).

In addition, the resultant compound was identified by $^1$H-NMR analysis.
($^1$H-NMR (400 MHz, CDCl$_3$)) δ 8.99 (s, 1H), 8.89 (s, 1H), 8.75-8.65 (m, 2H), 8.46 (m, 1H), 8.38 (d, 1H), 7.79 (m, 2H), 7.70 (dd, 1H).

(3) Synthesis of Intermediate Cl-301

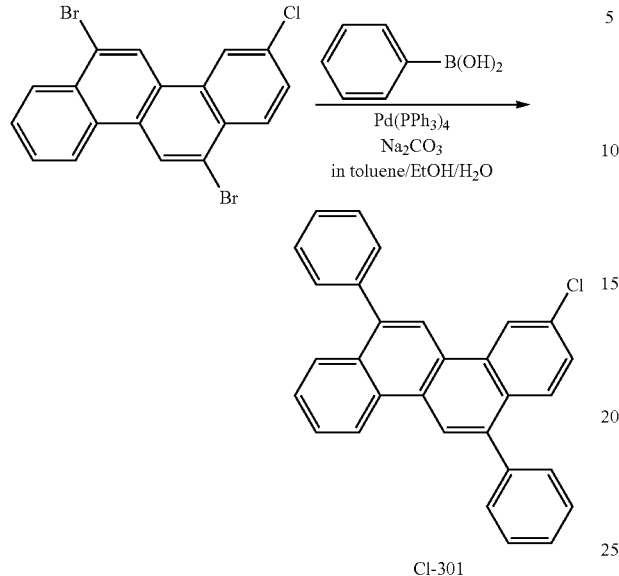

The following reagents and solvents were loaded into a 200-mL recovery flask.
6,12-dibromo-3-chlorochrysene: 1.00 g (2.38 mmol)
Phenylboronic acid: 0.64 g (5.23 mmol)
Tetrakis(triphenylphosphine)palladium(0):
    0.14 g (0.12 mmol)
Toluene: 40 mL
Ethanol: 20 mL
10-wt % aqueous solution of sodium carbonate:
    20 mL The reaction solution was heat-refluxed for 4 hours under nitrogen while being stirred. After the completion of the reaction, 20 mL of water were added to the reaction solution, and the mixture was stirred. The precipitated crystal was separated by filtration, and was then washed with water, ethanol, and acetone. Thus, a crude product was obtained. Next, the crude product was dissolved in toluene under heat. After that, the solution was subjected to hot filtration, and was then purified by dispersion washing under heat with ethanol. Thus, 846 mg of Intermediate Cl-301 were obtained (in 86% yield).

(4) Synthesis of Intermediate Bpin-301

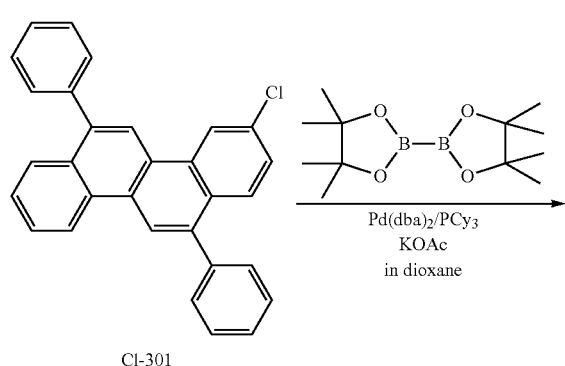

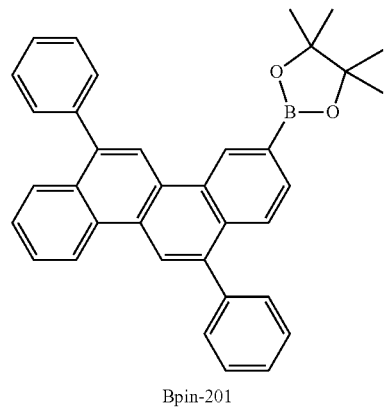

Bpin-201

The following reagents and solvent were loaded into a 50-mL recovery flask.
Intermediate Cl-301: 370 mg (0.89 mmol)
Bis(pinacolato)diboron: 272 mg (1.07 mmol)
Bis(dibenzylideneacetone)palladium(0):
    51 mg (89 µmol)
Tricyclohexylphosphine: 63 mg (0.22 mmol)
Potassium acetate: 175 mg (1.78 mmol)
1,4-dioxane: 15 mL The reaction solution was stirred at 90° C. for 7 hours under nitrogen. After the completion of the reaction, the reaction solution was washed with water and dried over sodium sulfate. Then, the dried product was concentrated. Thus, a crude product was obtained. Next, the crude product was purified by silica gel column chromatography (eluent: heptane/toluene=1/1). Thus, 180 mg of Intermediate Bpin-301 were obtained (in 40% yield).

(5) Synthesis of Exemplified Compound C201

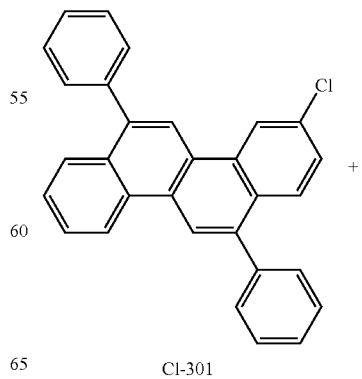

Cl-301 +

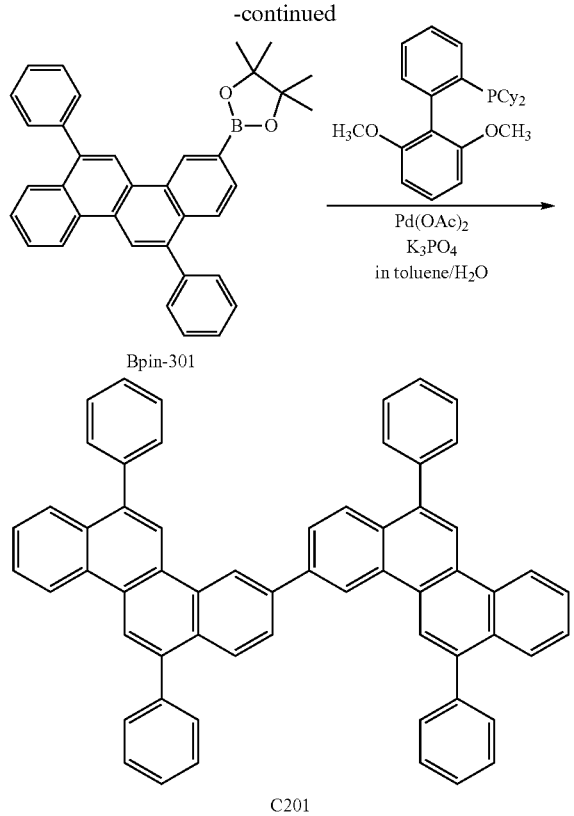

Bpin-301

C201

The following reagents and solvents were loaded into a 50-mL recovery flask.
Intermediate Cl-301: 155 mg (0.37 mmol)
Intermediate Bpin-301: 180 mg (0.36 mmol)
Palladium(II)acetate: 5 mg (22 μmol)
Dicyclohexyl(2',6'-dimethoxybiphenyl-2-yl)phosphine: 19 mg (46 μmol)
Potassium phosphate: 226 mg (1.07 mmol)
Toluene: 12 mL
Water: 0.25 mL The reaction solution was stirred at 100° C. for 4.5 hours under nitrogen. After the completion of the reaction, the precipitated crystal was separated by filtration, and was then washed with water and methanol. Thus, a crude product was obtained. Next, the crude product was dissolved in a mixed solvent of toluene and chlorobenzene under heat, was subjected to hot filtration, and was then recrystallized from a mixed solvent of chlorobenzene, toluene, and octane. The resultant crystal was further purified by dispersion washing under heat with a mixed solvent of tolulene, chlorobenzene, and ethyl acetate, was vacuum-dried at 150° C., and was then subjected to sublimation purification under conditions of $10^{-4}$ Pa and 390° C. Thus, 163 mg of Exemplified Compound C201 having a high purity were obtained (in 60% yield).

The resultant compound was identified by mass spectrometry.
(MALDI-TOF-MS)
Observed value: m/z=758.39
Calculated value: $C_{60}H_{38}$=758.30

In addition, the energy gap of Exemplified Compound C201 was measured in the same manner as in Example 1-(5).

As a result, the absorption edge of the light absorption spectrum was 409 nm, and Exemplified Compound C201 had an energy gap of 3.03 eV.

EXAMPLE 3

Synthesis of Exemplified Compound C301

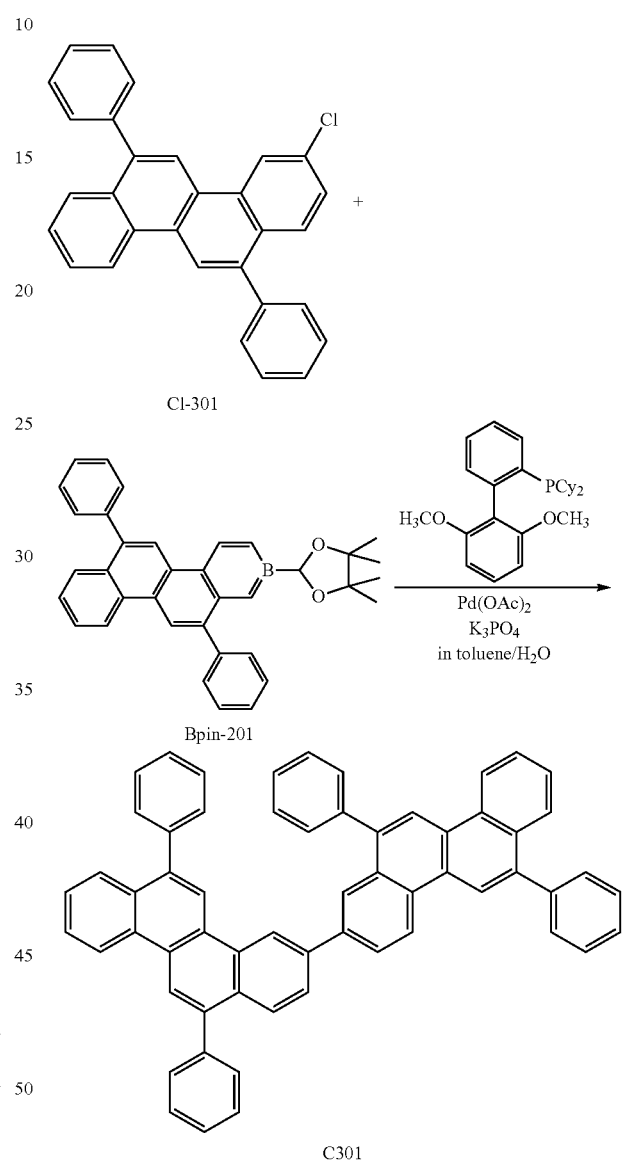

Cl-301

Bpin-201

C301

The following reagents and solvents were loaded into a 50-mL recovery flask.
Intermediate Cl-301: 250 mg (0.60 mmol)
Intermediate Bpin-201: 336 mg (0.66 mmol)
Palladium(II)acetate: 7 mg (31 μmol)
Dicyclohexyl(2',6'-dimethoxybiphenyl-2-yl)phosphine: 33 mg (80 μmol)
Potassium phosphate: 386 mg (1.82 mmol)
Toluene: 20 mL
Water: 0.50 mL The reaction solution was stirred at 100° C. for 5 hours under nitrogen. After the completion of the reaction, the precipitated crystal was separated by filtration, and was then washed with water, ethanol, and hexane. Thus, a crude product was obtained. Next, the crude product was dissolved in toluene under heat, was subjected to hot filtration, and was then recrystallized from a mixed solvent of toluene and octane. The resultant crystal was vacuum-dried at 150° C., and was then subjected to sublimation purification under conditions of $10^{-4}$ Pa and 390° C. Thus, 221 mg of Exemplified Compound C301 having a high purity were obtained (in 48% yield).

The resultant compound was identified by mass spectrometry.

(MALDI-TOF-MS)

Observed value: m/z=758.33

Calculated value: $C_{60}H_{38}$=758.30

In addition, the energy gap of Exemplified Compound C301 was measured in the same manner as in Example 1-(5). As a result, the absorption edge of the light absorption spectrum was 409 nm, and Exemplified Compound C301 had an energy gap of 3.03 eV.

COMPARATIVE EXAMPLE 1

Comparison Between Energy Gaps

The energy gaps of Comparative Compounds H01 to H05 shown below were each measured in the same manner as in Example 1-(5). Table 2 shows the results together with the results of Examples 1 to 3.

(Comparative Compounds)

H01

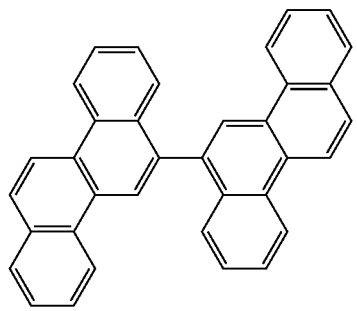

H02

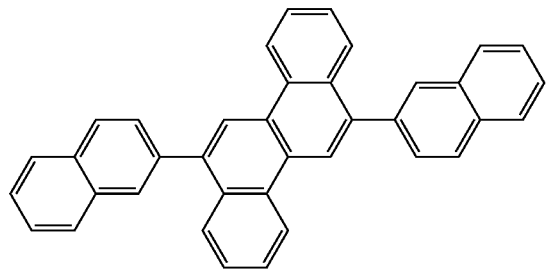

H03

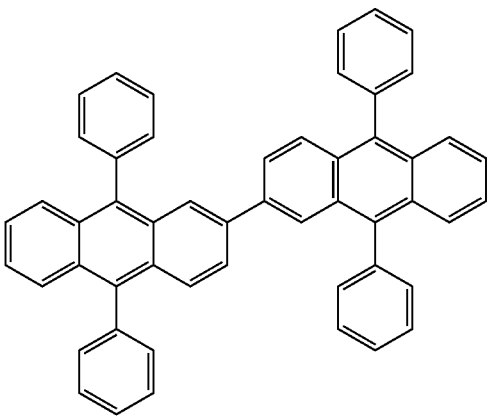

H04

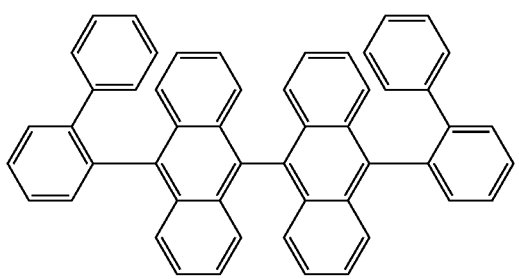

H05

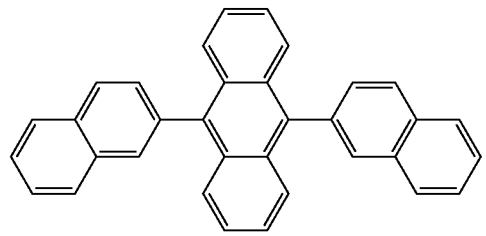

TABLE 2

|  | Absorption edge | Energy gap |
|---|---|---|
| Exemplified Compound C101 | 390 nm | 3.18 eV |
| Exemplified Compound C201 | 409 nm | 3.03 eV |
| Exemplified Compound C301 | 409 nm | 3.03 eV |
| Comparative Compound H01 | 371 nm | 3.34 eV |
| Comparative Compound H02 | 395 nm | 3.14 eV |
| Comparative Compound H03 | 443 nm | 2.80 eV |
| Comparative Compound H04 | 425 nm | 2.92 eV |
| Comparative Compound H05 | 426 nm | 2.91 eV |

The 6,6'-bichrysene compound as Comparative Compound H01 had an extremely large energy gap as compared to those of the bichrysene compounds of the present invention.

EXAMPLE 4

In this example, a device (including an anode, a hole transport layer, an emission layer, an electron transport layer, and a cathode) described in the third example of a multilayer organic light emitting device was produced by the following method.

ITO was formed into a film having a thickness of 110 nm to serve as the anode on a glass substrate by a sputtering method, and the resultant was used as a transparent, conductive supporting substrate (ITO substrate). The following organic compound layers and electrode layers were continuously formed on the ITO substrate by vacuum deposition based on resistance heating in a vacuum chamber having a pressure of $10^{-5}$ Pa. In this case, the device production was performed so that an opposing electrode area might be 3 mm².

| | |
|---|---|
| Hole transport layer (25 nm) | HTL-1 |
| Emission layer (30 nm) | Host: Exemplified Compound C101 |
| | Guest: BD-3 (5 wt %) |
| Electron transport layer (30 nm) | ETL-1 |
| Metal electrode layer 1 (0.5 nm) | LiF |
| Metal electrode layer 2 (100 nm) | Al |

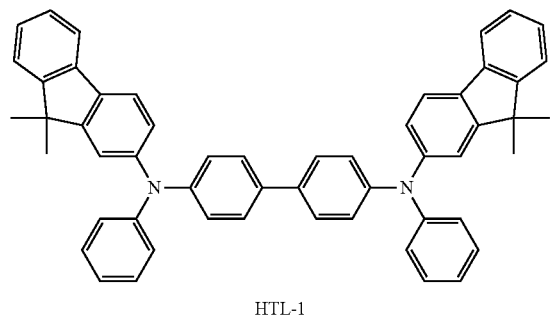

HTL-1

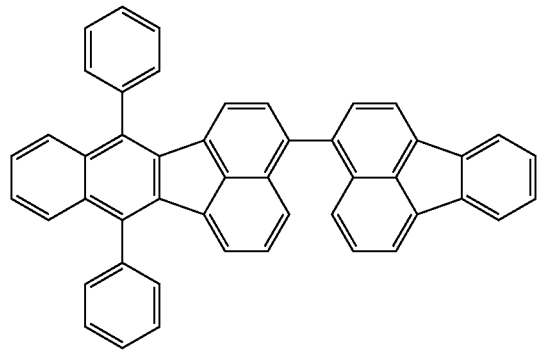

BD-3

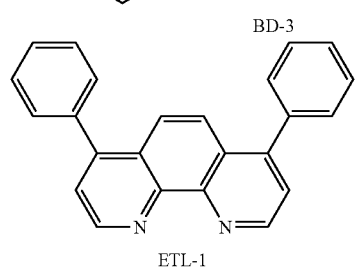

ETL-1

Next, the resultant was covered with a protective glass plate and sealed with an acrylic resin-based adhesive in a dry air atmosphere in order that the organic light emitting device might not deteriorate owing to moisture adsorption. Thus, the organic light emitting device was obtained.

An applied voltage of 4.5 V was applied to the resultant organic light emitting device while the ITO electrode was used as a positive electrode and the Al electrode was used as a negative electrode. As a result, the device was observed to emit blue light having a luminance of 1000 cd/m² with a light emitting efficiency of 7.5 cd/A. In addition, CIE chromaticity coordinates (x, y) in the device were (0.14, 0.22). Further, when the device was durably driven for 200 hours while a constant current density of 50 mA/cm² was kept, the ratio of reduction in luminance from the initial luminance was 19%.

EXAMPLE 5

A device was produced in the same manner as in Example 4 except that Exemplified Compound C201 was used instead of Exemplified Compound C101 as a host for the emission layer in Example 4. In addition, the resultant device was evaluated in the same manner as in Example 4. Table 3 shows the results.

EXAMPLE 6

A device was produced in the same manner as in Example 4 except that Exemplified Compound C301 was used instead of Exemplified Compound C101 as a host for the emission layer in Example 4. In addition, the resultant device was evaluated in the same manner as in Example 4. Table 3 shows the results.

COMPARATIVE EXAMPLE 2

A device was produced in the same manner as in Example 4 except that Comparative Compound H01 was used instead of Exemplified Compound C101 as a host for the emission layer in Example 4. In addition, the resultant device was evaluated in the same manner as in Example 4. Table 3 shows the results.

COMPARATIVE EXAMPLE 3

A device was produced in the same manner as in Example 4 except that Comparative Compound H05 was used instead of Exemplified Compound C101 as a host for the emission layer in Example 4. In addition, the resultant device was evaluated in the same manner as in Example 4. Table 3 shows the results.

TABLE 3

| | Host | CIE chromaticity | Applied voltage @1000 cd/m² (V) | Light emitting efficiency @1000 cd/m² (V) | Ratio of reduction in luminance after 200 hours @50 mA/cm² |
|---|---|---|---|---|---|
| Example 4 | Exemplified Compound C101 | (0.14, 0.22) | 4.5 | 7.5 | 19% |
| Example 5 | Exemplified Compound C201 | (0.14, 0.21) | 4.2 | 8.0 | 10% |
| Example 6 | Exemplified Compound C301 | (0.14, 0.21) | 4.1 | 8.2 | 9% |
| Comparative Example 2 | Comparative Compound H01 | (0.14, 0.22) | 6.3 | 3.6 | 67% |
| Comparative Example 3 | Comparative Compound H05 | (0.14, 0.24) | 3.9 | 4.0 | 42% |

EXAMPLE 7

In this example, a device (including an anode, a hole transport layer, an emission layer, an electron transport layer, and a cathode) described in the third example of a multilayer organic light emitting device in which the electron transport layer was formed of two layers having different ionization potential was produced by the following method.

The following organic compound layers and electrode layers were continuously formed on an ITO substrate produced in the same manner as in Example 4 by vacuum deposition based on resistance heating in a vacuum chamber having a pressure of $10^{-5}$ Pa. In this case, the device production was performed so that an opposing electrode area might be 3 mm$^2$.

| | |
|---|---|
| Hole transport layer (30 nm) | HTL-2 |
| Emission layer (35 nm) | Host: BH-1, Guest: BD-7 (5 wt %) |
| Electron transport layer 1 (10 nm) | Exemplified Compound C101 |
| Electron transport layer 2 (25 nm) | ETL-1 |
| Metal electrode layer 1 (0.5 nm) | LiF |
| Metal electrode layer 2 (100 nm) | Al |

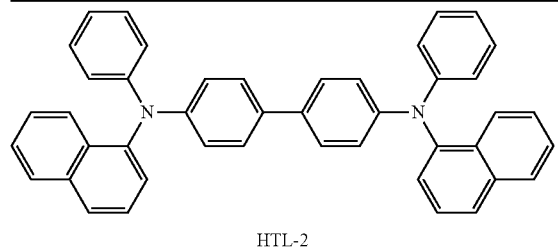

HTL-2

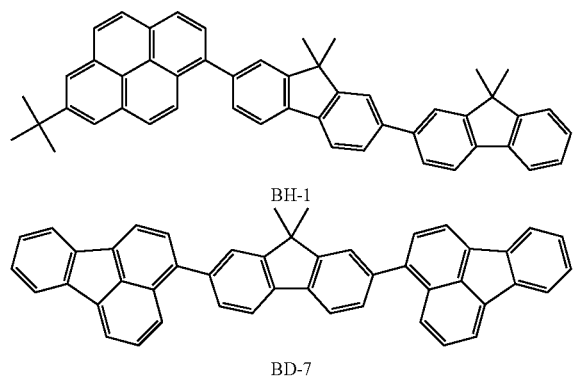

BH-1

BD-7

Next, the resultant was covered with a protective glass plate and sealed with an acrylic resin-based adhesive in a dry air atmosphere in order that the organic light emitting device might not deteriorate owing to moisture adsorption. Thus, the organic light emitting device was obtained.

An applied voltage of 4.1 V was applied to the resultant organic light emitting device while the ITO electrode was used as a positive electrode and the Al electrode was used as a negative electrode. As a result, the device was observed to emit blue light having a luminance of 1200 cd/m$^2$ with a light emitting efficiency of 4.9 cd/A. In addition, CIE chromaticity coordinates (x, y) in the device were (0.15, 0.25). Further, when the device was durably driven for 100 hours while a constant current density of 100 mA/cm$^2$ was kept, the ratio of reduction in luminance from the initial luminance was 15%.

EXAMPLE 8

A device was produced in the same manner as in Example 7 except that Exemplified Compound C201 was used instead of Exemplified Compound C101 as an electron transport layer 1 in Example 7. In addition, the resultant device was evaluated in the same manner as in Example 7. Table 4 shows the results.

EXAMPLE 9

A device was produced in the same manner as in Example 7 except that Exemplified Compound C301 was used instead of Exemplified Compound C101 as an electron transport layer 1 in Example 7. In addition, the resultant device was evaluated in the same manner as in Example 7. Table 4 shows the results.

COMPARATIVE EXAMPLE 4

A device was produced in the same manner as in Example 7 except that Comparative Compound H01 was used instead of Exemplified Compound C101 as an electron transport layer 1 in Example 7. In addition, the resultant device was evaluated in the same manner as in Example 7. Table 4 shows the results.

COMPARATIVE EXAMPLE 5

A device was produced in the same manner as in Example 7 except that Comparative Compound H05 was used instead of Exemplified Compound C101 as an electron transport layer 1 in Example 7. In addition, the resultant device was evaluated in the same manner as in Example 7. Table 4 shows the results.

TABLE 4

| | Electron transport layer 1 | CIE chromaticity | Applied voltage @1200 cd/m$^2$ (V) | Light emitting efficiency @1200 cd/m$^2$ (cd/A) | Ratio of reduction in luminance after 100 hours @100 mA/cm$^2$ |
|---|---|---|---|---|---|
| Example 7 | Exemplified Compound C101 | (0.15, 0.25) | 4.1 | 4.9 | 15% |
| Example 8 | Exemplified Compound C201 | (0.15, 0.24) | 3.9 | 4.8 | 17% |
| Example 9 | Exemplified Compound C301 | (0.15, 0.24) | 3.8 | 4.9 | 18% |
| Comparative Example 4 | Comparative Compound H01 | (0.15, 0.27) | 5.3 | 2.9 | 62% |
| Comparative Example 5 | Comparative Compound H05 | (0.15, 0.28) | 4.2 | 4.3 | 27% |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-063011, filed Mar. 16, 2009, which is hereby incorporated by reference herein in its entirety.

The imvemtion claimed is:

1. An organic light emitting device comprising:
an anode;
a cathode; and
a layer formed of an organic compound which is interposed between the anode and the cathode,
wherein at least one of the anode and the cathode is transparent or semi-transparent; and
wherein the layer formed of an organic compound comprises a bichrysene compound represented by following formula (1):

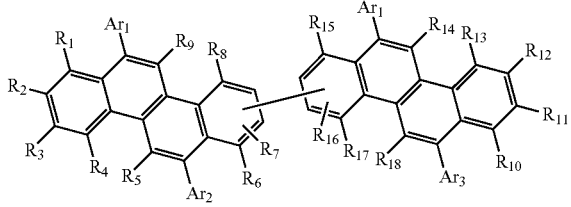

(1)

wherein $R_1$ to $R_{18}$ each independently represents a substituent selected from the group consisting of a hydrogen atom, a substituted or unsubstituted alkyl group, and a substituted or unsubstituted alkoxy group, and
wherein $Ar_1$ to $Ar_4$ each independently represents a substituted or unsubstituted hydrocarbon aromatic ring group.

2. The organic light emitting device according to claim 1, wherein the layer formed of an organic compound comprises an emission layer.

3. The organic light emitting device according to claim 2, wherein the emission layer comprises a host and a guest; and
wherein the host comprises the bichrysene compound.

4. The organic light emitting device according to claim 1, wherein the organic light emitting device has another layer different from the layer formed of an organic compound between the anode and the cathode;
wherein the another layer comprises an emission layer; and
wherein the layer formed of an organic compound comprises an electron transport layer.

5. A display apparatus comprising:
the organic light emitting device according to claim 1; and
a switching device connected to the organic light emitting device.

6. An imaging system comprising:
a display portion having the organic light emitting device according to claim 1; and
an imaging portion.

7. The organic light emitting device according to claim 1, wherein the layer formed of an organic compound comprising the bichrysene compound represented by the general formula (1) comprises 2, 2'-bichrysene compound represented by the following general formula (2):

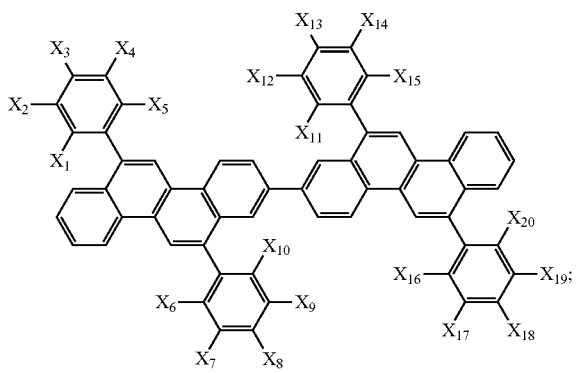

(2)

and
wherein $X_1$ to $X_{20}$ each independently represents a substituent selected from the group consisting of a hydrogen atom, a substituted or unsubstituted alkyl group, a substituted or unsubstituted alkoxy group, and a substituted or unsubstituted hydrocarbon aromatic ring group.

8. The organic light emitting device according to claim 1, wherein the layer formed of an organic compound comprising the bichrysene compound represented by the general formula (1) comprises a 3,3'-bichrysene compound represented by the following general formula (3):

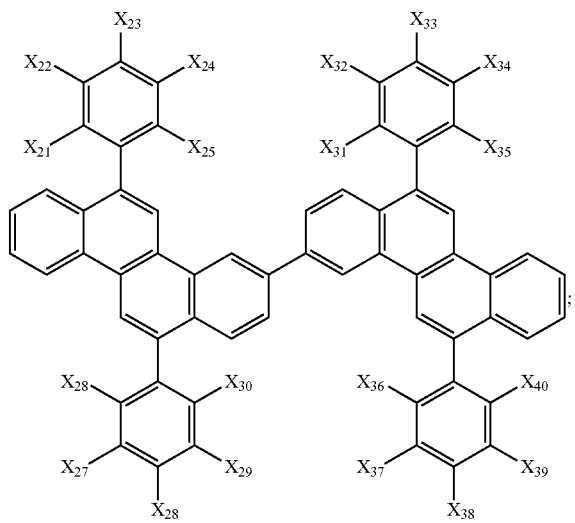

(3)

and
wherein $X_{21}$ to $X_{40}$ each independently represents a substituent selected from the group consisting of a hydrogen atom, a substituted or unsubstituted alkyl group, a substituted or unsubstituted alkoxy group, and a substituted or unsubstituted hydrocarbon aromatic ring group.

9. The organic light emitting device according to claim 1, wherein the layer formed of an organic compound comprising the bichrysene compound represented by the general formula (1) comprises a 2,3'-bichrysene compound represented by the following general formula (4):

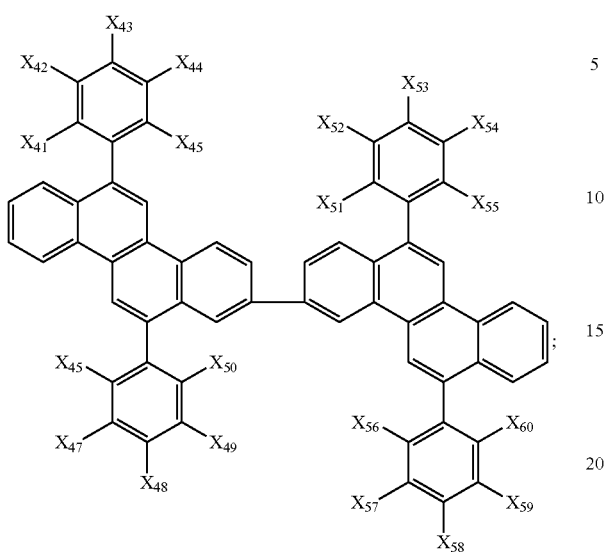
(4)
and
wherein $X_{41}$ to $X_{60}$ each represents a substituent selected from the group consisting of a hydrogen atom, a substituted or unsubstituted alkyl group, a substituted or unsubstituted alkoxy group, and a substituted or unsubstituted hydrocarbon aromatic ring group.
\* \* \* \* \*